(12) United States Patent
Bünemann et al.

(10) Patent No.: US 8,084,575 B2
(45) Date of Patent: Dec. 27, 2011

(54) MILLISECOND ACTIVATION SWITCH FOR SEVEN-TRANSMEMBRANE PROTEINS

(75) Inventors: Moritz Bünemann, Waldbüttelbrunn (DE); Jean-Pierre Vilardaga, Würzburg (DE); Carsten Hoffmann, Leinach (DE); Martin Johannes Lohse, Würzburg (DE)

(73) Assignee: Julius-Maximilians-Universitat, Wurzburg (DE)

( * ) Notice: Subject to any disclaimer, the term of this patent is extended or adjusted under 35 U.S.C. 154(b) by 797 days.

(21) Appl. No.: 10/538,985

(22) PCT Filed: Dec. 19, 2003

(86) PCT No.: PCT/EP03/14679
§ 371 (c)(1),
(2), (4) Date: Aug. 18, 2006

(87) PCT Pub. No.: WO2004/057333
PCT Pub. Date: Jul. 8, 2004

(65) Prior Publication Data
US 2006/0272037 A1    Nov. 30, 2006

(30) Foreign Application Priority Data

Dec. 20, 2002  (DE) ................................. 102 59 874
Mar. 3, 2003   (EP) ..................................... 03004394

(51) Int. Cl.
*C07K 14/705* (2006.01)
(52) U.S. Cl. ....................................................... 530/350
(58) Field of Classification Search .......................... None
See application file for complete search history.

(56) References Cited

U.S. PATENT DOCUMENTS

| | | | |
|---|---|---|---|
| 6,197,534 B1 | 3/2001 | Lakowicz et al. | 435/14 |
| 6,277,627 B1 | 8/2001 | Hellinga | 435/287.1 |
| 2002/0048811 A1 | 4/2002 | Devreotes et al. | 435/325 |

FOREIGN PATENT DOCUMENTS

| | | |
|---|---|---|
| WO | WO 98/40477 | 9/1998 |
| WO | WO 99/66324 | 12/1999 |
| WO | WO 00/34318 | 6/2000 |
| WO | WO 01/09328 | 2/2001 |

OTHER PUBLICATIONS

Altenbach et al., "Structure and function in rhodopsin: mapping light-dependent changes in distance between residue 316 in helix 8 and residues in the sequence 60-75, covering the cytoplasmic end of helices TM1 and TM2 and their connection loop CL1," *Biochemistry*, 40:15493-15500, 2001.
Angers et al., "Detection of beta 2-adrenergic receptor dimerization in living cells using bioluminescence resonance energy transfer (BRET)," *Proc. Natl. Acad. Sci. USA*, 97:3684-3689, 2000.
Angers et al., "Dimerization: an emerging concept for G protein-coupled receptor ontogeny and function," *Annu. Rev. Pharamacol. Toxicol.*, 42:409-435, 2002.
Baird et al., "Circular permutation and receptor insertion within green fluorescent proteins," *Proc. Natl. Acad. Sci. USA*, 96:11241-11246, 1999.
Babcock et al., "Ligand-independent dimerization of CXCR4, a principal HIV-1 coreceptor," *J. Biol. Chem.*, 278:3378-3385, 2003.
Bourne and Meng, "Structure: Rhodopsin Sees the Light," *Science*, 289:733-734, 2000.
Bunemann et al., "Activation and deactivation kinetics of alpha 2A- and alpha 2C-adrenergic receptor-activated G protein-activated inwardly rectifying K+ channel currents," *J. Biol. Chem.*, 276:47512-47517, 2001.
Chang and Weiss, "Site-specific fluorescence reveals distinct structural changes with GABA receptor activation and antagonism," *Nature Neurosci.*, 5:1163-1168, 2002.
Gaietta et al., "Multicolor and Electron Microscopic Imaging of Connexin Trafficking," *Science*, 296:503-507, 2002.
Gardella and Juppner, "Molecular properties of the PTH/PTHrP receptor," *Trends Endocrinol. Metabolism*, 12:210-217, 2001.
GenBank accession No. M97370, Dec. 31, 1994.
GenBank accession No. M99377, Apr. 27, 1993.
GenBank accession No. NM_011199, Nov. 17, 2006.
GenBank accession No. U22401, Sep. 20, 2001.
GenBank accession No. NM_000681, Nov. 17, 2006.
Gether, "Uncovering molecular mechanisms involved in activation of G protein-coupled receptors," *Endocr. Rev.*, 21:90-113, 2000.
Gether et al., "Fluorescent labeling of purified beta 2 adrenergic receptor. Evidence for ligand-specific conformational changes," *J. Biol. Chem.*, 270:28268-28275, 1995.
Ghanouni et al., "Functionally different agonists induce distinct conformations in the G protein coupling domain of the beta 2 adrenergic receptor," *J. Biol. Chem.*, 276:24433-24436, 2001. Ghanouni et al, "Agonist-induced conformational changes in the G-protein-coupling domain of the beta 2 adrenergic receptor," *Proc. Natl. Acad. Sci. USA*, 98:5997-6002, 2001.
Griesbeck et al., "Reducing the environmental sensitivity of yellow fluorescent protein. Mechanism and applications," *J. Biol. Chem.*, 276:29188-29194, 2001.
Griffin et al., "Specific Covalent Labeling of Recombinant Protein Molecules Inside Live Cells," *Science*, 281:269-272, 1998.
Heikal et al., "Molecular spectroscopy and dynamics of intrinsically fluorescent proteins: coral red (dsRed) and yellow (Citrine)," *Proc. Natl. Acad. Sci. USA*, 97:11996-12001, 2000.
Heim, "Green fluorescent protein forms for energy transfer," *Methods Enzymol.*, 302:408-423, 1999.

(Continued)

*Primary Examiner* — Michael Pak
(74) *Attorney, Agent, or Firm* — Fulbright & Jaworski L.L.P.

(57) ABSTRACT

The present invention relates to recombinant seven-transmembrane receptor, whereby the amino terminus of said recombinant receptor is located on an extracellular side and the carboxy-terminus is located on an intracellular side of a membrane, comprising at least two detectable labels, whereby a first of said at least two detectable labels is or is located on the carboxy-terminus and whereby a second of said at least two labels is or is located on the first or third intracellular loop or whereby a first of said at least two labels is or is located on the third intracellular loop. Furthermore, nucleic acid molecules encoding said recombinant seven-transmembrane receptors are described as well as vector and host cells comprising the same. Furthermore, the present invention provides for identification and screening methods for molecules or compounds which are capable of modifying the biological end of pharmacological function of seven-transmembrane receptor proteins. Finally, diagnostic compositions comprising the compounds of the present invention as well as kits comprising said compounds are disclosed.

11 Claims, 16 Drawing Sheets

OTHER PUBLICATIONS

Honda et al., "Spatiotemporal dynamics of guanosine 3',5'-cyclic monophosphate revealed by a genetically encoded, fluorescent indicator," *Proc. Natl. Acad. Sci. USA*, 98:2437-2442, 2001.

Huang et al., "The N-terminal region of the third intracellular loop of the parathyroid hormone (PTH)/PTH-related peptide receptor is critical for coupling to cAMP and inositol phosphate/Ca2+ signal transduction pathways," *J. Biol. Chem.*, 271:33382-33389, 1996.

Illes et al., "Signaling by extracellular nucleotides and nucleosides," *Naunyn-Schmiedebergs Arch. Pharmacol.*, 362:295-298, 2000.

Jensen et al., "Agonist-induced conformational changes at the cytoplasmic side of transmembrane segment 6 in the beta 2 adrenergic receptor mapped by site-selective fluorescent labeling," *J. Biol. Chem.*, 276:9279-9290, 2001.

Karatani et al., "Properties of the bimodal fluorescent protein produced by *Photobacterium phosphoreum*," *Photochem. Photobiol.*, 71:230-236, 2000.

Kobilka and Gether, "Use of fluorescence spectroscopy to study conformational changes in the beta 2-adrenoceptor," *Methods Enzymol.*, 343:170-182, 2002.

Lim and Neubig, "Selective inactivation of guanine-nucleotide-binding regulatory protein (G-protein) alpha and betagamma subunits by urea," *Biochem. J.*, 354:337-344, 2001.

Loshe et al., "Direct optical recording of intrinsic efficacy at a G protein-coupled receptor," *Life Sciences*, 74: 397-404, 2003.

Mercier et al., "Quantitative assessment of beta 1- and beta 2-adrenergic receptor homo- and heterodimerization by bioluminescence resonance energy transfer," *J. Biol. Chem.*, 277:44925-44931, 2002.

Milligan, "Strategies to identify ligands for orphan G-protein-coupled receptors," *Biochemical Society Transactions*, 30:789-793, 2002.

Okada et al., "Activation of rhodopsin: new insights from structural and biochemical studies," *Trends Biochem. Sci.*, 26:318-324, 2001.

Pierce et al., "Seven-transmembrane receptors," *Nat. Rev. Mol. Cell Biol.*, 3:639-650, 2002.

Prasher et al., "Primary structure of the *Aequorea victoria* green-fluorescent protein," *Gene*, 111:229-233, 1992.

Rios et al., "G-protein-coupled receptor dimerization: modulation of receptor function," *Pharmacol. Ther.*, 92:71-87, 2001.

Sheikh et al., "Similar structures and shared switch mechanisms of the beta2-adrenoceptor and the parathyroid hormone receptor. Zn(II) bridges between helices III and VI block activation," *J. Biol. Chem.*, 274: 17033-17041, 1999.

Teller et al., "Advances in Determination of a High-Resolution Three-Dimensional Structure of Rhodopsin, A Model of G-Protein-Coupled Receptors(GPCRs)," *Biochemistry*, 40:7768-7772, 2001.

Strange, "Mechanisms of inverse agonism at G-protein-coupled receptors," *Trends Pharmacol Sci.*, 23:89-95, 2002.

Tsien, "The green fluorescent protein," *Ann. Rev. Biochem.*, 67:509-544, 1998.

Vilardaga et al., "Measurement of the millisecond activation switch of G protein-coupled receptors in living cells," *Nature Biotechnology*, 21:807-812, 2003.

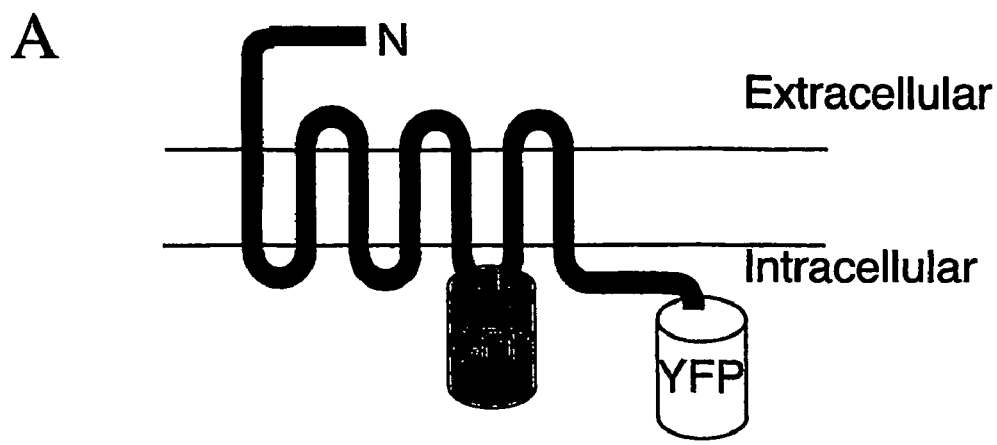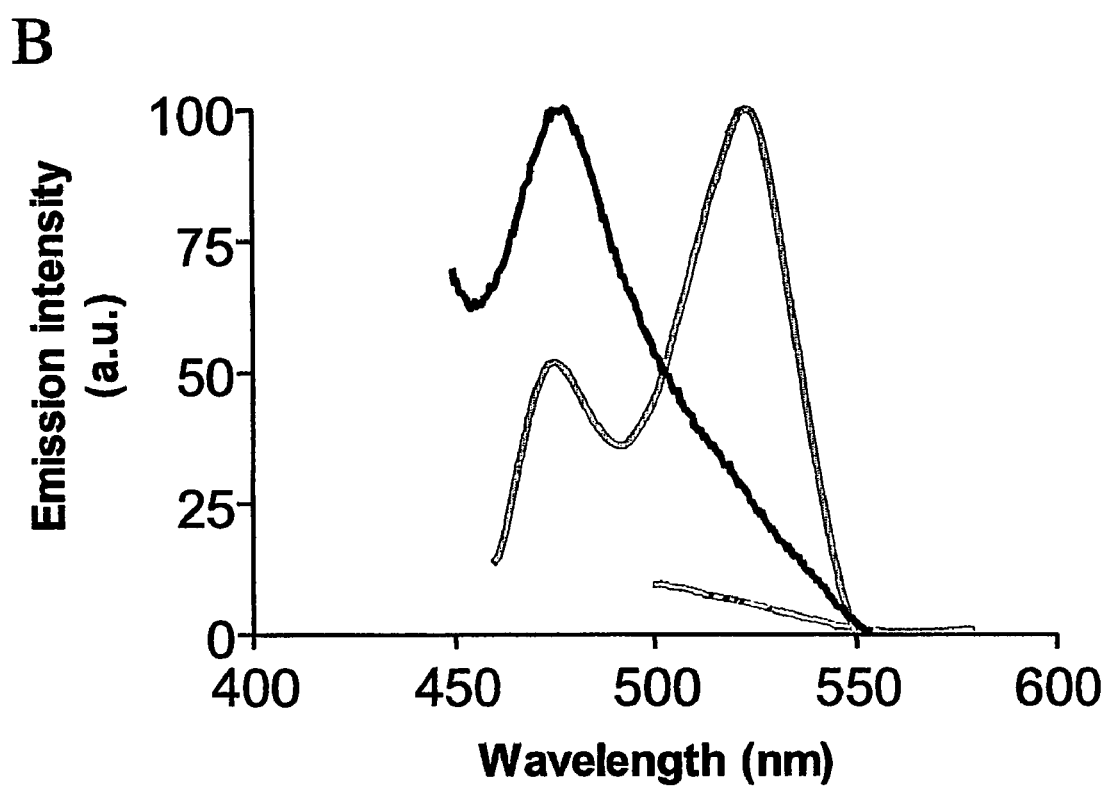
Fig. 1 (part 1)

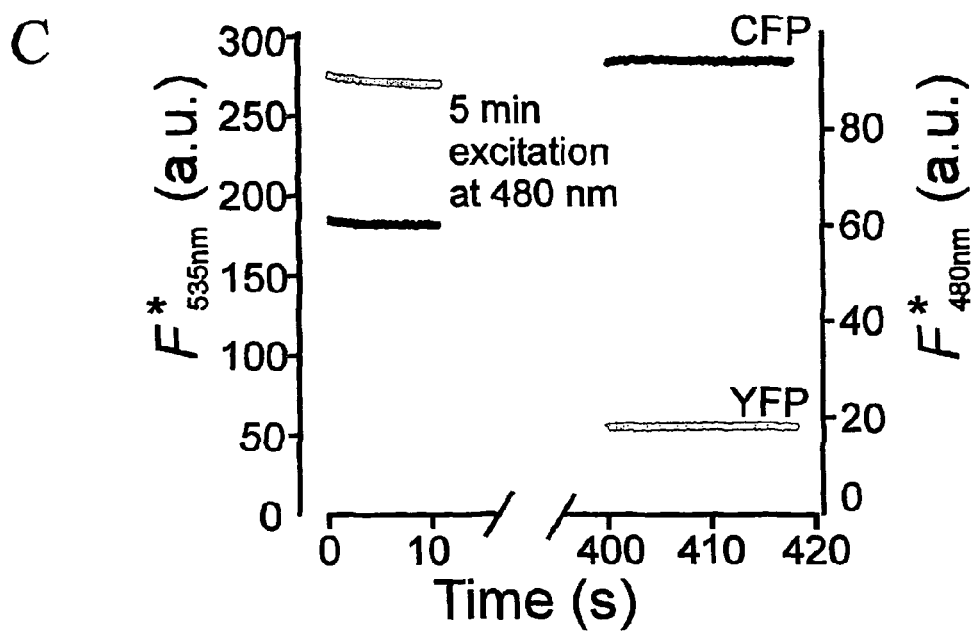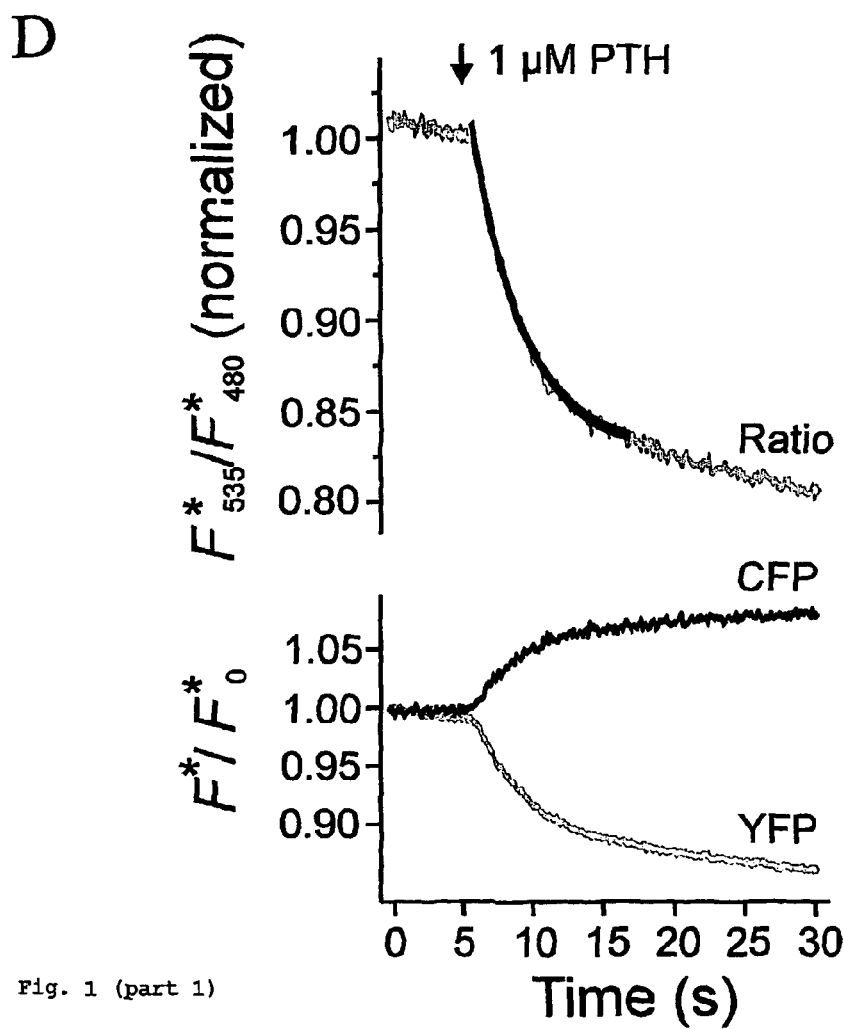
Fig. 1 (part 1)

Figure 1 part 2
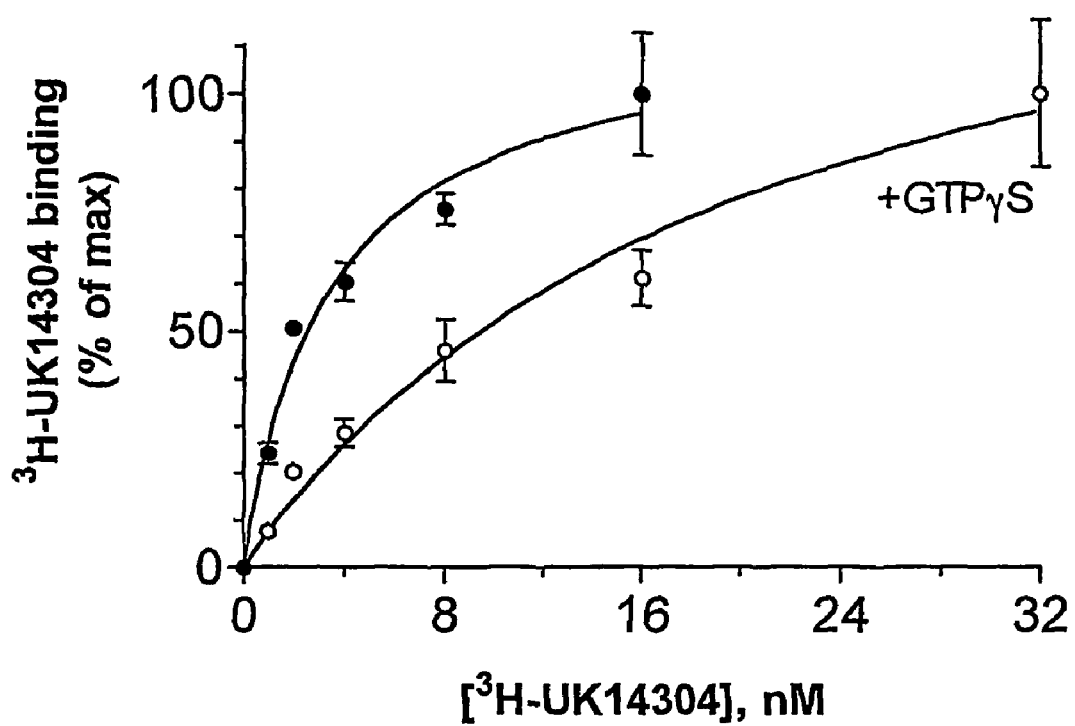

Fig. 2
A
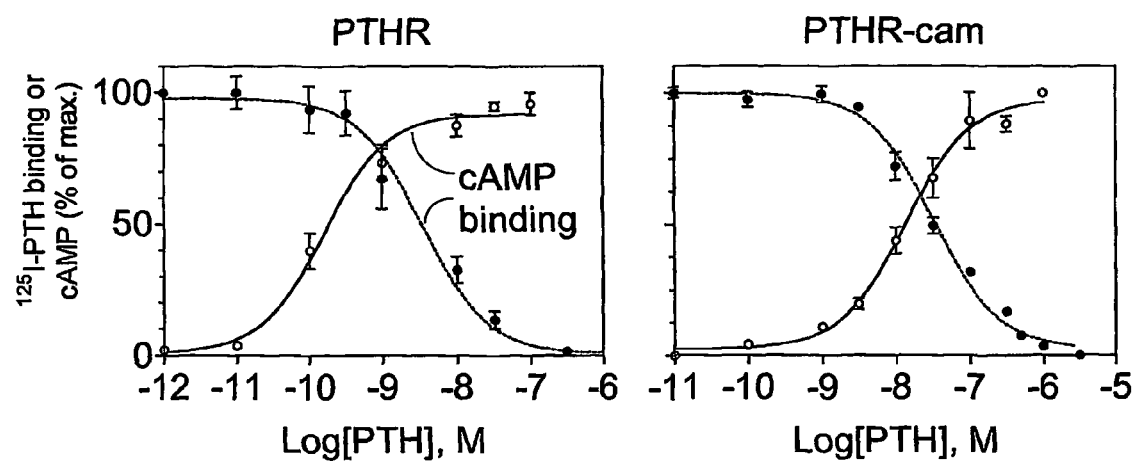
B
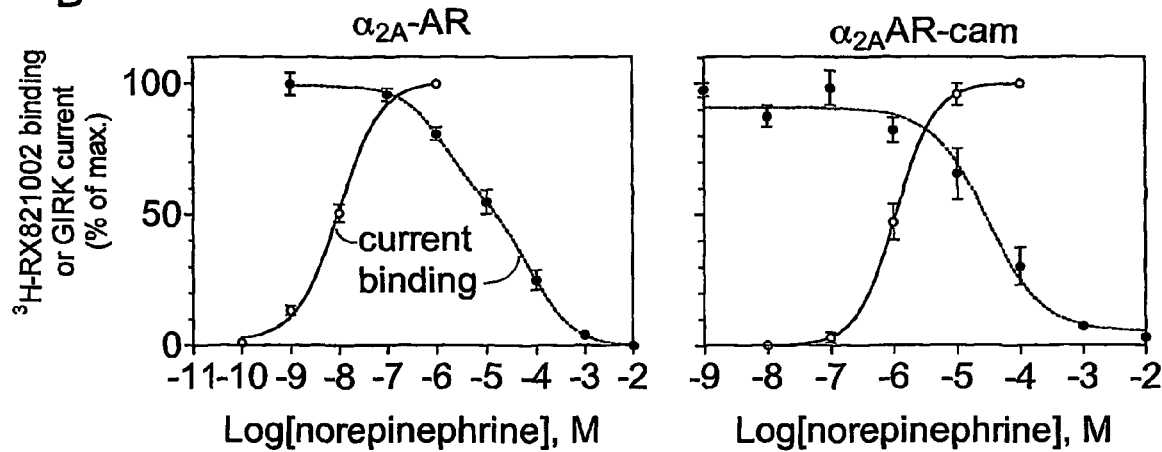
C
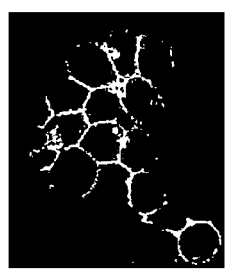

Figure 8:A
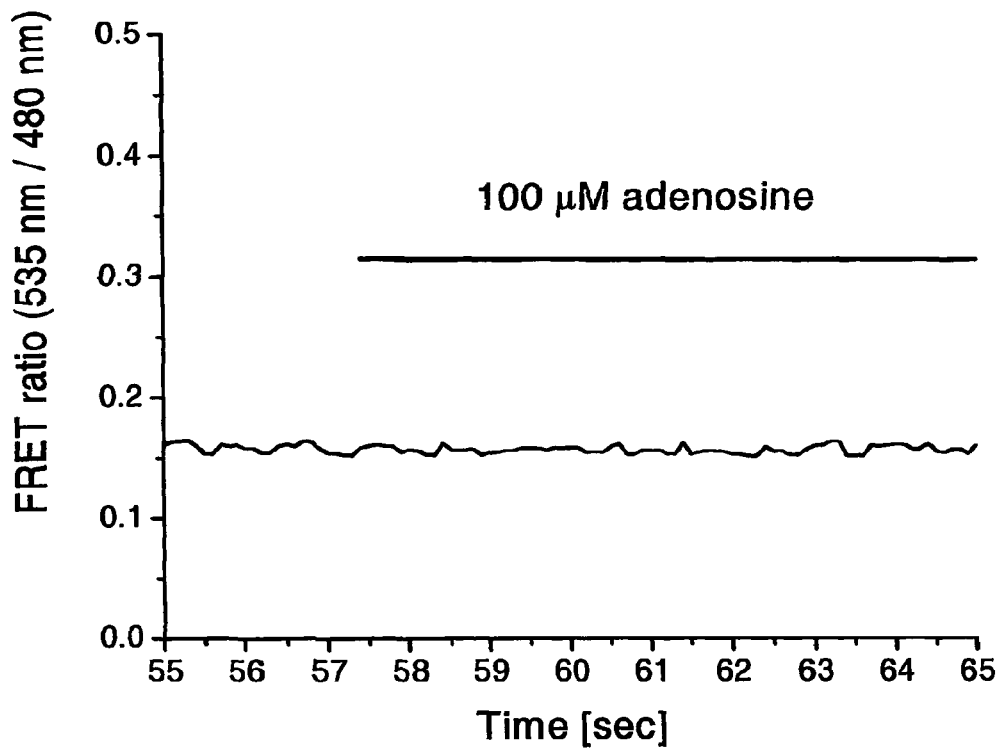
Figure 8B
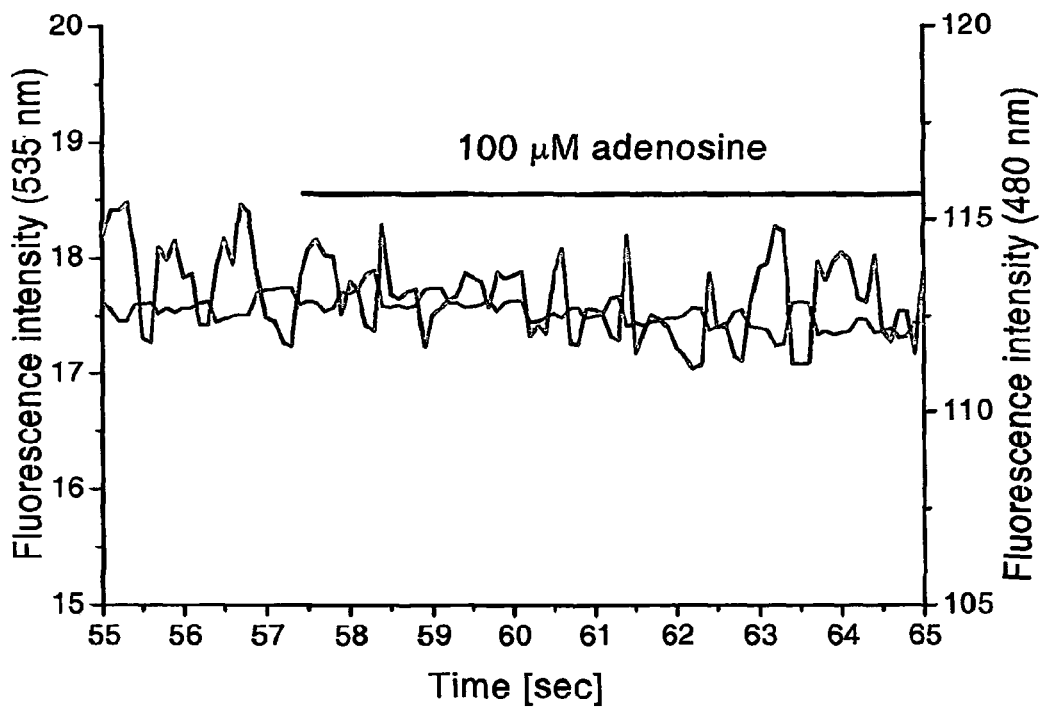

A

| Construct | KD-value for [³H]-NECA binding [nM] |
|---|---|
| A2A wild-type | 52.0 ± 8.9 |
| A2A-CFP-ModelPG-C49 | 55.9 ± 10.9 |
| A2A-FlashPG-CFP-C49 | 63.2 ± 11.2 |
| A2A-FlashPG-CFP-C33 | 38.9 ± 9.2 |
| A2A-„chameleon" | 63.1 ± 18.6 |

B

SEQUENCE LISTING

<160> NUMBER OF SEQ ID NOS: 46

<210> SEQ ID NO 1
<211> LENGTH: 1409
<212> TYPE: DNA
<213> ORGANISM: Mouse

<400> SEQUENCE: 1

-continued

```
atgggctacc catacgacgt cccagactac gccagcatgg gctcactgca gccggatgcc      60
ggcaacagca gctggaacgg gaccgaagcg cccggaggcg gcacccgagc accccttac     120
tccctgcagg tgacactgac gctggtttgc ctggctggcc tgctcatgct gttcacagta    180
tttggcaacg tgctggttat tatcgcggtg ttcaccagtc gcgcgctcaa agctccccaa    240
aacctcttcc tggtgtccct ggcctcagcg gacatcctgg tggccacgct ggtcattccc    300
ttttctttgg ccaacgaggt tatggggtac tggtactttg gtaaggtgtg gtgtgagatc    360
tatttggctc tcgacgtgct cttttgcacg tcgtccatag tgcacctgtg cgccatcagc    420
cttgaccgct actggtccat cacgcaggcc atcgagtaca acctgaagcg cacgccgcgt    480
cgcatcaagg ccatcattgt caccgtgtgg gtcatctcgg ctgtcatctc cttcccgcca    540
ctcatctcca tagagaagaa gaccagaagt ggtatgtcat ctcctcgtcc atcggttcct    600
tcttcgcgcc ttgcctcatc atgatcctgg tctacgtgcg tatttaccag atcgccaagc    660
gtcgcacccg cgtgcctccc agccgccggg gtccggacgc ctgttccgcg ccgccggggg    720
gcgccgatcg caggcccaac gggctgggcc cggagcgcgg cgcgggtccc acgggcgctg    780
aggcggagcc gctgcccacc cagcttaacg gtgccccggg ggagcccgcg cccgccgggc    840
cccgcgatgg ggatgcgctg gacctagagg agagttcgtc gtccgagcac gccgagcggc    900
ccccgggggcc ccgcagaccc gaccgcgcgcc cccgagccaa gggcaagacc cgggcgagtc    960
aggtgaagcc gggggacagt ctgccgcggc gcgggcccgg ggccgcgggg ccgggggctt   1020
cggggtccgg gcacggagag gagcgcggcg ggggcgccaa agcgtcgcgc tggcgcggga   1080
ggcaaaaccg ggagaaacgc ttcacgttcg tgctggcggt ggtgatcggc gtgttcgtgg   1140
tgtgttggtt tccgttcttt ttcacctaca cgctcatagc ggtcggctgc ccggtgccca   1200
gccagctctt caacttcttc ttctggttcg gctactgcaa cagctcgctg aaccctgtta   1260
tctacaccat cttcaaccac gacttccgac gcgccttcaa gaagatcctc tgccgtgggg   1320
acagaaaacg catcgtgtga ttcaaccacg acttccgacg cgccttcaag aagatcctct   1380
gccgtgggga cagaaaacgc atcgtgtga                                     1409
```

<210> SEQ ID NO 2
<211> LENGTH: 462
<212> TYPE: PRT
<213> ORGANISM: Mouse

<400> SEQUENCE: 2

```
Met Gly Tyr Pro Tyr Asp Val Pro Asp Tyr Ala Ser Met Gly Ser Leu
1               5                   10                  15

Gln Pro Asp Ala Gly Asn Ser Ser Trp Asn Gly Thr Glu Ala Pro Gly
            20                  25                  30

Gly Gly Thr Arg Ala Thr Pro Tyr Ser Leu Gln Val Thr Leu Thr Leu
        35                  40                  45

Val Cys Leu Ala Gly Leu Leu Met Leu Phe Thr Val Phe Gly Asn Val
    50                  55                  60

Leu Val Ile Ile Ala Val Phe Thr Ser Arg Ala Leu Lys Ala Pro Gln
65                  70                  75                  80

Asn Leu Phe Leu Val Ser Leu Ala Ser Ala Asp Ile Leu Val Ala Thr
                85                  90                  95

Leu Val Ile Pro Phe Ser Leu Ala Asn Glu Val Met Gly Tyr Trp Tyr
            100                 105                 110

Phe Gly Lys Val Trp Cys Glu Ile Tyr Leu Ala Leu Asp Val Leu Phe
        115                 120                 125
```

-continued

| | | | | | | | | | | | |
|---|---|---|---|---|---|---|---|---|---|---|---|
| Cys | Thr | Ser | Ser | Ile | Val | His | Leu | Cys | Ala | Ile | Ser | Leu | Asp | Arg | Tyr |
| 130 | | | | | 135 | | | | | 140 | |

Cys Thr Ser Ser Ile Val His Leu Cys Ala Ile Ser Leu Asp Arg Tyr
130                     135                     140

Trp Ser Ile Thr Gln Ala Ile Glu Tyr Asn Leu Lys Arg Thr Pro Arg
145                     150                     155                     160

Arg Ile Lys Ala Ile Ile Val Thr Val Trp Val Ile Ser Ala Val Ile
                        165                     170                     175

Ser Phe Pro Pro Leu Ile Ser Ile Glu Lys Lys Gly Ala Gly Gly Gly
                180                     185                     190

Gln Gln Pro Ala Glu Pro Ser Cys Lys Ile Asn Asp Gln Lys Trp Tyr
                195                     200                     205

Val Ile Ser Ser Ser Ile Gly Ser Phe Phe Ala Pro Cys Leu Ile Met
210                     215                     220

Ile Leu Val Tyr Val Arg Ile Tyr Gln Ile Ala Lys Arg Arg Thr Arg
225                     230                     235                     240

Val Pro Pro Ser Arg Arg Gly Pro Asp Ala Cys Ser Ala Pro Pro Gly
                        245                     250                     255

Gly Ala Asp Arg Arg Pro Asn Gly Leu Gly Pro Glu Arg Gly Ala Gly
                260                     265                     270

Pro Thr Gly Ala Glu Ala Glu Pro Leu Pro Thr Gln Leu Asn Gly Ala
                275                     280                     285

Pro Gly Glu Pro Ala Pro Ala Gly Pro Arg Asp Gly Asp Ala Leu Asp
290                     295                     300

Leu Glu Glu Ser Ser Ser Ser Glu His Ala Glu Arg Pro Pro Gly Pro
305                     310                     315                     320

Arg Arg Pro Asp Arg Gly Pro Arg Ala Lys Gly Lys Thr Arg Ala Ser
                        325                     330                     335

Gln Val Lys Pro Gly Asp Ser Leu Pro Arg Arg Gly Pro Gly Ala Ala
                340                     345                     350

Gly Pro Gly Ala Ser Gly Ser Gly His Gly Glu Glu Arg Gly Gly Gly
                355                     360                     365

Ala Lys Ala Ser Arg Trp Arg Gly Arg Gln Asn Arg Glu Lys Arg Phe
                370                     375                     380

Thr Phe Val Leu Ala Val Val Ile Gly Val Phe Val Val Cys Trp Phe
385                     390                     395                     400

Pro Phe Phe Phe Thr Tyr Thr Leu Ile Ala Val Gly Cys Pro Val Pro
                        405                     410                     415

Ser Gln Leu Phe Asn Phe Phe Phe Trp Phe Gly Tyr Cys Asn Ser Ser
                420                     425                     430

Leu Asn Pro Val Ile Tyr Thr Ile Phe Asn His Asp Phe Arg Arg Ala
                435                     440                     445

Phe Lys Lys Ile Leu Cys Arg Gly Asp Arg Lys Arg Ile Val
450                     455                     460

<210> SEQ ID NO 3
<211> LENGTH: 1785
<212> TYPE: DNA
<213> ORGANISM: homo sapiens

<400> SEQUENCE: 3
atggggaccg cccggatcgc acccggcctg gcgctcctgc tctgctgccc cgtgctcagc    60
tccgcgtacg cgctggtgga tgcagatgac gtcatgacta agaggaaca gatcttcctg   120 ctgcaccgtg tcaggcccca gtgcgaaaaa cggctcaagg aggtcctgca gaggccagcc   180
agcataatgg aatcagacaa gggatggaca tctgcgtcca catcagggaa gcccaggaaa   240
gataaggcat ctgggaagct ctaccctgag tctgaggagg acaaggaggc acccactggc   300

```
agcaggtacc gagggcgccc ctgtctgccg gaatgggacc acatcctgtg ctggccgctg    360
ggggcaccag gtgaggtggt ggctgtgccc tgtccggact acatttatga cttcaatcac    420
aaaggccatg cctaccgacg ctgtgaccgc aatggcagct gggagctggt gcctgggcac    480
aacaggacgt gggccaacta cagcgagtgt gtcaaatttc tcaccaatga gactcgtgaa    540
cgggaggtgt ttgaccgcct gggcatgatt tacaccgtgg gctactccgt gtccctggcg    600
tccctcaccg tagctgtgct catcctggcc tactttaggc ggctgcactg cacgcgcaac    660
tacatccaca tgcacctgtt cctgtccttc atgctgcgcg ccgtgagcat cttcgtcaag    720
gacgctgtgc tctactctgg cgccacgctt gatgaggctg agcgcctcac cgaggaggag    780
ctgcgcgcca tcgcccaggc gccccgccg cctgccaccg ccgctgccgg ctacgcgggc    840
tgcagggtgg ctgtgacctt cttcctttac ttcctggcca ccaactacta ctggattctg    900
gtggaggggc tgtacctgca cagcctcatc ttcatggcct tcttctcaga gaagaagtac    960
ctgtggggct tcacagtctt cggctggggt ctgcccgctg tcttcgtggc tgtgtgggtc   1020
agtgtcagag ctaccctggc caacaccggg tgctgggact tgagctccgg aacaaaaag   1080
tggatcatcc aggtgcccat cctggcctcc attgtgctca acttcatcct cttcatcaat   1140
atcgtccggg tgctcgccac caagctgcgg gagaccaacg ccggccggtg tgacacacgg   1200
cagcagtacc ggaagctgct caaatccacg ctggtgctca tgccctctt tggcgtccac   1260
tacattgtct tcatggccac accatacacc gaggtctcag ggacgctctg gcaagtccag   1320
atgcactatg agatgctctt caactccttc cagggatttt ttgtcgcaat catatactgt   1380
ttctgcaatg gcgaggtaca agctgagatc aagaaatctt ggagccgctg gacactggca   1440
ctggacttca gcgaaaggc acgcagcggg agcagcagct atagctacgg ccccatggtg   1500
tcccacacaa gtgtgaccaa tgtcggcccc cgtgtgggac tcggcctgcc cctcagcccc   1560
cgcctactgc ccactgccac caccaacggc caccctcagc tgcctggcca tgccaagcca   1620
gggaccccag ccctggagac cctcgagacc acaccacctg ccatggctgc tcccaaggac   1680
gatgggttcc tcaacggctc ctgctcaggc ctggacgagg aggcctctgg gcctgagcgg   1740
ccacctgccc tgctacagga agagtgggag acagtcatgt gatga                   1785
```

<210> SEQ ID NO 4  
<211> LENGTH: 593  
<212> TYPE: PRT  
<213> ORGANISM: homo sapiens

<400> SEQUENCE: 4

```
Met Gly Thr Ala Arg Ile Ala Pro Gly Leu Ala Leu Leu Cys Cys
1               5                   10                  15

Pro Val Leu Ser Ser Ala Tyr Ala Leu Val Asp Ala Asp Val Met
                20                  25                  30

Thr Lys Glu Glu Gln Ile Phe Leu Leu His Arg Ala Gln Ala Gln Cys
            35                  40                  45

Glu Lys Arg Leu Lys Glu Val Leu Gln Arg Pro Ala Ser Ile Met Glu
        50                  55                  60

Ser Asp Lys Gly Trp Thr Ser Ala Ser Thr Ser Gly Lys Pro Arg Lys
65                  70                  75                  80

Asp Lys Ala Ser Gly Lys Leu Tyr Pro Glu Ser Glu Glu Asp Lys Glu
                85                  90                  95

Ala Pro Thr Gly Ser Arg Tyr Arg Gly Arg Pro Cys Leu Pro Glu Trp
            100                 105                 110
```

```
Asp His Ile Leu Cys Trp Pro Leu Gly Ala Pro Gly Glu Val Val Ala
        115                 120                 125
Val Pro Cys Pro Asp Tyr Ile Tyr Asp Phe Asn His Lys Gly His Ala
130                 135                 140
Tyr Arg Arg Cys Asp Arg Asn Gly Ser Trp Glu Leu Val Pro Gly His
145                 150                 155                 160
Asn Arg Thr Trp Ala Asn Tyr Ser Glu Cys Val Lys Phe Leu Thr Asn
                165                 170                 175
Glu Thr Arg Glu Arg Glu Val Phe Asp Arg Leu Gly Met Ile Tyr Thr
            180                 185                 190
Val Gly Tyr Ser Val Ser Leu Ala Ser Leu Thr Val Ala Val Leu Ile
        195                 200                 205
Leu Ala Tyr Phe Arg Arg Leu His Cys Thr Arg Asn Tyr Ile His Met
210                 215                 220
His Leu Phe Leu Ser Phe Met Leu Arg Ala Val Ser Ile Phe Val Lys
225                 230                 235                 240
Asp Ala Val Leu Tyr Ser Gly Ala Thr Leu Asp Glu Ala Glu Arg Leu
                245                 250                 255
Thr Glu Glu Leu Arg Ala Ile Ala Gln Ala Pro Pro Pro Ala
            260                 265                 270
Thr Ala Ala Gly Tyr Ala Gly Cys Arg Val Ala Val Thr Phe Phe
        275                 280                 285
Leu Tyr Phe Leu Ala Thr Asn Tyr Tyr Trp Ile Leu Val Glu Gly Leu
290                 295                 300
Tyr Leu His Ser Leu Ile Phe Met Ala Phe Phe Ser Glu Lys Lys Tyr
305                 310                 315                 320
Leu Trp Gly Phe Thr Val Phe Gly Trp Gly Leu Pro Ala Val Phe Val
                325                 330                 335
Ala Val Trp Val Ser Val Arg Ala Thr Leu Ala Asn Thr Gly Cys Trp
            340                 345                 350
Asp Leu Ser Ser Gly Asn Lys Lys Trp Ile Ile Gln Val Pro Ile Leu
        355                 360                 365
Ala Ser Ile Val Leu Asn Phe Ile Leu Phe Ile Asn Ile Val Arg Val
370                 375                 380
Leu Ala Thr Lys Leu Arg Glu Thr Asn Ala Gly Arg Cys Asp Thr Arg
385                 390                 395                 400
Gln Gln Tyr Arg Lys Leu Leu Lys Ser Thr Leu Val Leu Met Pro Leu
                405                 410                 415
Phe Gly Val His Tyr Ile Val Phe Met Ala Thr Pro Tyr Thr Glu Val
            420                 425                 430
Ser Gly Thr Leu Trp Gln Val Gln Met His Tyr Glu Met Leu Phe Asn
        435                 440                 445
Ser Phe Gln Gly Phe Phe Val Ala Ile Ile Tyr Cys Phe Cys Asn Gly
450                 455                 460
Glu Val Gln Ala Glu Ile Lys Lys Ser Trp Ser Arg Trp Thr Leu Ala
465                 470                 475                 480
Leu Asp Phe Lys Arg Lys Ala Arg Ser Gly Ser Ser Ser Tyr Ser Tyr
                485                 490                 495
Gly Pro Met Val Ser His Thr Ser Val Thr Asn Val Gly Pro Arg Val
            500                 505                 510
Gly Leu Gly Leu Pro Leu Ser Pro Arg Leu Leu Pro Thr Ala Thr Thr
        515                 520                 525
Asn Gly His Pro Gln Leu Pro Gly His Ala Lys Pro Gly Thr Pro Ala
530                 535                 540
```

```
Leu Glu Thr Leu Glu Thr Thr Pro Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
            580                 585                 590

Met

<210> SEQ ID NO 5
<211> LENGTH: 1238
<212> TYPE: DNA
<213> ORGANISM: homo sapiens

<400> SEQUENCE: 5
atgcccatca tgggctcctc ggtgtacatc acggtggagc tggccattgc tgtgctggcc      60
atcctgggca atgtgctggt gtgctgggcc gtgtggctca acagcaacct gcagaacgtc     120
accaactact tgtggtgtc actggcggcg gccgacatcg cagtgggtgt gctcgccatc      180 cccttttgcca tcaccatcag caccgggttc tgcgctgcct gccacggctg cctcttcatt     240
gcctgcttcg tcctggtcct cacgcagagc tccatcttca gtctcctggc catgccatt     300 gaccgctaca ttgccatccg catcccgctc cggtacaatg gcttggtgac cggcacgagg     360
gctaagggca tcattgccat ctgctgggtg ctgtcgtttg ccatcggcct gactcccatg     420
ctaggttgga caactgcggt tcagccaaag gagggcaaga accactccca gggctgcggg     480
gagggccaag tggcctgtct cttgaggat gtggtcccca tgaactacat ggtgtacttc     540
aacttctttc ctgtgtgctg gtgccccctgc tgctcatgct gggtgtctat ttgcggatct     600
tcctggcggc gcgacgacag ctgaagcaga tggagagcca gcctctgccg ggggagcggg     660
cacggtccac actgcagaag gaggtccatg ctgccaagtc actggccatc attgtggggc     720
tctttgccct ctgctggctg ccctacacaa tcatcaactg cttcactttc ttctgccccg     780
actgcagcca cgcccctcc tggctcatgt acctggccat cgtcctctcc cacaccaatt     840
cggttgtgaa tccttcatc tacgcctacc gtatccgcga gttccgccag accttccgca     900
agatcattcg cagccacgtc ctgaggcagc aagaaccttt caaggcagct ggcaccagtg     960
cccgggtctt ggcagctcat ggcagtgacg gagagcaggt cagcctccgt ctcaacggcc    1020
acccgccagg agtgtgggcc aacggcagtg ctccccaccc tgagcggagg cccaatggct    1080
atgccctggg gctggtgagt ggaggagtg cccaagagtc ccaggggaac acgggcctcc    1140
cagacgtgga gctccttagc catgagctca agggagtgtg cccagagccc cctggcctag    1200
atgaccccct ggcccaggat ggagcaggag tgtcctga                            1238

<210> SEQ ID NO 6
<211> LENGTH: 391
<212> TYPE: PRT
<213> ORGANISM: homo sapiens

<400> SEQUENCE: 6

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
                20                  25                  30

Leu Asn Ser Asn Leu Gln Asn Val Thr Asn Tyr Phe Val Ser Leu Ala
            35                  40                  45

Ala Ala Asp Ile Ala Val Gly Val Leu Ala Ile Pro Phe Ala Ile Thr
```

| | | | | | | | | | | | |
|---|---|---|---|---|---|---|---|---|---|---|---|
| | | 50 | | | | 55 | | | | 60 | |
| Ile | Ser | Thr | Gly | Phe | Cys | Ala | Ala | Cys | His | Gly | Cys | Leu | Phe | Ile | Ala |
| 65 | | | | 70 | | | | 75 | | | | 80 |

Ile Ser Thr Gly Phe Cys Ala Ala Cys His Gly Cys Leu Phe Ile Ala
65            70            75            80

Cys Phe Val Leu Val Leu Thr Gln Ser Ser Ile Phe Ser Leu Leu Ala
           85           90           95

Ile Ala Ile Asp Arg Tyr Ile Ala Ile Arg Ile Pro Leu Arg Tyr Asn
        100         105         110

Gly Leu Val Thr Gly Thr Arg Ala Lys Gly Ile Ile Ala Ile Cys Trp
    115          120          125

Val Leu Ser Phe Ala Ile Gly Leu Thr Pro Met Leu Gly Trp Asn Asn
130           135           140

Cys Gly Gln Pro Lys Glu Gly Lys Asn His Ser Gln Gly Cys Gly Glu
145          150          155          160

Gly Gln Val Ala Cys Leu Phe Glu Asp Val Val Pro Met Asn Tyr Met
         165         170         175

Val Tyr Phe Asn Phe Phe Ala Cys Val Leu Val Pro Leu Leu Leu Met
        180         185         190

Leu Gly Val Tyr Leu Arg Ile Phe Leu Ala Ala Arg Arg Gln Leu Lys
    195          200          205

Gln Met Glu Ser Gln Pro Leu Pro Gly Glu Arg Ala Arg Ser Thr Leu
210          215          220

Gln Lys Glu Val His Ala Ala Lys Ser Leu Ala Ile Ile Val Gly Leu
225          230          235          240

Phe Ala Leu Cys Trp Leu Pro Leu His Ile Ile Asn Cys Phe Thr Phe
        245         250         255

Phe Cys Pro Asp Cys Ser His Ala Pro Leu Trp Leu Met Tyr Leu Ala
    260          265          270

Ile Val Leu Ser His Thr Asn Ser Val Val Asn Pro Phe Ile Tyr Ala
275          280          285

Tyr Arg Ile Arg Glu Phe Arg Gln Thr Phe Arg Lys Ile Ile Arg Ser
    290          295          300

His Val Leu Arg Gln Gln Glu Pro Phe Lys Ala Ala Gly Thr Ser Ala
305          310          315          320

Arg Val Leu Ala Ala His Gly Ser Asp Gly Glu Gln Val Ser Leu Arg
        325         330         335

Leu Asn Gly His Pro Pro Gly Val Trp Ala Asn Gly Ser Ala Pro His
    340          345          350

Pro Glu Arg Arg Pro Asn Gly Tyr Ala Leu Gly Leu Val Ser Gly Gly
        355         360         365

Ser Ala Gln Glu Ser Gln Gly Asn Thr Gly Leu Pro Asp Val Glu Leu
370          375          380

Leu Ser His Glu Leu Lys Gly
385          390

<210> SEQ ID NO 7
<211> LENGTH: 720
<212> TYPE: DNA
<213> ORGANISM: artificial sequence
<220> FEATURE:
<223> OTHER INFORMATION: eCFP (enhanced CFP) cDNA sequence

<400> SEQUENCE: 7
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180

```
ctcgtgacca ccctgacctg gggcgtgcag tgcttcagcc gctacccga ccacatgaag    240 cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 8
<211> LENGTH: 239
<212> TYPE: PRT
<213> ORGANISM: artificial sequence
<220> FEATURE:
<223> OTHER INFORMATION: eCFP (enhanced CFP) amino acid sequence
<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 9
<211> LENGTH: 720
<212> TYPE: DNA
<213> ORGANISM: artificial sequence
<220> FEATURE:

<223> OTHER INFORMATION: YFP cDNA sequence

<400> SEQUENCE: 9

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccttcggcta cggcctgcag tgcttcgccc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagct accagtccgc cctgagcaaa gaccccaacg agaagcgcga tcacatggtc   660
ctgctggagt tcgtgaccgc cgccgggatc actctcggca tggacgagct gtacaagtaa   720
```

<210> SEQ ID NO 10
<211> LENGTH: 239
<212> TYPE: PRT
<213> ORGANISM: artificial sequence
<220> FEATURE:
<223> OTHER INFORMATION: YFP amino acid sequence

<400> SEQUENCE: 10

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220
```

```
Val Thr Ala Ala Gly Ile Thr Leu Gly Met Asp Glu Leu Tyr Lys
225                 230                 235
```

<210> SEQ ID NO 11
<211> LENGTH: 2457
<212> TYPE: DNA
<213> ORGANISM: artificial sequence
<220> FEATURE:
<223> OTHER INFORMATION: alpha2a adrenergic receptor-cam cDNA sequence

<400> SEQUENCE: 11

| | | | | | |
|---|---|---|---|---|---|
| atgggctacc | catacgacgt | cccagactac | gccagcatgg | gctcactgca | gccggatgcc | 60 |
| ggcaacagca | gctggaacgg | gaccgaagcg | cccggaggcg | gcacccgagc | cacccettac | 120 |
| tccctgcagg | tgacactgac | gctggtttgc | ctggctggcc | tgctcatgct | gttcacagta | 180 |
| tttggcaacg | tgctggttat | tatcgcggtg | ttcaccagtc | gcgcgctcaa | agctccccaa | 240 |
| aacctcttcc | tggtgtccct | ggcctcagcg | gacatcctgg | tggccacgct | ggtcattccc | 300 |
| ttttctttgg | ccaacgaggt | tatgggttac | tggtactttg | gtaaggtgtg | gtgtgagatc | 360 |
| tatttggctc | tcgacgtgct | cttttgcacg | tcgtccatag | tgcacctgtg | cgccatcagc | 420 |
| cttgaccgct | actggtccat | cacgcaggcc | atcgagtaca | acctgaagcg | cacgccgcgt | 480 |
| cgcatcaagg | ccatcattgt | caccgtgtgg | gtcatctcgg | ctgtcatctc | cttcccgcca | 540 |
| ctcatctcca | tagagaagaa | gggcgctggc | ggcgggcagc | agccggccga | gccaagctgc | 600 |
| aagatcaacg | accagaagtg | gtatgtcatc | tcctcgtcca | tcggttcctt | cttcgcgcct | 660 |
| tgcctcatca | tgatcctggt | ctacgtgcgt | atttaccaga | tcgccaagcg | tcgcacccgc | 720 |
| gtgcctccca | gccgccgggg | tccggacgcc | atggtgagca | agggcgagga | gctgttcacc | 780 |
| ggggtggtgc | ccatcctggt | cgagctggac | ggcgacgtaa | acggccacaa | gttcagcgtg | 840 |
| tccggcgagg | gcgagggcga | tgccacctac | ggcaagctga | ccctgaagtt | catctgcacc | 900 |
| accggcaagc | tgcccgtgcc | ctggcccacc | ctcgtgacca | ccttcggcta | cggcctgcag | 960 |
| tgcttcgccc | gctaccccga | ccacatgaag | cagcacgact | tcttcaagtc | cgccatgccc | 1020 |
| gaaggctacg | tccaggagcg | caccatcttc | ttcaaggacg | acggcaacta | caagacccgc | 1080 |
| gccgaggtga | agttcgaggg | cgacaccctg | gtgaaccgca | tcgagctgaa | gggcatcgac | 1140 |
| ttcaaggagg | acggcaacat | cctggggcac | aagctggagt | acaactacaa | cagccacaac | 1200 |
| gtctatatca | tggccgacaa | gcagaagaac | ggcatcaagg | tgaacttcaa | gatccgccac | 1260 |
| aacatcgagg | acggcagcgt | gcagctcgcc | gaccactacc | agcagaacac | ccccatcggc | 1320 |
| gacggccccg | tgctgctgcc | cgacaaccac | tacctgagct | accagtccgc | cctgagcaaa | 1380 |
| gaccccaacg | agaagcgcga | tcacatggtc | ctgctggagt | tcgtgaccgc | cgccgggatc | 1440 |
| actctcggca | tggacgagct | gtacaagcgc | tggcgcggga | ggcaaaaccg | ggagaaacgc | 1500 |
| ttcacgttcg | tgctggcggt | ggtgatcggc | gtgttcgtgg | tgtgttggtt | tccgttctt | 1560 |
| ttcacctaca | cgctcatagc | ggtcggctgc | ccggtgccca | gccagctctt | caacttcttc | 1620 |
| ttctggttcg | gctactgcaa | cagctcgctg | aaccctgtta | tctacaccat | cttcaaccac | 1680 |
| gacttccgac | gcgccttcaa | gaagatcctc | tgccgtgggg | acagaaaacg | catcgtgatg | 1740 |
| gtgagcaagg | gcgaggagct | gttcaccggg | gtggtgccca | tcctggtcga | gctggacggc | 1800 |
| gacgtaaacg | gccacaagtt | cagcgtgtcc | ggcgagggcg | agggcgatgc | cacctacggc | 1860 |
| aagctgaccc | tgaagttcat | ctgcaccacc | ggcaagctgc | ccgtgccctg | gcccaccctc | 1920 |
| gtgaccaccc | tgacctgggg | cgtgcagtgc | ttcagccgct | accccgacca | catgaagcag | 1980 |
| cacgacttct | tcaagtccgc | catgcccgaa | ggctacgtcc | aggagcgcac | catcttcttc | 2040 |

```
aaggacgacg gcaactacaa gacccgcgcc gaggtgaagt tcgagggcga cacccctggtg      2100 aaccgcatcg agctgaaggg catcgacttc aaggaggacg gcaacatcct ggggcacaag      2160
ctggagtaca actacatcag ccacaacgtc tatatcaccg ccgacaagca gaagaacggc      2220
atcaaggcca acttcaagat ccgccacaac atcgaggacg gcagcgtgca gctcgccgac      2280
cactaccagc agaacacccc catcggcgac ggccccgtgc tgctgcccga caaccactac      2340
ctgagcaccc agtccgccct gagcaaagac cccaacgaga gcgcgatca catggtcctg       2400 ctggagttcg tgaccgccgc cgggatcact ctcggcatgg acgagctgta caagtaa         2457
```

<210> SEQ ID NO 12
<211> LENGTH: 818
<212> TYPE: PRT
<213> ORGANISM: artificial sequence
<220> FEATURE:
<223> OTHER INFORMATION: alpha 2a adrenergic receptor-cam "chameleon" amino acid sequence
<400> SEQUENCE: 12

```
Met Gly Tyr Pro Tyr Asp Val Pro Asp Tyr Ala Ser Met Gly Ser Leu
1               5                   10                  15

Gln Pro Asp Ala Gly Asn Ser Ser Trp Asn Gly Thr Glu Ala Pro Gly
            20                  25                  30

Gly Gly Thr Arg Ala Thr Pro Tyr Ser Leu Gln Val Thr Leu Thr Leu
        35                  40                  45

Val Cys Leu Ala Gly Leu Leu Met Leu Phe Thr Val Phe Gly Asn Val
    50                  55                  60

Leu Val Ile Ile Ala Val Phe Thr Ser Arg Ala Leu Lys Ala Pro Gln
65                  70                  75                  80

Asn Leu Phe Leu Val Ser Leu Ala Ser Ala Asp Ile Leu Val Ala Thr
                85                  90                  95

Leu Val Ile Pro Phe Ser Leu Ala Asn Glu Val Met Gly Tyr Trp Tyr
            100                 105                 110

Phe Gly Lys Val Trp Cys Glu Ile Tyr Leu Ala Leu Asp Val Leu Phe
        115                 120                 125

Cys Thr Ser Ser Ile Val His Leu Cys Ala Ile Ser Leu Asp Arg Tyr
    130                 135                 140

Trp Ser Ile Thr Gln Ala Ile Glu Tyr Asn Leu Lys Arg Thr Pro Arg
145                 150                 155                 160

Arg Ile Lys Ala Ile Ile Val Thr Val Trp Val Ile Ser Ala Val Ile
                165                 170                 175

Ser Phe Pro Pro Leu Ile Ser Ile Glu Lys Lys Gly Ala Gly Gly Gly
            180                 185                 190

Gln Gln Pro Ala Glu Pro Ser Cys Lys Ile Asn Asp Gln Lys Trp Tyr
        195                 200                 205

Val Ile Ser Ser Ser Ile Gly Ser Phe Phe Ala Pro Cys Leu Ile Met
    210                 215                 220

Ile Leu Val Tyr Val Arg Ile Tyr Gln Ile Ala Lys Arg Arg Thr Arg
225                 230                 235                 240

Val Pro Pro Ser Arg Arg Gly Pro Asp Ala Met Val Ser Lys Gly Glu
                245                 250                 255

Glu Leu Phe Thr Gly Val Val Pro Ile Leu Val Glu Leu Asp Gly Asp
            260                 265                 270

Val Asn Gly His Lys Phe Ser Val Ser Gly Glu Gly Glu Gly Asp Ala
        275                 280                 285
```

```
Thr Tyr Gly Lys Leu Thr Leu Lys Phe Ile Cys Thr Thr Gly Lys Leu
        290                 295                 300

Pro Val Pro Trp Pro Thr Leu Val Thr Thr Phe Gly Tyr Gly Leu Gln
305                 310                 315                 320

Cys Phe Ala Arg Tyr Pro Asp His Met Lys Gln His Asp Phe Phe Lys
                325                 330                 335

Ser Ala Met Pro Glu Gly Tyr Val Gln Glu Arg Thr Ile Phe Phe Lys
                340                 345                 350

Asp Asp Gly Asn Tyr Lys Thr Arg Ala Glu Val Lys Phe Glu Gly Asp
                355                 360                 365

Thr Leu Val Asn Arg Ile Glu Leu Lys Gly Ile Asp Phe Lys Glu Asp
        370                 375                 380

Gly Asn Ile Leu Gly His Lys Leu Glu Tyr Asn Tyr Asn Ser His Asn
385                 390                 395                 400

Val Tyr Ile Met Ala Asp Lys Gln Lys Asn Gly Ile Lys Val Asn Phe
                405                 410                 415

Lys Ile Arg His Asn Ile Glu Asp Gly Ser Val Gln Leu Ala Asp His
                420                 425                 430

Tyr Gln Gln Asn Thr Pro Ile Gly Asp Gly Pro Val Leu Leu Pro Asp
        435                 440                 445

Asn His Tyr Leu Ser Tyr Gln Ser Ala Leu Ser Lys Asp Pro Asn Glu
450                 455                 460

Lys Arg Asp His Met Val Leu Leu Glu Phe Val Thr Ala Ala Gly Ile
465                 470                 475                 480

Thr Leu Gly Met Asp Glu Leu Tyr Lys Arg Trp Arg Gly Arg Gln Asn
                485                 490                 495

Arg Glu Lys Arg Phe Thr Phe Val Leu Ala Val Val Ile Gly Val Phe
                500                 505                 510

Val Val Cys Trp Phe Pro Phe Phe Thr Tyr Thr Leu Ile Ala Val
                515                 520                 525

Gly Cys Pro Val Pro Ser Gln Leu Phe Asn Phe Phe Phe Trp Phe Gly
        530                 535                 540

Tyr Cys Asn Ser Ser Leu Asn Pro Val Ile Tyr Thr Ile Phe Asn His
545                 550                 555                 560

Asp Phe Arg Arg Ala Phe Lys Lys Ile Leu Cys Arg Gly Asp Arg Lys
                565                 570                 575

Arg Ile Val Met Val Ser Lys Gly Glu Glu Leu Phe Thr Gly Val Val
                580                 585                 590

Pro Ile Leu Val Glu Leu Asp Gly Asp Val Asn Gly His Lys Phe Ser
        595                 600                 605

Val Ser Gly Glu Gly Glu Gly Asp Ala Thr Tyr Gly Lys Leu Thr Leu
        610                 615                 620

Lys Phe Ile Cys Thr Thr Gly Lys Leu Pro Val Pro Trp Pro Thr Leu
625                 630                 635                 640

Val Thr Thr Leu Thr Trp Gly Val Gln Cys Phe Ser Arg Tyr Pro Asp
                645                 650                 655

His Met Lys Gln His Asp Phe Phe Lys Ser Ala Met Pro Glu Gly Tyr
                660                 665                 670

Val Gln Glu Arg Thr Ile Phe Phe Lys Asp Asp Gly Asn Tyr Lys Thr
                675                 680                 685

Arg Ala Glu Val Lys Phe Glu Gly Asp Thr Leu Val Asn Arg Ile Glu
        690                 695                 700

Leu Lys Gly Ile Asp Phe Lys Glu Asp Gly Asn Ile Leu Gly His Lys
705                 710                 715                 720
```

```
Leu Glu Tyr Asn Tyr Ile Ser His Asn Val Tyr Ile Thr Ala Asp Lys
            725                 730                 735

Gln Lys Asn Gly Ile Lys Ala Asn Phe Lys Ile Arg His Asn Ile Glu
        740                 745                 750

Asp Gly Ser Val Gln Leu Ala Asp His Tyr Gln Gln Asn Thr Pro Ile
            755                 760                 765

Gly Asp Gly Pro Val Leu Leu Pro Asp Asn His Tyr Leu Ser Thr Gln
    770                 775                 780

Ser Ala Leu Ser Lys Asp Pro Asn Glu Lys Arg Asp His Met Val Leu
785                 790                 795                 800

Leu Glu Phe Val Thr Ala Ala Gly Ile Thr Leu Gly Met Asp Glu Leu
                805                 810                 815

Tyr Lys

<210> SEQ ID NO 13
<211> LENGTH: 2928
<212> TYPE: DNA
<213> ORGANISM: artificial sequence
<220> FEATURE:
<223> OTHER INFORMATION: PTH receptor-cam "chameleon" 8 cDNA sequence

<400> SEQUENCE: 13
atggggaccg cccggatcgc acccggcctg gcgctcctgc tctgctgccc cgtgctcagc      60
tccgcgtacg cgctggtgga tgcagatgac gtcatgacta agaggaaca gatcttcctg     120 ctgcaccgtg tcaggcccca gtgcgaaaaa cggctcaagg aggtcctgca gaggccagcc     180
agcataatgg aatcagacaa gggatggaca tctgcgtcca catcagggaa gcccaggaaa     240
gataaggcat ctgggaagct ctaccctgag tctgaggagg acaaggaggc acccactggc     300
agcaggtacc gagggcgccc ctgtctgccg gaatgggacc acatcctgtg ctggccgctg     360
ggggcaccag gtgaggtggt ggctgtgccc tgtccggact acatttatga cttcaatcac     420
aaaggccatg cctaccgacg ctgtgaccgc aatggcagct gggagctggt gcctgggcac     480
aacaggacgt gggccaacta cagcgagtgt gtcaaatttc tcaccaatga gactcgtgaa     540
cgggaggtgt ttgaccgcct gggcatgatt tacaccgtgg gctactccgt gtccctggcg     600
tccctcaccg tagctgtgct catcctggcc tactttaggc ggctgcactg cacgcgcaac     660
tacatccaca tgcacctgtt cctgtccttc atgctgcgcg ccgtgagcat cttcgtcaag     720
gacgctgtgc tctactctgg cgccacgctt gatgaggctg agcgcctcac cgaggaggag     780
ctgcgcgcca tcgcccaggc gcccccgccg cctgccaccg ccgctgccgg ctacgcgggc     840
tgcagggtgg ctgtgacctt cttcctttac ttcctggcca ccaactacta ctggattctg     900 gtggagggc tgtacctgca cagcctcatc ttcatggcct tcttctcaga aagaagtac      960 ctgtggggct tcacagtctt cggctgggt ctgcccgctg tcttcgtggc tgtgtgggtc    1020
agtgtcagag ctaccctggc caacaccggg tgctgggact gagctccgg aacaaaaag    1080 tggatcatcc aggtgcccat cctggcctcc attgtgctca acttcatcct cttcatcaat    1140
atcgtccggg tgctcgccac caagctgcgg gagaccaacg ccggcatggt gagcaagggc    1200
gaggagctgt tcaccgggt ggtgcccatc ctggtcgagc tggacggcga cgtaaacggc    1260
cacaagttca gcgtgtccgg cgaggcgag ggcgatgcca cctacggcaa gctgaccctg    1320
aagttcatct gcaccaccgg caagctgccc gtgccctggc ccaccctcgt gaccaccctg    1380
acctggggcg tgcagtgctt cagccgctac cccgaccaca tgaagcagca cgacttcttc    1440
aagtccgcca tgcccgaagg ctacgtccag gagcgcacca tcttcttcaa ggacgacggc    1500
```

```
aactacaaga cccgcgccga ggtgaagttc gagggcgaca ccctggtgaa ccgcatcgag   1560
ctgaagggca tcgacttcaa ggaggacggc aacatcctgg gcacaagct ggagtacaac    1620 tacatcagcc acaacgtcta tatcaccgcc gacaagcaga agaacggcat caaggccaac   1680
ttcaagatcc gccacaacat cgaggacggc agcgtgcagc tcgccgacca ctaccagcag   1740
aacaccccca tcggcgacgg ccccgtgctg ctgcccgaca ccactacct gagcacccag    1800 tccgccctga gcaaagaccc caacgagaag cgcgatcaca tggtcctgct ggagttcgtg   1860
accgccgccg ggatcactct cggcatggac gagctgtaca gcggtgtga cacacggcag    1920 cagtaccgga agctgctcaa atccacgctg gtgctcatgc ccctctttgg cgtccactac   1980
attgtcttca tggccacacc atacaccgag gtctcaggga cgctctggca agtccagatg   2040
cactatgaga tgctcttcaa ctccttccag ggatttttg tcgcaatcat atactgtttc    2100
tgcaatggcg aggtacaagc tgagatcaag aaatcttgga ccgctggac actggcactg    2160 gacttcaagc gaaaggcacg cagcgggagc agcagctata gctacggcat ggtgagcaag   2220
ggcgaggagc tgttcaccgg ggtggtgccc atcctggtcg agctggacgg cgacgtaaac   2280
ggccacaagt tcagcgtgtc cggcgagggc gagggcgatg ccacctacgg caagctgacc   2340
ctgaagttca tctgcaccac cggcaagctg cccgtgccct ggcccaccct cgtgaccacc   2400
ttcggctacg gcctgcagtg cttcgcccgc tacccccgacc acatgaagca gcacgacttc   2460
ttcaagtccg ccatgcccga aggctacgtc caggagcgca ccatcttctt caaggacgac   2520
ggcaactaca gacccgcgc cgaggtgaag ttcgagggcg acaccctggt gaaccgcatc    2580
gagctgaagg gcatcgactt caaggaggac ggcaacatcc tggggcacaa gctggagtac   2640
aactacaaca gccacaacgt ctatatcatg gccgacaagc agaagaacgg catcaaggtg   2700
aacttcaaga tccgccacaa catcgaggac ggcagcgtgc agctcgccga ccactaccag   2760
cagaacaccc ccatcggcga cggccccgtg ctgctgcccg acaaccacta cctgagctac   2820
cagtccgccc tgagcaaaga ccccaacgag aagcgcgatc acatggtcct gctggagttc   2880
gtgaccgccg ccgggatcac tctcggcatg gacgagctgt acaagtaa              2928

<210> SEQ ID NO 14
<211> LENGTH: 975
<212> TYPE: PRT
<213> ORGANISM: artificial sequence
<220> FEATURE:
<223> OTHER INFORMATION: PTH receptor-cam8 "chameleon" amino acid
      sequence

<400> SEQUENCE: 14

Met Gly Thr Ala Arg Ile Ala Pro Gly Leu Ala Leu Leu Leu Cys Cys
1               5                   10                  15

Pro Val Leu Ser Ser Ala Tyr Ala Leu Val Asp Ala Asp Asp Val Met
                20                  25                  30

Thr Lys Glu Glu Gln Ile Phe Leu Leu His Arg Ala Gln Ala Gln Cys
            35                  40                  45

Glu Lys Arg Leu Lys Glu Val Leu Gln Arg Pro Ala Ser Ile Met Glu
        50                  55                  60

Ser Asp Lys Gly Trp Thr Ser Ala Ser Thr Ser Gly Lys Pro Arg Lys
65                  70                  75                  80

Asp Lys Ala Ser Gly Lys Leu Tyr Pro Glu Ser Glu Glu Asp Lys Glu
                85                  90                  95

Ala Pro Thr Gly Ser Arg Tyr Arg Gly Arg Pro Cys Leu Pro Glu Trp
            100                 105                 110
```

```
Asp His Ile Leu Cys Trp Pro Leu Gly Ala Pro Gly Glu Val Val Ala
        115                 120                 125

Val Pro Cys Pro Asp Tyr Ile Tyr Asp Phe Asn His Lys Gly His Ala
    130                 135                 140

Tyr Arg Arg Cys Asp Arg Asn Gly Ser Trp Glu Leu Val Pro Gly His
145                 150                 155                 160

Asn Arg Thr Trp Ala Asn Tyr Ser Glu Cys Val Lys Phe Leu Thr Asn
                165                 170                 175

Glu Thr Arg Glu Arg Glu Val Phe Asp Arg Leu Gly Met Ile Tyr Thr
            180                 185                 190

Val Gly Tyr Ser Val Ser Leu Ala Ser Leu Thr Val Ala Val Leu Ile
        195                 200                 205

Leu Ala Tyr Phe Arg Arg Leu His Cys Thr Arg Asn Tyr Ile His Met
    210                 215                 220

His Leu Phe Leu Ser Phe Met Leu Arg Ala Val Ser Ile Phe Val Lys
225                 230                 235                 240

Asp Ala Val Leu Tyr Ser Gly Ala Thr Leu Asp Glu Ala Glu Arg Leu
                245                 250                 255

Thr Glu Glu Glu Leu Arg Ala Ile Ala Gln Ala Pro Pro Pro Pro Ala
            260                 265                 270

Thr Ala Ala Ala Gly Tyr Ala Gly Cys Arg Val Ala Val Thr Phe Phe
        275                 280                 285

Leu Tyr Phe Leu Ala Thr Asn Tyr Tyr Trp Ile Leu Val Glu Gly Leu
    290                 295                 300

Tyr Leu His Ser Leu Ile Phe Met Ala Phe Phe Ser Glu Lys Lys Tyr
305                 310                 315                 320

Leu Trp Gly Phe Thr Val Phe Gly Trp Gly Leu Pro Ala Val Phe Val
                325                 330                 335

Ala Val Trp Val Ser Val Arg Ala Thr Leu Ala Asn Thr Gly Cys Trp
            340                 345                 350

Asp Leu Ser Ser Gly Asn Lys Lys Trp Ile Ile Gln Val Pro Ile Leu
        355                 360                 365

Ala Ser Ile Val Leu Asn Phe Ile Leu Phe Ile Asn Ile Val Arg Val
    370                 375                 380

Leu Ala Thr Lys Leu Arg Glu Thr Asn Ala Gly Met Val Ser Lys Gly
385                 390                 395                 400

Glu Glu Leu Phe Thr Gly Val Val Pro Ile Leu Val Glu Leu Asp Gly
                405                 410                 415

Asp Val Asn Gly His Lys Phe Ser Val Ser Gly Glu Gly Glu Gly Asp
            420                 425                 430

Ala Thr Tyr Gly Lys Leu Thr Leu Lys Phe Ile Cys Thr Thr Gly Lys
        435                 440                 445

Leu Pro Val Pro Trp Pro Thr Leu Val Thr Thr Leu Thr Trp Gly Val
    450                 455                 460

Gln Cys Phe Ser Arg Tyr Pro Asp His Met Lys Gln His Asp Phe Phe
465                 470                 475                 480

Lys Ser Ala Met Pro Glu Gly Tyr Val Gln Glu Arg Thr Ile Phe Phe
                485                 490                 495

Lys Asp Asp Gly Asn Tyr Lys Thr Arg Ala Glu Val Lys Phe Glu Gly
            500                 505                 510

Asp Thr Leu Val Asn Arg Ile Glu Leu Lys Gly Ile Asp Phe Lys Glu
        515                 520                 525

Asp Gly Asn Ile Leu Gly His Lys Leu Glu Tyr Asn Tyr Ile Ser His
```

```
                    530                 535                 540
Asn Val Tyr Ile Thr Ala Asp Lys Gln Lys Asn Gly Ile Lys Ala Asn
545                 550                 555                 560

Phe Lys Ile Arg His Asn Ile Glu Asp Gly Ser Val Gln Leu Ala Asp
                    565                 570                 575

His Tyr Gln Gln Asn Thr Pro Ile Gly Asp Gly Pro Val Leu Leu Pro
                    580                 585                 590

Asp Asn His Tyr Leu Ser Thr Gln Ser Ala Leu Ser Lys Asp Pro Asn
                    595                 600                 605

Glu Lys Arg Asp His Met Val Leu Leu Glu Phe Val Thr Ala Ala Gly
                    610                 615                 620

Ile Thr Leu Gly Met Asp Glu Leu Tyr Lys Arg Cys Asp Thr Arg Gln
625                 630                 635                 640

Gln Tyr Arg Lys Leu Leu Lys Ser Thr Leu Val Leu Met Pro Leu Phe
                    645                 650                 655

Gly Val His Tyr Ile Val Phe Met Ala Thr Pro Tyr Thr Glu Val Ser
                    660                 665                 670

Gly Thr Leu Trp Gln Val Gln Met His Tyr Glu Met Leu Phe Asn Ser
                    675                 680                 685

Phe Gln Gly Phe Phe Val Ala Ile Ile Tyr Cys Phe Cys Asn Gly Glu
                    690                 695                 700

Val Gln Ala Glu Ile Lys Lys Ser Trp Ser Arg Trp Thr Leu Ala Leu
705                 710                 715                 720

Asp Phe Lys Arg Lys Ala Arg Ser Gly Ser Ser Ser Tyr Ser Tyr Gly
                    725                 730                 735

Met Val Ser Lys Gly Glu Glu Leu Phe Thr Gly Val Val Pro Ile Leu
                    740                 745                 750

Val Glu Leu Asp Gly Asp Val Asn Gly His Lys Phe Ser Val Ser Gly
                    755                 760                 765

Glu Gly Glu Gly Asp Ala Thr Tyr Gly Lys Leu Thr Leu Lys Phe Ile
                    770                 775                 780

Cys Thr Thr Gly Lys Leu Pro Val Pro Trp Pro Thr Leu Val Thr Thr
785                 790                 795                 800

Phe Gly Tyr Gly Leu Gln Cys Phe Ala Arg Tyr Pro Asp His Met Lys
                    805                 810                 815

Gln His Asp Phe Phe Lys Ser Ala Met Pro Glu Gly Tyr Val Gln Glu
                    820                 825                 830

Arg Thr Ile Phe Phe Lys Asp Asp Gly Asn Tyr Lys Thr Arg Ala Glu
                    835                 840                 845

Val Lys Phe Glu Gly Asp Thr Leu Val Asn Arg Ile Glu Leu Lys Gly
850                 855                 860

Ile Asp Phe Lys Glu Asp Gly Asn Ile Leu Gly His Lys Leu Glu Tyr
865                 870                 875                 880

Asn Tyr Asn Ser His Asn Val Tyr Ile Met Ala Asp Lys Gln Lys Asn
                    885                 890                 895

Gly Ile Lys Val Asn Phe Lys Ile Arg His Asn Ile Glu Asp Gly Ser
                    900                 905                 910

Val Gln Leu Ala Asp His Tyr Gln Gln Asn Thr Pro Ile Gly Asp Gly
                    915                 920                 925

Pro Val Leu Leu Pro Asp Asn His Tyr Leu Ser Tyr Gln Ser Ala Leu
                    930                 935                 940

Ser Lys Asp Pro Asn Glu Lys Arg Asp His Met Val Leu Leu Glu Phe
945                 950                 955                 960
```

Val Thr Ala Ala Gly Ile Thr Leu Gly Met Asp Glu Leu Tyr Lys
            965                 970                 975

<210> SEQ ID NO 15
<211> LENGTH: 2361
<212> TYPE: DNA
<213> ORGANISM: artificial sequence
<220> FEATURE:
<223> OTHER INFORMATION: A2A-CFP14/10-YFP-C33 cDNA sequence; A2A
      "chameleon"

<400> SEQUENCE: 15

| | |
|---|---|
| atgcccatca tgggctcctc ggtgtacatc acggtggagc tggccattgc tgtgctggcc | 60 |
| atcctgggca atgtgctggt gtgctgggcc gtgtggctca acagcaacct gcagaacgtc | 120 |
| accaactact ttgtggtgtc actggcggcg gccgacatcg cagtgggtgt gctcgccatc | 180 |
| cccttttgcca tcaccatcag caccgggttc tgcgctgcct gccacggctg cctcttcatt | 240 |
| gcctgcttcg tcctggtcct cacgcagagc tccatcttca gtctcctggc catcgccatt | 300 |
| gaccgctaca ttgccatccg catcccgctc cggtacaatg gcttggtgac cggcacgagg | 360 |
| gctaagggca tcattgccat ctgctgggtg ctgtcgtttg ccatcggcct gactcccatg | 420 |
| ctaggttgga caaactgcgg tcagccaaag gagggcaaga accactccca gggctgcggg | 480 |
| gagggccaag tggcctgtct ctttgaggat gtggtcccca tgaactacat ggtgtacttc | 540 |
| aacttctttg cctgtgtgct ggtgcccctg ctgctcatgc tgggtgtcta tttgcggatc | 600 |
| ttcctggcgg cgcgacgaca gctgaagcag atggaggtga caagggcga ggagctgttc | 660 |
| accggggtgg tgcccatcct ggtcgagctg gacggcgacg taaacggcca caagttcagc | 720 |
| gtgtccggcg agggcgaggg cgatgccacc tacggcaagc tgaccctgaa gttcatctgc | 780 |
| accaccggca agctgcccgt gccctggccc accctcgtga ccaccctgac ctggggcgtg | 840 |
| cagtgcttca gccgctaccc cgaccacatg aagcagcacg acttcttcaa gtccgccatg | 900 |
| cccgaaggct acgtccagga gcgcaccatc ttcttcaagg acgacggcaa ctacaagacc | 960 |
| cgcgccgagg tgaagttcga gggcgacacc ctggtgaacc gcatcgagct gaagggcatc | 1020 |
| gacttcaagg aggacggcaa catcctgggg cacaagctgg agtacaacta catcagccac | 1080 |
| aacgtctata tcaccgccga caagcagaag aacggcatca aggccaactt caagatccgc | 1140 |
| cacaacatcg aggacggcag cgtgcagctc gccgaccact accagcagaa cacccccatc | 1200 |
| ggcgacggcc ccgtgctgct gcccgacaac cactacctga gcacccagtc cgccctgagc | 1260 |
| aaagacccca acgagaagcg cgatcacatg gtcctgctgg agttcgtgac cgccgccggg | 1320 |
| atcactctcg gcatggacga gctgtacaag cttcagaagg aggtccatgc tgccaagtca | 1380 |
| ctggccatca ttgtgggct ctttgccctc tgctggctgc ccctacacat catcaactgc | 1440 |
| ttcactttct tctgccccga ctgcagccac gcccctctct ggctcatgta cctggccatc | 1500 |
| gtcctctccc acaccaattc ggttgtgaat cccttcatct acgcctaccg tatccgcgag | 1560 |
| ttccgccaga ccttccgcaa gatcattcgc agccacgtcc tgaggcagca agaaccttc | 1620 |
| aaggcagctg gcaccagtgc ccgggtcgtg agcaagggcg aggagctgtt caccggggtg | 1680 |
| gtgcccatcc tggtcgagct ggacggcgac gtaaacggcc acaagttcag cgtgtccggc | 1740 |
| gagggcgagg gcgatgccac ctacggcaag ctgaccctga agttcatctg caccaccggc | 1800 |
| aagctgcccg tgccctggcc caccctcgtg accaccttcg gctacggcct gcagtgcttc | 1860 |
| gcccgctacc ccgaccacat gaagcagcac gacttcttca gtccgccat gcccgaaggc | 1920 |
| tacgtccagg agcgcaccat cttcttcaag gacgacggca actacaagac ccgcgccgag | 1980 |

```
gtgaagttcg agggcgacac cctggtgaac cgcatcgagc tgaagggcat cgacttcaag    2040
gaggacggca acatcctggg gcacaagctg gagtacaact acaacagcca caacgtctat    2100
atcatggccg acaagcagaa gaacggcatc aaggtgaact tcaagatccg ccacaacatc    2160
gaggacggca gcgtgcagct cgccgaccac taccagcaga acacccccat cggcgacggc    2220
cccgtgctgc tgcccgacaa ccactacctg agctaccagt ccgccctgag caaagacccc    2280
aacgagaagc gcgatcacat ggtcctgctg gagttcgtga ccgccgccgg gatcactctc    2340
ggcatggacg agctgtacaa g                                              2361
```

<210> SEQ ID NO 16
<211> LENGTH: 784
<212> TYPE: PRT
<213> ORGANISM: artificial sequence
<220> FEATURE:
<223> OTHER INFORMATION: A2A-CFP14/10-YFP-C33 amino acid sequence; "A2A chameleon"

<400> SEQUENCE: 16

```
Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
                20                  25                  30

Leu Asn Ser Asn Leu Gln Asn Val Thr Asn Tyr Phe Val Ser Leu Ala
            35                  40                  45

Ala Ala Asp Ile Ala Val Gly Val Leu Ala Ile Pro Phe Ala Ile Thr
        50                  55                  60

Ile Ser Thr Gly Phe Cys Ala Ala Cys His Gly Cys Leu Phe Ile Ala
65                  70                  75                  80

Cys Phe Val Leu Val Leu Thr Gln Ser Ser Ile Phe Ser Leu Leu Ala
                85                  90                  95

Ile Ala Ile Asp Arg Tyr Ile Ala Ile Arg Ile Pro Leu Arg Tyr Asn
            100                 105                 110

Gly Leu Val Thr Gly Thr Arg Ala Lys Gly Ile Ile Ala Ile Cys Trp
        115                 120                 125

Val Leu Ser Phe Ala Ile Gly Leu Thr Pro Met Leu Gly Trp Asn Asn
130                 135                 140

Cys Gly Gln Pro Lys Glu Gly Lys Asn His Ser Gln Gly Cys Gly Glu
                145                 150                 155                 160

Gly Gln Val Ala Cys Leu Phe Glu Asp Val Val Pro Met Asn Tyr Met
            165                 170                 175

Val Tyr Phe Asn Phe Phe Ala Cys Val Leu Val Pro Leu Leu Leu Met
        180                 185                 190

Leu Gly Val Tyr Leu Arg Ile Phe Leu Ala Ala Arg Arg Gln Leu Lys
    195                 200                 205

Gln Met Glu Val Ser Lys Gly Glu Glu Leu Phe Thr Gly Val Val Pro
210                 215                 220

Ile Leu Val Glu Leu Asp Gly Asp Val Asn Gly His Lys Phe Ser Val
225                 230                 235                 240

Ser Gly Glu Gly Glu Gly Asp Ala Thr Tyr Gly Lys Leu Thr Leu Lys
            245                 250                 255

Phe Ile Cys Thr Thr Gly Lys Leu Pro Val Pro Trp Pro Thr Leu Val
        260                 265                 270

Thr Thr Leu Thr Trp Gly Val Gln Cys Phe Ser Arg Tyr Pro Asp His
    275                 280                 285

Met Lys Gln His Asp Phe Phe Lys Ser Ala Met Pro Glu Gly Tyr Val
```

-continued

```
                    290                 295                 300
Gln Glu Arg Thr Ile Phe Phe Lys Asp Asp Gly Asn Tyr Lys Thr Arg
305                 310                 315                 320

Ala Glu Val Lys Phe Glu Gly Asp Thr Leu Val Asn Arg Ile Glu Leu
                    325                 330                 335

Lys Gly Ile Asp Phe Lys Glu Asp Gly Asn Ile Leu Gly His Lys Leu
                    340                 345                 350

Glu Tyr Asn Tyr Ile Ser His Asn Val Tyr Ile Thr Ala Asp Lys Gln
                    355                 360                 365

Lys Asn Gly Ile Lys Ala Asn Phe Lys Ile Arg His Asn Ile Glu Asp
                    370                 375                 380

Gly Ser Val Gln Leu Ala Asp His Tyr Gln Gln Asn Thr Pro Ile Gly
385                 390                 395                 400

Asp Gly Pro Val Leu Leu Pro Asp Asn His Tyr Leu Ser Thr Gln Ser
                    405                 410                 415

Ala Leu Ser Lys Asp Pro Asn Glu Lys Arg Asp His Met Val Leu Leu
                    420                 425                 430

Glu Phe Val Thr Ala Ala Gly Ile Thr Leu Gly Met Asp Glu Leu Tyr
                    435                 440                 445

Lys Leu Gln Lys Glu Val His Ala Ala Lys Ser Leu Ala Ile Ile Val
                    450                 455                 460

Gly Leu Phe Ala Leu Cys Trp Leu Pro Leu His Ile Ile Asn Cys Phe
465                 470                 475                 480

Thr Phe Phe Cys Pro Asp Cys Ser His Ala Pro Leu Trp Leu Met Tyr
                    485                 490                 495

Leu Ala Ile Val Leu Ser His Thr Asn Ser Val Val Asn Pro Phe Ile
                    500                 505                 510

Tyr Ala Tyr Arg Ile Arg Glu Phe Arg Gln Thr Phe Arg Lys Ile Ile
                    515                 520                 525

Arg Ser His Val Leu Arg Gln Gln Glu Pro Phe Lys Ala Ala Gly Thr
                    530                 535                 540

Ser Ala Arg Val Met Val Ser Lys Gly Glu Glu Leu Phe Thr Gly Val
545                 550                 555                 560

Val Pro Ile Leu Val Glu Leu Asp Gly Asp Val Asn Gly His Lys Phe
                    565                 570                 575

Ser Val Ser Gly Glu Gly Glu Gly Asp Ala Thr Tyr Gly Lys Leu Thr
                    580                 585                 590

Leu Lys Phe Ile Cys Thr Thr Gly Lys Leu Pro Val Pro Trp Pro Thr
                    595                 600                 605

Leu Val Thr Thr Phe Gly Tyr Gly Leu Gln Cys Phe Ala Arg Tyr Pro
                    610                 615                 620

Asp His Met Lys Gln His Asp Phe Phe Lys Ser Ala Met Pro Glu Gly
625                 630                 635                 640

Tyr Val Gln Glu Arg Thr Ile Phe Phe Lys Asp Asp Gly Asn Tyr Lys
                    645                 650                 655

Thr Arg Ala Glu Val Lys Phe Glu Gly Asp Thr Leu Val Asn Arg Ile
                    660                 665                 670

Glu Leu Lys Gly Ile Asp Phe Lys Glu Asp Gly Asn Ile Leu Gly His
                    675                 680                 685

Lys Leu Glu Tyr Asn Tyr Asn Ser His Asn Val Tyr Ile Met Ala Asp
                    690                 695                 700

Lys Gln Lys Asn Gly Ile Lys Val Asn Phe Lys Ile Arg His Asn Ile
705                 710                 715                 720
```

```
Glu Asp Gly Ser Val Gln Leu Ala Asp His Tyr Gln Gln Asn Thr Pro
                725                 730                 735

Ile Gly Asp Gly Pro Val Leu Leu Pro Asp Asn His Tyr Leu Ser Tyr
            740                 745                 750

Gln Ser Ala Leu Ser Lys Asp Pro Asn Glu Lys Arg Asp His Met Val
        755                 760                 765

Leu Leu Glu Phe Val Thr Ala Ala Gly Ile Thr Leu Gly Met Asp Glu
    770                 775                 780

<210> SEQ ID NO 17
<211> LENGTH: 477
<212> TYPE: DNA
<213> ORGANISM: Mouse

<400> SEQUENCE: 17
gtgcgtattt accagatcgc caagcgtcgc acccgcgtgc ctcccagccg ccggggtccg      60
gacgcctgtt ccgcgccgcc gggggcgcc gatcgcaggc ccaacgggct gggcccggag     120
cgcggcgcgg gtcccacggg cgctgaggcg gagccgctgc ccacccagct taacggtgcc     180
ccgggggagc ccgcgcccgc cgggcccgc gatggggatg cgctggacct agaggagagt     240
tcgtcgtccg agcacgccga gcggcccccg gggccccgca gacccgaccg cggcccccga     300
gccaagggca agacccgggc gagtcaggtg aagccggggg acagtctgcc gcggcgcggg     360
cccggggccg cggggccggg ggcttcgggg tccggcacg gagaggagcg cggcggggc      420 gccaaagcgt cgcgctggcg cgggaggcaa aaccgggaga aacgcttcac gttcgtg        477

<210> SEQ ID NO 18
<211> LENGTH: 159
<212> TYPE: PRT
<213> ORGANISM: Mouse

<400> SEQUENCE: 18

Val Arg Ile Tyr Gln Ile Ala Lys Arg Arg Thr Arg Val Pro Pro Ser
 1               5                  10                  15

Arg Arg Gly Pro Asp Ala Cys Ser Ala Pro Gly Gly Ala Asp Arg
            20                  25                  30

Arg Pro Asn Gly Leu Gly Pro Glu Arg Gly Ala Gly Pro Thr Gly Ala
        35                  40                  45

Glu Ala Glu Pro Leu Pro Thr Gln Leu Asn Gly Ala Pro Gly Glu Pro
    50                  55                  60

Ala Pro Ala Gly Pro Arg Asp Gly Asp Ala Leu Asp Leu Glu Glu Ser
65                  70                  75                  80

Ser Ser Ser Glu His Ala Glu Arg Pro Pro Gly Pro Arg Arg Pro Asp
                85                  90                  95

Arg Gly Pro Arg Ala Lys Gly Lys Thr Arg Ala Ser Gln Val Lys Pro
            100                 105                 110

Gly Asp Ser Leu Pro Arg Arg Gly Pro Gly Ala Ala Gly Pro Gly Ala
        115                 120                 125

Ser Gly Ser Gly His Gly Glu Glu Arg Gly Gly Ala Lys Ala Ser
    130                 135                 140

Arg Trp Arg Gly Arg Gln Asn Arg Glu Lys Arg Phe Thr Phe Val
145                 150                 155

<210> SEQ ID NO 19
<211> LENGTH: 63
<212> TYPE: DNA
<213> ORGANISM: Mouse
```

```
<400> SEQUENCE: 19
cacgacttcc gacgcgcctt caagaagatc ctctgccgtg gggacagaaa acgcatcgtg      60
tga                                                                    63

<210> SEQ ID NO 20
<211> LENGTH: 20
<212> TYPE: PRT
<213> ORGANISM: Mouse

<400> SEQUENCE: 20

His Asp Phe Arg Arg Ala Phe Lys Lys Ile Leu Cys Arg Gly Asp Arg
1               5                   10                  15

Lys Arg Ile Val
            20

<210> SEQ ID NO 21
<211> LENGTH: 107
<212> TYPE: DNA
<213> ORGANISM: homo sapiens

<400> SEQUENCE: 21
ggatcttcct ggcggcgcga cgacagctga agcagatgga gagccagcct ctgccggggg     60
agcgggcacg gtccacactg cagaaggagg tccatgctgc caagtca                  107

<210> SEQ ID NO 22
<211> LENGTH: 36
<212> TYPE: PRT
<213> ORGANISM: homo sapiens

<400> SEQUENCE: 22

Arg Ile Phe Leu Ala Ala Arg Arg Gln Leu Lys Gln Met Glu Ser Gln
1               5                   10                  15

Pro Leu Pro Gly Glu Arg Ala Arg Ser Thr Leu Gln Lys Glu Val His
            20                  25                  30

Ala Ala Lys Ser
        35

<210> SEQ ID NO 23
<211> LENGTH: 369
<212> TYPE: DNA
<213> ORGANISM: homo sapiens

<400> SEQUENCE: 23
cgtatccgcg agttccgcca gaccttccgc aagatcattc gcagccacgt cctgaggcag     60
caagaacctt tcaaggcagc tggcaccagt gcccgggtct tggcagctca tggcagtgac    120
ggagagcagg tcagcctccg tctcaacggc caccgccag gagtgtgggc aacggcagt     180 gctccccacc ctgagcggag gcccaatggc tatgccctgg gctggtgag tggagggagt    240 gcccaagagt cccaggggaa cacgggcctc ccagacgtgg agctccttag ccatgagctc   300
aagggagtgt gcccagagcc ccctggccta gatgaccccc tggcccagga tggagcagga   360
gtgtcctga                                                            369

<210> SEQ ID NO 24
<211> LENGTH: 102
<212> TYPE: PRT
<213> ORGANISM: homo sapiens

<400> SEQUENCE: 24

Arg Ile Arg Glu Phe Arg Gln Thr Phe Arg Lys Ile Ile Arg Ser His
```

```
                 1               5                  10                 15
Val Leu Arg Gln Gln Glu Pro Phe Lys Ala Ala Gly Thr Ser Ala Arg
             20                  25                 30

Val Leu Ala Ala His Gly Ser Asp Gly Glu Gln Val Ser Leu Arg Leu
             35                  40                 45

Asn Gly His Pro Pro Gly Val Trp Ala Asn Gly Ser Ala Pro His Pro
             50                  55                 60

Glu Arg Arg Pro Asn Gly Tyr Ala Leu Gly Leu Val Ser Gly Gly Ser
 65              70                  75                 80

Ala Gln Glu Ser Gln Gly Asn Thr Gly Leu Pro Asp Val Glu Leu Leu
             85                  90                 95

Ser His Glu Leu Lys Gly
            100

<210> SEQ ID NO 25
<211> LENGTH: 57
<212> TYPE: DNA
<213> ORGANISM: homo sapiens

<400> SEQUENCE: 25
accaagctgc gggagaccaa cgccggccgg tgtgacacac ggcagcagta ccggaag      57

<210> SEQ ID NO 26
<211> LENGTH: 19
<212> TYPE: PRT
<213> ORGANISM: homo sapiens

<400> SEQUENCE: 26

Thr Lys Leu Arg Glu Thr Asn Ala Gly Arg Cys Asp Thr Arg Gln Gln
 1               5                  10                 15

Tyr Arg Lys

<210> SEQ ID NO 27
<211> LENGTH: 393
<212> TYPE: DNA
<213> ORGANISM: homo sapiens

<400> SEQUENCE: 27
gaggtacaag ctgagatcaa gaaatcttgg agccgctgga cactggcact ggacttcaag      60
cgaaaggcac gcagcgggag cagcagctat agctacggcc ccatggtgtc ccacacaagt     120
gtgaccaatg tcggccccg tgtgggactc ggcctgcccc tcagccccg cctactgccc      180 actgccacca ccaacggcca ccctcagctg cctggccatg ccaagccagg acccccagcc     240
ctggagaccc tcgagaccac accacctgcc atggctgctc ccaaggacga tgggttcctc     300
aacggctcct gctcaggcct ggacgaggag gcctctgggc ctgagcggcc acctgccctg     360
ctacaggaag agtgggagac agtcatgtga tga                                  393

<210> SEQ ID NO 28
<211> LENGTH: 129
<212> TYPE: PRT
<213> ORGANISM: homo sapiens

<400> SEQUENCE: 28

Glu Val Gln Ala Glu Ile Lys Lys Ser Trp Ser Arg Trp Thr Leu Ala
 1               5                  10                 15

Leu Asp Phe Lys Arg Lys Ala Arg Ser Gly Ser Ser Ser Tyr Ser Tyr
             20                  25                 30

Gly Pro Met Val Ser His Thr Ser Val Thr Asn Val Gly Pro Arg Val
```

-continued

```
                 35                  40                  45
Gly Leu Gly Leu Pro Leu Ser Pro Arg Leu Leu Pro Thr Ala Thr
 50                  55                  60

Asn Gly His Pro Gln Leu Pro Gly His Ala Lys Pro Gly Thr Pro Ala
 65                  70                  75                  80

Leu Glu Thr Leu Glu Thr Thr Pro Pro Ala Met Ala Ala Pro Lys Asp
                 85                  90                  95

Asp Gly Phe Leu Asn Gly Ser Cys Ser Gly Leu Asp Glu Glu Ala Ser
                100                 105                 110

Gly Pro Glu Arg Pro Pro Ala Leu Leu Gln Glu Glu Trp Glu Thr Val
                115                 120                 125

Met
```

<210> SEQ ID NO 29
<211> LENGTH: 264
<212> TYPE: PRT
<213> ORGANISM: artificial sequence
<220> FEATURE:
<223> OTHER INFORMATION: PTHR-cam7 amino acid sequence

<400> SEQUENCE: 29

```
Glu Val Gln Ala Glu Ile Lys Lys Ser Trp Ser Arg Trp Thr Leu Ala
  1               5                  10                  15

Leu Asp Phe Lys Arg Lys Ala Arg Ser Met Val Ser Lys Gly Glu Glu
                 20                  25                  30

Leu Phe Thr Gly Val Val Pro Ile Leu Val Glu Leu Asp Gly Asp Val
                 35                  40                  45

Asn Gly His Lys Phe Ser Val Ser Gly Glu Gly Glu Gly Asp Ala Thr
 50                  55                  60

Tyr Gly Lys Leu Thr Leu Lys Phe Ile Cys Thr Thr Gly Lys Leu Pro
 65                  70                  75                  80

Val Pro Trp Pro Thr Leu Val Thr Thr Phe Gly Tyr Gly Leu Gln Cys
                 85                  90                  95

Phe Ala Arg Tyr Pro Asp His Met Lys Gln His Asp Phe Phe Lys Ser
                100                 105                 110

Ala Met Pro Glu Gly Tyr Val Gln Glu Arg Thr Ile Phe Phe Lys Asp
                115                 120                 125

Asp Gly Asn Tyr Lys Thr Arg Ala Glu Val Lys Phe Glu Gly Asp Thr
                130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
                165                 170                 175

Tyr Ile Met Ala Asp Lys Gln Lys Asn Gly Ile Lys Val Asn Phe Lys
                180                 185                 190

Ile Arg His Asn Ile Glu Asp Gly Ser Val Gln Leu Ala Asp His Tyr
                195                 200                 205

Gln Gln Asn Thr Pro Ile Gly Asp Gly Pro Val Leu Leu Pro Asp Asn
                210                 215                 220

His Tyr Leu Ser Tyr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
                245                 250                 255

Leu Gly Met Asp Glu Leu Tyr Lys
                260
```

```
<210> SEQ ID NO 30
<211> LENGTH: 270
<212> TYPE: PRT
<213> ORGANISM: artificial sequence
<220> FEATURE:
<223> OTHER INFORMATION: PTHR-cam9 amino acid sequence

<400> SEQUENCE: 30

Glu Val Gln Ala Glu Ile Lys Lys Ser Trp Ser Arg Trp Thr Leu Ala
1               5                   10                  15

Leu Asp Phe Lys Arg Lys Ala Arg Ser Gly Ser Ser Ser Tyr Ser Met
                20                  25                  30

Val Ser Lys Gly Glu Glu Leu Phe Thr Gly Val Val Pro Ile Leu Val
            35                  40                  45

Glu Leu Asp Gly Asp Val Asn Gly His Lys Phe Ser Val Ser Gly Glu
        50                  55                  60

Gly Glu Gly Asp Ala Thr Tyr Gly Lys Leu Thr Leu Lys Phe Ile Cys
65                  70                  75                  80

Thr Thr Gly Lys Leu Pro Val Pro Trp Pro Thr Leu Val Thr Thr Phe
                85                  90                  95

Gly Tyr Gly Leu Gln Cys Phe Ala Arg Tyr Pro Asp His Met Lys Gln
            100                 105                 110

His Asp Phe Phe Lys Ser Ala Met Pro Glu Gly Tyr Val Gln Glu Arg
        115                 120                 125

Thr Ile Phe Phe Lys Asp Asp Gly Asn Tyr Lys Thr Arg Ala Glu Val
    130                 135                 140

Lys Phe Glu Gly Asp Thr Leu Val Asn Arg Ile Glu Leu Lys Gly Ile
145                 150                 155                 160

Asp Phe Lys Glu Asp Gly Asn Ile Leu Gly His Lys Leu Glu Tyr Asn
                165                 170                 175

Tyr Asn Ser His Asn Val Tyr Ile Met Ala Asp Lys Gln Lys Asn Gly
            180                 185                 190

Ile Lys Val Asn Phe Lys Ile Arg His Asn Ile Glu Asp Gly Ser Val
        195                 200                 205

Gln Leu Ala Asp His Tyr Gln Gln Asn Thr Pro Ile Gly Asp Gly Pro
    210                 215                 220

Val Leu Leu Pro Asp Asn His Tyr Leu Ser Tyr Gln Ser Ala Leu Ser
225                 230                 235                 240

Lys Asp Pro Asn Glu Lys Arg Asp His Met Val Leu Leu Glu Phe Val
                245                 250                 255

Thr Ala Ala Gly Ile Thr Leu Gly Met Asp Glu Leu Tyr Lys
            260                 265                 270

<210> SEQ ID NO 31
<211> LENGTH: 272
<212> TYPE: PRT
<213> ORGANISM: artificial sequence
<220> FEATURE:
<223> OTHER INFORMATION: PTHR-cam8 amino acid sequence

<400> SEQUENCE: 31

Glu Val Gln Ala Glu Ile Lys Lys Ser Trp Ser Arg Trp Thr Leu Ala
1               5                   10                  15

Leu Asp Phe Lys Arg Lys Ala Arg Ser Gly Ser Ser Ser Tyr Ser Tyr
                20                  25                  30

Gly Met Val Ser Lys Gly Glu Glu Leu Phe Thr Gly Val Val Pro Ile
            35                  40                  45
```

Leu Val Glu Leu Asp Gly Asp Val Asn Gly His Lys Phe Ser Val Ser
                50                  55                  60

Gly Glu Gly Glu Gly Asp Ala Thr Tyr Gly Lys Leu Thr Leu Lys Phe
 65                  70                  75                  80

Ile Cys Thr Thr Gly Lys Leu Pro Val Pro Trp Pro Thr Leu Val Thr
                 85                  90                  95

Thr Phe Gly Tyr Gly Leu Gln Cys Phe Ala Arg Tyr Pro Asp His Met
                100                 105                 110

Lys Gln His Asp Phe Phe Lys Ser Ala Met Pro Glu Gly Tyr Val Gln
            115                 120                 125

Glu Arg Thr Ile Phe Phe Lys Asp Asp Gly Asn Tyr Lys Thr Arg Ala
            130                 135                 140

Glu Val Lys Phe Glu Gly Asp Thr Leu Val Asn Arg Ile Glu Leu Lys
145                 150                 155                 160

Gly Ile Asp Phe Lys Glu Asp Gly Asn Ile Leu Gly His Lys Leu Glu
                165                 170                 175

Tyr Asn Tyr Asn Ser His Asn Val Tyr Ile Met Ala Asp Lys Gln Lys
                180                 185                 190

Asn Gly Ile Lys Val Asn Phe Lys Ile Arg His Asn Ile Glu Asp Gly
                195                 200                 205

Ser Val Gln Leu Ala Asp His Tyr Gln Gln Asn Thr Pro Ile Gly Asp
            210                 215                 220

Gly Pro Val Leu Leu Pro Asp Asn His Tyr Leu Ser Tyr Gln Ser Ala
225                 230                 235                 240

Leu Ser Lys Asp Pro Asn Glu Lys Arg Asp His Met Val Leu Leu Glu
                245                 250                 255

Phe Val Thr Ala Ala Gly Ile Thr Leu Gly Met Asp Glu Leu Tyr Lys
                260                 265                 270

<210> SEQ ID NO 32
<211> LENGTH: 275
<212> TYPE: PRT
<213> ORGANISM: artificial sequence
<220> FEATURE:
<223> OTHER INFORMATION: PTHR-cam2 amino acid sequence

<400> SEQUENCE: 32

Glu Val Gln Ala Glu Ile Lys Lys Ser Trp Ser Arg Trp Thr Leu Ala
 1               5                  10                  15

Leu Asp Phe Lys Arg Lys Ala Arg Ser Gly Ser Ser Ser Tyr Ser Tyr
                20                  25                  30

Gly Pro Met Val Met Val Ser Lys Gly Glu Glu Leu Phe Thr Gly Val
                35                  40                  45

Val Pro Ile Leu Val Glu Leu Asp Gly Asp Val Asn Gly His Lys Phe
            50                  55                  60

Ser Val Ser Gly Glu Gly Glu Gly Asp Ala Thr Tyr Gly Lys Leu Thr
 65                  70                  75                  80

Leu Lys Phe Ile Cys Thr Thr Gly Lys Leu Pro Val Pro Trp Pro Thr
                 85                  90                  95

Leu Val Thr Thr Phe Gly Tyr Gly Leu Gln Cys Phe Ala Arg Tyr Pro
                100                 105                 110

Asp His Met Lys Gln His Asp Phe Phe Lys Ser Ala Met Pro Glu Gly
            115                 120                 125

Tyr Val Gln Glu Arg Thr Ile Phe Phe Lys Asp Asp Gly Asn Tyr Lys
            130                 135                 140

Thr Arg Ala Glu Val Lys Phe Glu Gly Asp Thr Leu Val Asn Arg Ile

```
                145                 150                 155                 160
Glu Leu Lys Gly Ile Asp Phe Lys Glu Asp Gly Asn Ile Leu Gly His
                165                 170                 175

Lys Leu Glu Tyr Asn Tyr Asn Ser His Asn Val Tyr Ile Met Ala Asp
                180                 185                 190

Lys Gln Lys Asn Gly Ile Lys Val Asn Phe Lys Ile Arg His Asn Ile
                195                 200                 205

Glu Asp Gly Ser Val Gln Leu Ala Asp His Tyr Gln Gln Asn Thr Pro
            210                 215                 220

Ile Gly Asp Gly Pro Val Leu Leu Pro Asp Asn His Tyr Leu Ser Tyr
225                 230                 235                 240

Gln Ser Ala Leu Ser Lys Asp Pro Asn Glu Lys Arg Asp His Met Val
                245                 250                 255

Leu Leu Glu Phe Val Thr Ala Ala Gly Ile Thr Leu Gly Met Asp Glu
                260                 265                 270

Leu Tyr Lys
        275

<210> SEQ ID NO 33
<211> LENGTH: 289
<212> TYPE: PRT
<213> ORGANISM: artificial sequence
<220> FEATURE:
<223> OTHER INFORMATION: PTHR-cam5 amino acid sequence

<400> SEQUENCE: 33

Glu Val Gln Ala Glu Ile Lys Lys Ser Trp Ser Arg Trp Thr Leu Ala
1               5                   10                  15

Leu Asp Phe Lys Arg Lys Ala Arg Ser Gly Ser Ser Ser Tyr Ser Tyr
                20                  25                  30

Gly Pro Met Val Ser His Thr Ser Val Thr Asn Val Gly Pro Arg Val
                35                  40                  45

Gly Leu Met Val Ser Lys Gly Glu Glu Leu Phe Thr Gly Val Val Pro
            50                  55                  60

Ile Leu Val Glu Leu Asp Gly Asp Val Asn Gly His Lys Phe Ser Val
65                  70                  75                  80

Ser Gly Glu Gly Glu Gly Asp Ala Thr Tyr Gly Lys Leu Thr Leu Lys
                85                  90                  95

Phe Ile Cys Thr Thr Gly Lys Leu Pro Val Pro Trp Pro Thr Leu Val
                100                 105                 110

Thr Thr Phe Gly Tyr Gly Leu Gln Cys Phe Ala Arg Tyr Pro Asp His
                115                 120                 125

Met Lys Gln His Asp Phe Phe Lys Ser Ala Met Pro Glu Gly Tyr Val
130                 135                 140

Gln Glu Arg Thr Ile Phe Phe Lys Asp Asp Gly Asn Tyr Lys Thr Arg
145                 150                 155                 160

Ala Glu Val Lys Phe Glu Gly Asp Thr Leu Val Asn Arg Ile Glu Leu
                165                 170                 175

Lys Gly Ile Asp Phe Lys Glu Asp Gly Asn Ile Leu Gly His Lys Leu
                180                 185                 190

Glu Tyr Asn Tyr Asn Ser His Asn Val Tyr Ile Met Ala Asp Lys Gln
                195                 200                 205

Lys Asn Gly Ile Lys Val Asn Phe Lys Ile Arg His Asn Ile Glu Asp
            210                 215                 220

Gly Ser Val Gln Leu Ala Asp His Tyr Gln Gln Asn Thr Pro Ile Gly
225                 230                 235                 240
```

```
Asp Gly Pro Val Leu Leu Pro Asp Asn His Tyr Leu Ser Tyr Gln Ser
            245                 250                 255

Ala Leu Ser Lys Asp Pro Asn Glu Lys Arg Asp His Met Val Leu Leu
            260                 265                 270

Glu Phe Val Thr Ala Ala Gly Ile Thr Leu Gly Met Asp Glu Leu Tyr
            275                 280                 285

Lys

<210> SEQ ID NO 34
<211> LENGTH: 325
<212> TYPE: PRT
<213> ORGANISM: artificial sequence
<220> FEATURE:
<223> OTHER INFORMATION: PTHR-cam1 amino acid sequence

<400> SEQUENCE: 34

Glu Val Gln Ala Glu Ile Lys Lys Ser Trp Ser Arg Trp Thr Leu Ala
1               5                   10                  15

Leu Asp Phe Lys Arg Lys Ala Arg Ser Gly Ser Ser Ser Tyr Ser Tyr
            20                  25                  30

Gly Pro Met Val Ser His Thr Ser Val Thr Asn Val Gly Pro Arg Val
            35                  40                  45

Gly Leu Gly Leu Pro Leu Ser Pro Arg Leu Leu Pro Thr Ala Thr Thr
50                  55                  60

Asn Gly His Pro Gln Leu Pro Gly His Ala Lys Pro Gly Thr Pro Ala
65                  70                  75                  80

Leu Glu Thr Leu Glu Thr Met Val Ser Lys Gly Glu Glu Leu Phe Thr
            85                  90                  95

Gly Val Val Pro Ile Leu Val Glu Leu Asp Gly Asp Val Asn Gly His
            100                 105                 110

Lys Phe Ser Val Ser Gly Glu Gly Glu Gly Asp Ala Thr Tyr Gly Lys
            115                 120                 125

Leu Thr Leu Lys Phe Ile Cys Thr Thr Gly Lys Leu Pro Val Pro Trp
130                 135                 140

Pro Thr Leu Val Thr Thr Phe Gly Tyr Gly Leu Gln Cys Phe Ala Arg
145                 150                 155                 160

Tyr Pro Asp His Met Lys Gln His Asp Phe Phe Lys Ser Ala Met Pro
            165                 170                 175

Glu Gly Tyr Val Gln Glu Arg Thr Ile Phe Phe Lys Asp Asp Gly Asn
            180                 185                 190

Tyr Lys Thr Arg Ala Glu Val Lys Phe Glu Gly Asp Thr Leu Val Asn
            195                 200                 205

Arg Ile Glu Leu Lys Gly Ile Asp Phe Lys Glu Asp Gly Asn Ile Leu
            210                 215                 220

Gly His Lys Leu Glu Tyr Asn Tyr Asn Ser His Asn Val Tyr Ile Met
225                 230                 235                 240

Ala Asp Lys Gln Lys Asn Gly Ile Lys Val Asn Phe Lys Ile Arg His
            245                 250                 255

Asn Ile Glu Asp Gly Ser Val Gln Leu Ala Asp His Tyr Gln Gln Asn
            260                 265                 270

Thr Pro Ile Gly Asp Gly Pro Val Leu Leu Pro Asp Asn His Tyr Leu
            275                 280                 285

Ser Tyr Gln Ser Ala Leu Ser Lys Asp Pro Asn Glu Lys Arg Asp His
            290                 295                 300

Met Val Leu Leu Glu Phe Val Thr Ala Ala Gly Ile Thr Leu Gly Met
```

Asp Glu Leu Tyr Lys
            325

<210> SEQ ID NO 35
<211> LENGTH: 339
<212> TYPE: PRT
<213> ORGANISM: artificial sequence
<220> FEATURE:
<223> OTHER INFORMATION: PTHR-cam4 amino acid sequence

<400> SEQUENCE: 35

Glu Val Gln Ala Glu Ile Lys Lys Ser Trp Ser Arg Trp Thr Leu Ala
1               5                   10                  15

Leu Asp Phe Lys Arg Lys Ala Arg Ser Gly Ser Ser Ser Tyr Ser Tyr
                20                  25                  30

Gly Pro Met Val Ser His Thr Ser Val Thr Asn Val Gly Pro Arg Val
            35                  40                  45

Gly Leu Gly Leu Pro Leu Ser Pro Arg Leu Leu Pro Thr Ala Thr Thr
50                  55                  60

Asn Gly His Pro Gln Leu Pro Gly His Ala Lys Pro Gly Thr Pro Ala
65                  70                  75                  80

Leu Glu Thr Leu Glu Thr Thr Pro Pro Ala Met Ala Ala Pro Lys Asp
                85                  90                  95

Asp Gly Phe Leu Met Val Ser Lys Gly Glu Glu Leu Phe Thr Gly Val
            100                 105                 110

Val Pro Ile Leu Val Glu Leu Asp Gly Asp Val Asn Gly His Lys Phe
        115                 120                 125

Ser Val Ser Gly Glu Gly Glu Gly Asp Ala Thr Tyr Gly Lys Leu Thr
130                 135                 140

Leu Lys Phe Ile Cys Thr Thr Gly Lys Leu Pro Val Pro Trp Pro Thr
145                 150                 155                 160

Leu Val Thr Thr Phe Gly Tyr Gly Leu Gln Cys Phe Ala Arg Tyr Pro
                165                 170                 175

Asp His Met Lys Gln His Asp Phe Phe Lys Ser Ala Met Pro Glu Gly
            180                 185                 190

Tyr Val Gln Glu Arg Thr Ile Phe Phe Lys Asp Asp Gly Asn Tyr Lys
        195                 200                 205

Thr Arg Ala Glu Val Lys Phe Glu Gly Asp Thr Leu Val Asn Arg Ile
210                 215                 220

Glu Leu Lys Gly Ile Asp Phe Lys Glu Asp Gly Asn Ile Leu Gly His
225                 230                 235                 240

Lys Leu Glu Tyr Asn Tyr Asn Ser His Asn Val Tyr Ile Met Ala Asp
                245                 250                 255

Lys Gln Lys Asn Gly Ile Lys Val Asn Phe Lys Ile Arg His Asn Ile
            260                 265                 270

Glu Asp Gly Ser Val Gln Leu Ala Asp His Tyr Gln Gln Asn Thr Pro
        275                 280                 285

Ile Gly Asp Gly Pro Val Leu Leu Pro Asp Asn His Tyr Leu Ser Tyr
290                 295                 300

Gln Ser Ala Leu Ser Lys Asp Pro Asn Glu Lys Arg Asp His Met Val
305                 310                 315                 320

Leu Leu Glu Phe Val Thr Ala Ala Gly Ile Thr Leu Gly Met Asp Glu
                325                 330                 335

Leu Tyr Lys

```
<210> SEQ ID NO 36
<211> LENGTH: 354
<212> TYPE: PRT
<213> ORGANISM: artificial sequence
<220> FEATURE:
<223> OTHER INFORMATION: PTHR-cam3 amino acid sequence

<400> SEQUENCE: 36

Glu Val Gln Ala Glu Ile Lys Lys Ser Trp Ser Arg Trp Thr Leu Ala
1               5                   10                  15

Leu Asp Phe Lys Arg Lys Ala Arg Ser Gly Ser Ser Ser Tyr Ser Tyr
                20                  25                  30

Gly Pro Met Val Ser His Thr Ser Val Thr Asn Val Gly Pro Arg Val
            35                  40                  45

Gly Leu Gly Leu Pro Leu Ser Pro Arg Leu Leu Pro Thr Ala Thr Thr
    50                  55                  60

Asn Gly His Pro Gln Leu Pro Gly His Ala Lys Pro Gly Thr Pro Ala
65                  70                  75                  80

Leu Glu Thr Leu Glu Thr Thr Pro Pro Ala Met Ala Ala Pro Lys Asp
                85                  90                  95

Asp Gly Phe Leu Asn Gly Ser Cys Ser Gly Leu Asp Glu Glu Ala Ser
            100                 105                 110

Gly Pro Glu Met Val Ser Lys Gly Glu Glu Leu Phe Thr Gly Val Val
        115                 120                 125

Pro Ile Leu Val Glu Leu Asp Gly Asp Val Asn Gly His Lys Phe Ser
    130                 135                 140

Val Ser Gly Glu Gly Glu Gly Asp Ala Thr Tyr Gly Lys Leu Thr Leu
145                 150                 155                 160

Lys Phe Ile Cys Thr Thr Gly Lys Leu Pro Val Pro Trp Pro Thr Leu
                165                 170                 175

Val Thr Thr Phe Gly Tyr Gly Leu Gln Cys Phe Ala Arg Tyr Pro Asp
            180                 185                 190

His Met Lys Gln His Asp Phe Phe Lys Ser Ala Met Pro Glu Gly Tyr
        195                 200                 205

Val Gln Glu Arg Thr Ile Phe Phe Lys Asp Asp Gly Asn Tyr Lys Thr
    210                 215                 220

Arg Ala Glu Val Lys Phe Glu Gly Asp Thr Leu Val Asn Arg Ile Glu
225                 230                 235                 240

Leu Lys Gly Ile Asp Phe Lys Glu Asp Gly Asn Ile Leu Gly His Lys
                245                 250                 255

Leu Glu Tyr Asn Tyr Asn Ser His Asn Val Tyr Ile Met Ala Asp Lys
            260                 265                 270

Gln Lys Asn Gly Ile Lys Val Asn Phe Lys Ile Arg His Asn Ile Glu
        275                 280                 285

Asp Gly Ser Val Gln Leu Ala Asp His Tyr Gln Gln Asn Thr Pro Ile
    290                 295                 300

Gly Asp Gly Pro Val Leu Leu Pro Asp Asn His Tyr Leu Ser Tyr Gln
305                 310                 315                 320

Ser Ala Leu Ser Lys Asp Pro Asn Glu Lys Arg Asp His Met Val Leu
                325                 330                 335

Leu Glu Phe Val Thr Ala Ala Gly Ile Thr Leu Gly Met Asp Glu Leu
            340                 345                 350

Tyr Lys

<210> SEQ ID NO 37
```

<211> LENGTH: 368
<212> TYPE: PRT
<213> ORGANISM: artificial sequence
<220> FEATURE:
<223> OTHER INFORMATION: PTHR-cam10 amino acid sequence

<400> SEQUENCE: 37

| | | | | | | | | | | | | | | |
|---|---|---|---|---|---|---|---|---|---|---|---|---|---|---|
| Glu | Val | Gln | Ala | Glu | Ile | Lys | Lys | Ser | Trp | Ser | Arg | Trp | Thr | Leu | Ala |
| 1 | | | | 5 | | | | | 10 | | | | | 15 | |
| Leu | Asp | Phe | Lys | Arg | Lys | Ala | Arg | Ser | Gly | Ser | Ser | Tyr | Ser | Tyr |
| | | | 20 | | | | | 25 | | | | | 30 | |
| Gly | Pro | Met | Val | Ser | His | Thr | Ser | Val | Thr | Asn | Val | Gly | Pro | Arg | Val |
| | | | 35 | | | | | 40 | | | | | 45 | | |
| Gly | Leu | Gly | Leu | Pro | Leu | Ser | Pro | Arg | Leu | Leu | Pro | Thr | Ala | Thr | Thr |
| 50 | | | | | 55 | | | | | 60 | | | | | |
| Asn | Gly | His | Pro | Gln | Leu | Pro | Gly | His | Ala | Lys | Pro | Gly | Thr | Pro | Ala |
| 65 | | | | | 70 | | | | | 75 | | | | | 80 |
| Leu | Glu | Thr | Leu | Glu | Thr | Thr | Pro | Pro | Ala | Met | Ala | Ala | Pro | Lys | Asp |
| | | | | 85 | | | | | 90 | | | | | 95 | |
| Asp | Gly | Phe | Leu | Asn | Gly | Ser | Cys | Ser | Gly | Leu | Asp | Glu | Glu | Ala | Ser |
| | | | 100 | | | | | 105 | | | | | 110 | | |
| Gly | Pro | Glu | Arg | Pro | Pro | Ala | Leu | Leu | Gln | Glu | Glu | Trp | Glu | Thr | Val |
| | | | 115 | | | | | 120 | | | | | 125 | | |
| Met | Met | Val | Ser | Lys | Gly | Glu | Glu | Leu | Phe | Thr | Gly | Val | Val | Pro | Ile |
| 130 | | | | | 135 | | | | | 140 | | | | | |
| Leu | Val | Glu | Leu | Asp | Gly | Asp | Val | Asn | Gly | His | Lys | Phe | Ser | Val | Ser |
| 145 | | | | | 150 | | | | | 155 | | | | | 160 |
| Gly | Glu | Gly | Glu | Gly | Asp | Ala | Thr | Tyr | Gly | Lys | Leu | Thr | Leu | Lys | Phe |
| | | | | 165 | | | | | 170 | | | | | 175 | |
| Ile | Cys | Thr | Thr | Gly | Lys | Leu | Pro | Val | Pro | Trp | Pro | Thr | Leu | Val | Thr |
| | | | 180 | | | | | 185 | | | | | 190 | | |
| Thr | Phe | Gly | Tyr | Gly | Leu | Gln | Cys | Phe | Ala | Arg | Tyr | Pro | Asp | His | Met |
| | | | 195 | | | | | 200 | | | | | 205 | | |
| Lys | Gln | His | Asp | Phe | Phe | Lys | Ser | Ala | Met | Pro | Glu | Gly | Tyr | Val | Gln |
| | 210 | | | | | 215 | | | | | 220 | | | | |
| Glu | Arg | Thr | Ile | Phe | Phe | Lys | Asp | Asp | Gly | Asn | Tyr | Lys | Thr | Arg | Ala |
| 225 | | | | | 230 | | | | | 235 | | | | | 240 |
| Glu | Val | Lys | Phe | Glu | Gly | Asp | Thr | Leu | Val | Asn | Arg | Ile | Glu | Leu | Lys |
| | | | | 245 | | | | | 250 | | | | | 255 | |
| Gly | Ile | Asp | Phe | Lys | Glu | Asp | Gly | Asn | Ile | Leu | Gly | His | Lys | Leu | Glu |
| | | | 260 | | | | | 265 | | | | | 270 | | |
| Tyr | Asn | Tyr | Asn | Ser | His | Asn | Val | Tyr | Ile | Met | Ala | Asp | Lys | Gln | Lys |
| | | | 275 | | | | | 280 | | | | | 285 | | |
| Asn | Gly | Ile | Lys | Val | Asn | Phe | Lys | Ile | Arg | His | Asn | Ile | Glu | Asp | Gly |
| | 290 | | | | | 295 | | | | | 300 | | | | |
| Ser | Val | Gln | Leu | Ala | Asp | His | Tyr | Gln | Gln | Asn | Thr | Pro | Ile | Gly | Asp |
| 305 | | | | | 310 | | | | | 315 | | | | | 320 |
| Gly | Pro | Val | Leu | Leu | Pro | Asp | Asn | His | Tyr | Leu | Ser | Tyr | Gln | Ser | Ala |
| | | | | 325 | | | | | 330 | | | | | 335 | |
| Leu | Ser | Lys | Asp | Pro | Asn | Glu | Lys | Arg | Asp | His | Met | Val | Leu | Leu | Glu |
| | | | 340 | | | | | 345 | | | | | 350 | | |
| Phe | Val | Thr | Ala | Ala | Gly | Ile | Thr | Leu | Gly | Met | Asp | Glu | Leu | Tyr | Lys |
| | | | 355 | | | | | 360 | | | | | 365 | | |

<210> SEQ ID NO 38
<211> LENGTH: 518

```
<212> TYPE: PRT
<213> ORGANISM: artificial sequence
<220> FEATURE:
<223> OTHER INFORMATION: PTHR-PTHR-FRETcontrol amino acid sequence

<400> SEQUENCE: 38
```

| | | | | | | | | | | | | | | |
|---|---|---|---|---|---|---|---|---|---|---|---|---|---|---|
| Glu | Val | Gln | Ala | Glu | Ile | Lys | Lys | Ser | Trp | Ser | Arg | Trp | Thr | Leu | Ala |
| 1 | | | | 5 | | | | | 10 | | | | | 15 |
| Leu | Asp | Phe | Lys | Arg | Lys | Ala | Arg | Met | Val | Ser | Lys | Gly | Glu | Glu | Leu |
| | | | 20 | | | | | 25 | | | | | 30 | | |
| Phe | Thr | Gly | Val | Val | Pro | Ile | Leu | Val | Glu | Leu | Asp | Gly | Asp | Val | Asn |
| | | 35 | | | | | 40 | | | | | 45 | | | |
| Gly | His | Lys | Phe | Ser | Val | Ser | Gly | Glu | Gly | Glu | Gly | Asp | Ala | Thr | Tyr |
| | 50 | | | | | 55 | | | | | 60 | | | | |
| Gly | Lys | Leu | Thr | Leu | Lys | Phe | Ile | Cys | Thr | Thr | Gly | Lys | Leu | Pro | Val |
| 65 | | | | | 70 | | | | | 75 | | | | | 80 |
| Pro | Trp | Pro | Thr | Leu | Val | Thr | Thr | Phe | Gly | Tyr | Gly | Leu | Gln | Cys | Phe |
| | | | | 85 | | | | | 90 | | | | | 95 | |
| Ala | Arg | Tyr | Pro | Asp | His | Met | Lys | Gln | His | Asp | Phe | Phe | Lys | Ser | Ala |
| | | | 100 | | | | | 105 | | | | | 110 | | |
| Met | Pro | Glu | Gly | Tyr | Val | Gln | Glu | Arg | Thr | Ile | Phe | Phe | Lys | Asp | Asp |
| | | 115 | | | | | 120 | | | | | 125 | | | |
| Gly | Asn | Tyr | Lys | Thr | Arg | Ala | Glu | Val | Lys | Phe | Glu | Gly | Asp | Thr | Leu |
| | 130 | | | | | 135 | | | | | 140 | | | | |
| Val | Asn | Arg | Ile | Glu | Leu | Lys | Gly | Ile | Asp | Phe | Lys | Glu | Asp | Gly | Asn |
| 145 | | | | | 150 | | | | | 155 | | | | | 160 |
| Ile | Leu | Gly | His | Lys | Leu | Glu | Tyr | Asn | Tyr | Asn | Ser | His | Asn | Val | Tyr |
| | | | | 165 | | | | | 170 | | | | | 175 | |
| Ile | Met | Ala | Asp | Lys | Gln | Lys | Asn | Gly | Ile | Lys | Val | Asn | Phe | Lys | Ile |
| | | | 180 | | | | | 185 | | | | | 190 | | |
| Arg | His | Asn | Ile | Glu | Asp | Gly | Ser | Val | Gln | Leu | Ala | Asp | His | Tyr | Gln |
| | | 195 | | | | | 200 | | | | | 205 | | | |
| Gln | Asn | Thr | Pro | Ile | Gly | Asp | Gly | Pro | Val | Leu | Leu | Pro | Asp | Asn | His |
| | 210 | | | | | 215 | | | | | 220 | | | | |
| Tyr | Leu | Ser | Tyr | Gln | Ser | Ala | Leu | Ser | Lys | Asp | Pro | Asn | Glu | Lys | Arg |
| 225 | | | | | 230 | | | | | 235 | | | | | 240 |
| Asp | His | Met | Val | Leu | Leu | Glu | Phe | Val | Thr | Ala | Ala | Gly | Ile | Thr | Leu |
| | | | | 245 | | | | | 250 | | | | | 255 | |
| Gly | Met | Asp | Glu | Leu | Tyr | Lys | Ser | Gly | Ser | Ser | Tyr | Ser | Tyr | Gly | |
| | | | 260 | | | | | 265 | | | | | 270 | | |
| Pro | Met | Val | Ser | His | Thr | Ser | Met | Val | Ser | Lys | Gly | Glu | Glu | Leu | Phe |
| | | 275 | | | | | 280 | | | | | 285 | | | |
| Thr | Gly | Val | Val | Pro | Ile | Leu | Val | Glu | Leu | Asp | Gly | Asp | Val | Asn | Gly |
| | 290 | | | | | 295 | | | | | 300 | | | | |
| His | Lys | Phe | Ser | Val | Ser | Gly | Glu | Gly | Glu | Gly | Asp | Ala | Thr | Tyr | Gly |
| 305 | | | | | 310 | | | | | 315 | | | | | 320 |
| Lys | Leu | Thr | Leu | Lys | Phe | Ile | Cys | Thr | Thr | Gly | Lys | Leu | Pro | Val | Pro |
| | | | | 325 | | | | | 330 | | | | | 335 | |
| Trp | Pro | Thr | Leu | Val | Thr | Thr | Leu | Thr | Trp | Gly | Val | Gln | Cys | Phe | Ser |
| | | | 340 | | | | | 345 | | | | | 350 | | |
| Arg | Tyr | Pro | Asp | His | Met | Lys | Gln | His | Asp | Phe | Phe | Lys | Ser | Ala | Met |
| | | 355 | | | | | 360 | | | | | 365 | | | |
| Pro | Glu | Gly | Tyr | Val | Gln | Glu | Arg | Thr | Ile | Phe | Phe | Lys | Asp | Asp | Gly |
| | 370 | | | | | 375 | | | | | 380 | | | | |
| Asn | Tyr | Lys | Thr | Arg | Ala | Glu | Val | Lys | Phe | Glu | Gly | Asp | Thr | Leu | Val |

|   |   |   |   |   |   |   |   |   |   |   |   |
|---|---|---|---|---|---|---|---|---|---|---|---|
| | | 385 | | | 390 | | | 395 | | | 400 |
| Asn | Arg | Ile | Glu | Leu | Lys | Gly | Ile | Asp | Phe | Lys | Glu | Asp | Gly | Asn | Ile |

Asn Arg Ile Glu Leu Lys Gly Ile Asp Phe Lys Glu Asp Gly Asn Ile
                              405                 410                 415

Leu Gly His Lys Leu Glu Tyr Asn Tyr Ile Ser His Asn Val Tyr Ile
              420                 425                 430

Thr Ala Asp Lys Gln Lys Asn Gly Ile Lys Ala Asn Phe Lys Ile Arg
              435                 440                 445

His Asn Ile Glu Asp Gly Ser Val Gln Leu Ala Asp His Tyr Gln Gln
          450                 455                 460

Asn Thr Pro Ile Gly Asp Gly Pro Val Leu Leu Pro Asp Asn His Tyr
465                 470                 475                 480

Leu Ser Thr Gln Ser Ala Leu Ser Lys Asp Pro Asn Glu Lys Arg Asp
              485                 490                 495

His Met Val Leu Leu Glu Phe Val Thr Ala Ala Gly Ile Thr Leu Gly
              500                 505                 510

Met Asp Glu Leu Tyr Lys
              515

<210> SEQ ID NO 39
<211> LENGTH: 1737
<212> TYPE: DNA
<213> ORGANISM: artificial sequence
<220> FEATURE:
<223> OTHER INFORMATION: A2A-FlashPG-CFP-C49 cDNA sequence

<400> SEQUENCE: 39

```
atgcccatca tgggctcctc ggtgtacatc acggtggagc tggccattgc tgtgctggcc      60
atcctgggca atgtgctggt gtgctgggcc gtgtggctca acagcaacct gcagaacgtc     120
accaactact ttgtggtgtc actggcggcg gccgacatcg cagtgggtgt gctcgccatc     180
cccttgcca tcaccatcag caccgggttc tgcgctgcct gccacggctg cctcttcatt      240
gcctgcttcg tcctggtcct cacgcagagc tccatcttca gtctcctggc catcgccatt     300
gaccgctaca ttgccatccg catcccgctc cggtacaatg gcttggtgac cgggacgagg     360
gctaagggca tcattgccat ctgctgggtg ctgtcgtttg ccatcggcct gactcccatg     420
ctaggttgga caactgcggt cagccaaag gagggcaaga ccactcccca gggctgcggg     480
gagggccaag tggcctgtct ctttgaggat gtggtcccca tgaactacat ggtgtacttc     540
aacttctttg cctgtgtgct ggtgccctg ctgctcatgc tgggtgtcta tttgcggatc      600
ttcctggcgg cgcgacgaca gctgaagcag atggagagcc agtgttgtcc ggggtgttgt     660
gcacggtcca cactgcagaa ggaggtccat gctgccaagt cactggccat cattgtgggg     720
ctctttgccc tctgctggct gccctacac atcatcaact gcttcacttt cttctgcccc     780
gactgcagcc acgcccctct ctggctcatg tacctggcca tcgtcctctc ccacaccaat     840
tcggttgtga tcccttcat ctacgcctac cgtatccgcg agttccgcca gaccttccgc     900
aagatcattc gcagccacgt cctgaggcag caagaacctt caaggcagc tggcaccagt     960
gcccgggtct tggcagctca tgcagtgac ggagagcagg tcagcctccg tctcaacggt    1020
gtgagcaagg gcgaggagct gttcaccggg gtggtgccca tcctggtcga gctggacggc    1080
gacgtaaacg gccacaggtt cagcgtgtcc ggcgagggcg agggcgatgc cacctacggc    1140
aagctgaccc tgaagttcat ctgcaccacc ggcaagctgc ccgtgccctg cccacccctc    1200
gtgaccaccc tgacctgggg cgtgcagtgc ttcagccgct accccgacca catgaagcag    1260
cacgacttct tcaagtccgc catgcccgaa ggctacgtcc aggagcgtac catcttcttc    1320
```

-continued

```
aaggacgacg gcaactacaa gacccgcgcc gaggtgaagt tcgagggcga caccctggtg    1380
aaccgcatcg agctgaaggg catcgacttc aaggaggacg gcaacatcct ggggcacaag    1440
ctggagtaca actacatcag ccacaacgtc tatatcaccg ccgacaagca gaagaacggc    1500
atcaaggccc acttcaagat ccgccacaac atcgaggacg gcagcgtgca gctcgccgac    1560
cactaccagc agaacacccc catcggcgac ggccccgtgc tgctgcccga caaccactac    1620
ctgagcaccc agtccgccct gagcaaagac cccaacgaga gcgcgatca catggtcctg    1680 ctggagttcg tgaccgccgc cgggatcact ctcggcatgg acgagctgta caagtaa      1737
```

<210> SEQ ID NO 40
<211> LENGTH: 578
<212> TYPE: PRT
<213> ORGANISM: artificial sequence
<220> FEATURE:
<223> OTHER INFORMATION: A2A-FlashPG-CFP-C49 amino acid sequence

<400> SEQUENCE: 40

```
Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
                20                  25                  30

Leu Asn Ser Asn Leu Gln Asn Val Thr Asn Tyr Phe Val Val Ser Leu
            35                  40                  45

Ala Ala Ala Asp Ile Ala Val Gly Val Leu Ala Ile Pro Phe Ala Ile
        50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Cys Cys Pro Gly Cys Cys Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
    290                 295                 300
```

```
Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
            325                 330                 335

Arg Leu Asn Gly Val Ser Lys Gly Glu Leu Phe Thr Gly Val Val
            340                 345                 350

Pro Ile Leu Val Glu Leu Asp Gly Asp Val Asn Gly His Arg Phe Ser
            355                 360                 365

Val Ser Gly Glu Gly Glu Gly Asp Ala Thr Tyr Gly Lys Leu Thr Leu
            370                 375                 380

Lys Phe Ile Cys Thr Thr Gly Lys Leu Pro Val Pro Trp Pro Thr Leu
385                 390                 395                 400

Val Thr Thr Leu Thr Trp Gly Val Gln Cys Phe Ser Arg Tyr Pro Asp
            405                 410                 415

His Met Lys Gln His Asp Phe Phe Lys Ser Ala Met Pro Glu Gly Tyr
            420                 425                 430

Val Gln Glu Arg Thr Ile Phe Phe Lys Asp Asp Gly Asn Tyr Lys Thr
            435                 440                 445

Arg Ala Glu Val Lys Phe Glu Gly Asp Thr Leu Val Asn Arg Ile Glu
            450                 455                 460

Leu Lys Gly Ile Asp Phe Lys Glu Asp Gly Asn Ile Leu Gly His Lys
465                 470                 475                 480

Leu Glu Tyr Asn Tyr Ile Ser His Asn Val Tyr Ile Thr Ala Asp Lys
            485                 490                 495

Gln Lys Asn Gly Ile Lys Ala His Phe Lys Ile Arg His Asn Ile Glu
            500                 505                 510

Asp Gly Ser Val Gln Leu Ala Asp His Tyr Gln Gln Asn Thr Pro Ile
            515                 520                 525

Gly Asp Gly Pro Val Leu Leu Pro Asp Asn His Tyr Leu Ser Thr Gln
            530                 535                 540

Ser Ala Leu Ser Lys Asp Pro Asn Glu Lys Arg Asp His Met Val Leu
545                 550                 555                 560

Leu Glu Phe Val Thr Ala Ala Gly Ile Thr Leu Gly Met Asp Glu Leu
            565                 570                 575

Tyr Lys

<210> SEQ ID NO 41
<211> LENGTH: 1686
<212> TYPE: DNA
<213> ORGANISM: artificial sequence
<220> FEATURE:
<223> OTHER INFORMATION: A2A-FlashPG-CFP-C33 cDNA sequence

<400> SEQUENCE: 41
atgcccatca tgggctcctc ggtgtacatc acggtggagc tggccattgc tgtgctggcc      60
atcctgggca atgtgctggt gtgctgggcc gtgtggctca acagcaacct gcagaacgtc     120
accaactact ttgtggtgtc actggcggcg gccgacatcg cagtgggtgt gctcgccatc     180
ccctttgcca tcaccatcag caccgggttc tgcgctgcct gccacggctg cctcttcatt     240
gcctgcttcg tcctggtcct cacgcagagc tccatcttca gtctcctggc catcgccatt     300
gaccgctaca ttgccatccg catcccgctc cggtacaatg gcttggtgac cgggacgagg     360
gctaagggca tcattgccat ctgctgggtg ctgtcgtttg ccatcggcct gactcccatg     420
ctaggttgga caactgcggg tcagccaaag gagggcaaga accactccca gggctgcggg     480
```

```
gagggccaag tggcctgtct ctttgaggat gtggtcccca tgaactacat ggtgtacttc      540
aacttctttg cctgtgtgct ggtgcccctg ctgctcatgc tgggtgtcta tttgcggatc      600
ttcctggcgg cgcgacgaca gctgaagcag atggagagcc agtgttgtcc ggggtgttgt      660
gcacggtcca cactgcagaa ggaggtccat gctgccaagt cactggccat cattgtgggg      720
ctctttgccc tctgctggct gcccctacac atcatcaact gcttcacttt cttctgcccc      780
gactgcagcc acgcccctct ctggctcatg tacctggcca tcgtcctctc ccacaccaat      840
tcggttgtga atcccttcat ctacgcctac cgtatccgcg agttccgcca gaccttccgc      900
aagatcattc gcagccacgt cctgaggcag caagaacctt tcaaggcagc tggcaccagt      960
gcccgggtcg tgagcaaggg cgaggagctg ttcaccgggg tggtgcccat cctggtcgag     1020
ctggacggcg acgtaaacgg ccacaggttc agcgtgtccg gcgagggcga gggcgatgcc     1080
acctacggca agctgaccct gaagttcatc tgcaccaccg gcaagctgcc cgtgccctgg     1140
cccaccctcg tgaccaccct gacctggggc gtgcagtgct tcagccgcta ccccgaccac     1200
atgaagcagc acgacttctt caagtccgcc atgcccgaag ctacgtcca ggagcgtacc     1260 atcttcttca aggacgacgg caactacaag acccgcgccg aggtgaagtt cgagggcgac     1320
accctggtga accgcatcga gctgaagggc atcgacttca aggaggacgg caacatcctg     1380
gggcacaagc tggagtacaa ctacatcagc cacaacgtct atatcaccgc cgacaagcag     1440
aagaacggca tcaaggccca cttcaagatc cgccacaaca tcgaggacgg cagcgtgcag     1500
ctcgccgacc actaccagca gaacaccccc atcggcgacg gccccgtgct gctgcccgac     1560
aaccactacc tgagcaccca gtccgccctg agcaaagacc ccaacgagaa gcgcgatcac     1620
atggtcctgc tggagttcgt gaccgccgcc gggatcactc tcggcatgga cgagctgtac     1680
aagtaa                                                                1686
```

<210> SEQ ID NO 42
<211> LENGTH: 561
<212> TYPE: PRT
<213> ORGANISM: artificial sequence
<220> FEATURE:
<223> OTHER INFORMATION: A2A-FlashPG-CFP-C33 amino acid sequence

<400> SEQUENCE: 42

```
Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
```

```
                145                 150                 155                 160
Glu Gly Gln Val Ala Cys Leu Phe Glu Asp Val Val Pro Met Asn Tyr
                165                 170                 175
Met Val Tyr Phe Asn Phe Phe Ala Cys Val Leu Val Pro Leu Leu Leu
                180                 185                 190
Met Leu Gly Val Tyr Leu Arg Ile Phe Leu Ala Ala Arg Arg Gln Leu
                195                 200                 205
Lys Gln Met Glu Ser Gln Cys Cys Pro Gly Cys Cys Ala Arg Ser Thr
    210                 215                 220
Leu Gln Lys Glu Val His Ala Ala Lys Ser Leu Ala Ile Ile Val Gly
225                 230                 235                 240
Leu Phe Ala Leu Cys Trp Leu Pro Leu His Ile Ile Asn Cys Phe Thr
                245                 250                 255
Phe Phe Cys Pro Asp Cys Ser His Ala Pro Leu Trp Leu Met Tyr Leu
                260                 265                 270
Ala Ile Val Leu Ser His Thr Asn Ser Val Val Asn Pro Phe Ile Tyr
                275                 280                 285
Ala Tyr Arg Ile Arg Glu Phe Arg Gln Thr Phe Arg Lys Ile Ile Arg
                290                 295                 300
Ser His Val Leu Arg Gln Gln Glu Pro Phe Lys Ala Ala Gly Thr Ser
305                 310                 315                 320
Ala Arg Val Val Ser Lys Gly Glu Glu Leu Phe Thr Gly Val Val Pro
                325                 330                 335
Ile Leu Val Glu Leu Asp Gly Asp Val Asn Gly His Arg Phe Ser Val
                340                 345                 350
Ser Gly Glu Gly Glu Gly Asp Ala Thr Tyr Gly Lys Leu Thr Leu Lys
                355                 360                 365
Phe Ile Cys Thr Thr Gly Lys Leu Pro Val Pro Trp Pro Thr Leu Val
                370                 375                 380
Thr Thr Leu Thr Trp Gly Val Gln Cys Phe Ser Arg Tyr Pro Asp His
385                 390                 395                 400
Met Lys Gln His Asp Phe Phe Lys Ser Ala Met Pro Glu Gly Tyr Val
                405                 410                 415
Gln Glu Arg Thr Ile Phe Phe Lys Asp Asp Gly Asn Tyr Lys Thr Arg
                420                 425                 430
Ala Glu Val Lys Phe Glu Gly Asp Thr Leu Val Asn Arg Ile Glu Leu
                435                 440                 445
Lys Gly Ile Asp Phe Lys Glu Asp Gly Asn Ile Leu Gly His Lys Leu
450                 455                 460
Glu Tyr Asn Tyr Ile Ser His Asn Val Tyr Ile Thr Ala Asp Lys Gln
465                 470                 475                 480
Lys Asn Gly Ile Lys Ala His Phe Lys Ile Arg His Asn Ile Glu Asp
                485                 490                 495
Gly Ser Val Gln Leu Ala Asp His Tyr Gln Gln Asn Thr Pro Ile Gly
                500                 505                 510
Asp Gly Pro Val Leu Leu Pro Asp Asn His Tyr Leu Ser Thr Gln Ser
                515                 520                 525
Ala Leu Ser Lys Asp Pro Asn Glu Lys Arg Asp His Met Val Leu Leu
                530                 535                 540
Glu Phe Val Thr Ala Ala Gly Ile Thr Leu Gly Met Asp Glu Leu Tyr
545                 550                 555                 560
Lys
```

-continued

<210> SEQ ID NO 43
<211> LENGTH: 1788
<212> TYPE: DNA
<213> ORGANISM: artificial sequence
<220> FEATURE:
<223> OTHER INFORMATION: A2A-CFP-ModelPG-C49 cDNA sequence

<400> SEQUENCE: 43

```
atgcccatca tgggctcctc ggtgtacatc acggtggagc tggccattgc tgtgctggcc      60
atcctgggca atgtgctggt gtgctgggcc gtgtggctca acagcaacct gcagaacgtc     120
accaactact tgtggtgtc actggcggcg ccgacatcg cagtgggtgt gctcgccatc      180
cccttttgcca tcaccatcag caccgggttc tgcgctgcct gccacggctg cctcttcatt     240
gcctgcttcg tcctggtcct cacgcagagc tccatcttca gtctcctggc catcgccatt     300
gaccgctaca ttgccatccg catcccgctc cggtacaatg gcttggtgac cggcacgagg     360
gctaagggca tcattgccat ctgctgggtg ctgtcgtttg ccatcggcct gactcccatg     420
ctaggttgga caactgcgg tcagccaaag gagggcaaga accactccca gggctgcggg     480
gagggccaag tggcctgtct cttttgaggat gtggtcccca tgaactacat ggtgtacttc     540
aacttctttg cctgtgtgct ggtgcccctg ctgctcatgc tgggtgtcta tttgcggatc     600
ttcctggcgg cgcgacgaca gctgaagcag atggagagcc agcctctgcc gggggagcgg     660
gcacggtcca cactgcagaa ggaggtccat gctgccaagt cactggccat cattgtgggg     720
ctctttgccc tctgctggct gccctacac atcatcaact gcttcacttt cttctgcccc     780
gactgcagcc acgccctct ctggctcatg tacctggcca tcgtcctctc ccacaccaat     840
tcggttgtga atcccttcat ctacgcctac cgtatccgcg agttcgcca gaccttccgc     900
aagatcattc gcagccacgt cctgaggcag caagaacctt caaggcagc tggcaccagt     960
gcccgggtct tggcagctca tggcagtgac ggagagcagg tcagcctccg tctcaacggc    1020
gtgagcaagg gcgaggagct gttcaccggg gtggtgccca tcctggtcga gctgacggc     1080
gacgtaaacg gccacaggtt cagcgtgtcc ggcgagggcg agggcgatgc cacctacggc    1140
aagctgaccc tgaagttcat ctgcaccacc ggcaagctgc ccgtgccctg gcccaccctc    1200
gtgaccaccc tgacctgggg cgtgcagtgc ttcagccgct accccgacca catgaagcag    1260
cacgacttct tcaagtccgc catgcccgaa ggctacgtcc aggagcgtac catcttcttc    1320
aaggacgacg gcaactacaa gacccgcgcc gaggtgaagt tcgagggcga caccctggtg    1380
aaccgcatcg agctgaaggg catcgacttc aaggaggacg gcaacatcct ggggcacaag    1440
ctggagtaca actacatcag ccacaacgtc tatatcaccg ccgacaagca gaagaacggc    1500
atcaaggccc acttcaagat ccgccacaac atcgaggacg gcagcgtgca gctcgccgac    1560
cactaccagc agaacacccc catcggcgac ggccccgtgc tgctgcccga caaccactac    1620
ctgagcaccc agtccgccct gagcaaagac cccaacgaga gcgcgatca catggtcctg    1680
ctggagttcg tgaccgccgc cgggatcact ctcggcatgg acgagctgta caaggctgag    1740
gctgcagcgc gcgaagcatg ctgcccaggt tgttgcgctc gcgcatga              1788
```

<210> SEQ ID NO 44
<211> LENGTH: 595
<212> TYPE: PRT
<213> ORGANISM: artificial sequence
<220> FEATURE:
<223> OTHER INFORMATION: A2A-CFP-ModelPG-C49 amino acid sequence

<400> SEQUENCE: 44

Met Pro Ile Met Gly Ser Ser Val Tyr Ile Thr Val Glu Leu Ala Ile

-continued

```
1               5                   10                  15
Ala Val Leu Ala Ile Leu Gly Asn Val Leu Val Cys Trp Ala Val Trp
                20                  25                  30
Leu Asn Ser Asn Leu Gln Asn Val Thr Asn Tyr Phe Val Val Ser Leu
                35                  40                  45
Ala Ala Ala Asp Ile Ala Val Gly Val Leu Ala Ile Pro Phe Ala Ile
50                  55                  60
Thr Ile Ser Thr Gly Phe Cys Ala Ala Cys His Gly Cys Leu Phe Ile
65                  70                  75                  80
Ala Cys Phe Val Leu Val Leu Thr Gln Ser Ser Ile Phe Ser Leu Leu
                85                  90                  95
Ala Ile Ala Ile Asp Arg Tyr Ile Ala Ile Arg Ile Pro Leu Arg Tyr
                100                 105                 110
Asn Gly Leu Val Thr Gly Thr Arg Ala Lys Gly Ile Ala Ile Cys
                115                 120                 125
Trp Val Leu Ser Phe Ala Ile Gly Leu Thr Pro Met Leu Gly Trp Asn
                130                 135                 140
Asn Cys Gly Gln Pro Lys Glu Gly Lys Asn His Ser Gln Gly Cys Gly
145                 150                 155                 160
Glu Gly Gln Val Ala Cys Leu Phe Glu Asp Val Val Pro Met Asn Tyr
                165                 170                 175
Met Val Tyr Phe Asn Phe Phe Ala Cys Val Leu Val Pro Leu Leu Leu
                180                 185                 190
Met Leu Gly Val Tyr Leu Arg Ile Phe Leu Ala Ala Arg Arg Gln Leu
                195                 200                 205
Lys Gln Met Glu Ser Gln Pro Leu Pro Gly Glu Arg Ala Arg Ser Thr
                210                 215                 220
Leu Gln Lys Glu Val His Ala Ala Lys Ser Leu Ala Ile Ile Val Gly
225                 230                 235                 240
Leu Phe Ala Leu Cys Trp Leu Pro Leu His Ile Ile Asn Cys Phe Thr
                245                 250                 255
Phe Phe Cys Pro Asp Cys Ser His Ala Pro Leu Trp Leu Met Tyr Leu
                260                 265                 270
Ala Ile Val Leu Ser His Thr Asn Ser Val Val Asn Pro Phe Ile Tyr
                275                 280                 285
Ala Tyr Arg Ile Arg Glu Phe Arg Gln Thr Phe Arg Lys Ile Ile Arg
                290                 295                 300
Ser His Val Leu Arg Gln Gln Glu Pro Phe Lys Ala Ala Gly Thr Ser
305                 310                 315                 320
Ala Arg Val Leu Ala Ala His Gly Ser Asp Gly Glu Gln Val Ser Leu
                325                 330                 335
Arg Leu Asn Gly Val Ser Lys Gly Glu Glu Leu Phe Thr Gly Val Val
                340                 345                 350
Pro Ile Leu Val Glu Leu Asp Gly Asp Val Asn Gly His Arg Phe Ser
                355                 360                 365
Val Ser Gly Glu Gly Glu Gly Asp Ala Thr Tyr Gly Lys Leu Thr Leu
                370                 375                 380
Lys Phe Ile Cys Thr Thr Gly Lys Leu Pro Val Pro Trp Pro Thr Leu
385                 390                 395                 400
Val Thr Thr Leu Thr Trp Gly Val Gln Cys Phe Ser Arg Tyr Pro Asp
                405                 410                 415
His Met Lys Gln His Asp Phe Phe Lys Ser Ala Met Pro Glu Gly Tyr
                420                 425                 430
```

| | | | | | | | | | | | | |
|---|---|---|---|---|---|---|---|---|---|---|---|---|
|Val|Gln|Glu|Arg|Thr|Ile|Phe|Phe|Lys|Asp|Asp|Gly|Asn|Tyr|Lys|Thr|
| | |435| | | |440| | | |445| | |

Arg Ala Glu Val Lys Phe Glu Gly Asp Thr Leu Val Asn Arg Ile Glu
450 455 460

Leu Lys Gly Ile Asp Phe Lys Glu Asp Gly Asn Ile Leu Gly His Lys
465 470 475 480

Leu Glu Tyr Asn Tyr Ile Ser His Asn Val Tyr Ile Thr Ala Asp Lys
485 490 495

Gln Lys Asn Gly Ile Lys Ala His Phe Lys Ile Arg His Asn Ile Glu
500 505 510

Asp Gly Ser Val Gln Leu Ala Asp His Tyr Gln Gln Asn Thr Pro Ile
515 520 525

Gly Asp Gly Pro Val Leu Leu Pro Asp Asn His Tyr Leu Ser Thr Gln
530 535 540

Ser Ala Leu Ser Lys Asp Pro Asn Glu Lys Arg Asp His Met Val Leu
545 550 555 560

Leu Glu Phe Val Thr Ala Ala Gly Ile Thr Leu Gly Met Asp Glu Leu
565 570 575

Tyr Lys Ala Glu Ala Ala Arg Glu Ala Cys Cys Pro Gly Cys Cys
580 585 590

Ala Arg Ala
595

<210> SEQ ID NO 45
<211> LENGTH: 1737
<212> TYPE: DNA
<213> ORGANISM: artificial sequence
<220> FEATURE:
<223> OTHER INFORMATION: A2A-CFP-C49 cDNA sequence

<400> SEQUENCE: 45

```
atgcccatca tgggctcctc ggtgtacatc acggtggagc tggccattgc tgtgctggcc      60
atcctgggca atgtgctggt gtgctgggcc gtgtggctca acagcaacct gcagaacgtc     120
accaactact ttgtggtgtc actggcggcg gccgacatcg cagtgggtgt gctcgccatc     180
cccttttgcca tcaccatcag caccgggttc tgcgctgcct gccacggctg cctcttcatt     240
gcctgcttcg tcctggtcct cacgcagagc tccatcttca gtctcctggc catcgccatt     300
gaccgctaca ttgccatccg catcccgctc cggtacaatg gcttggtgac cggcacgagg     360
gctaagggca tcattgccat ctgctggtg ctgtcgtttg ccatcggcct gactcccatg     420
ctaggttgga caactgcgg tcagccaaag gagggcaaga accactccca gggctgcggg     480
gagggccaag tggcctgtct ctttgaggat gtggtcccca tgaactacat ggtgtacttc     540
aacttctttg cctgtgtgct ggtgcccctg ctgctcatgc tgggtgtcta tttgcggatc     600
ttcctggcgg cgcgacgaca gctgaagcag atggagagcc agcctctgcc gggggagcgg     660
gcacggtcca cactgcagaa ggaggtccat gctgccaagt cactggccat cattgtgggg     720
ctctttgccc tctgctggct gccccctac atcatcaact gcttcacttt cttctgcccc     780
gactgcagcc acgcccctct ctggctcatg tacctggcca tcgtcctctc ccacaccaat     840
tcggttgtga tcccttcat ctacgcctac cgtatccgcg agttccgcca gaccttccgc     900
aagatcattc gcagccacgt cctgaggcag caagaacctt caaggcagc tggcaccagt     960
gcccgggtct tggcagctca tggcagtgac ggagagcagg tcagcctccg tctcaacggt    1020
gtgagcaagg gcgaggagct gttcaccggg gtggtgccca tcctggtcga gctggacggc    1080
gacgtaaacg gccacaggtt cagcgtgtcc ggcgagggcg agggcgatgc cacctacggc    1140
```

```
aagctgaccc tgaagttcat ctgcaccacc ggcaagctgc ccgtgccctg gcccaccctc    1200
gtgaccaccc tgacctgggg cgtgcagtgc ttcagccgct accccgacca catgaagcag    1260
cacgacttct tcaagtccgc catgcccgaa ggctacgtcc aggagcgtac catcttcttc    1320
aaggacgacg gcaactacaa gacccgcgcc gaggtgaagt tcgagggcga caccctggtg    1380
aaccgcatcg agctgaaggg catcgacttc aaggaggacg gcaacatcct ggggcacaag    1440
ctggagtaca actacatcag ccacaacgtc tatatcaccg ccgacaagca gaagaacggc    1500
atcaaggccc acttcaagat ccgccacaac atcgaggacg gcagcgtgca gctcgccgac    1560
cactaccagc agaacacccc catcggcgac ggccccgtgc tgctgcccga caaccactac    1620
ctgagcaccc agtccgccct gagcaaagac cccaacgaga agcgcgatca catggtcctg    1680
ctggagttcg tgaccgccgc cgggatcact ctcggcatgg acgagctgta caagtaa      1737
```

<210> SEQ ID NO 46
<211> LENGTH: 578
<212> TYPE: PRT
<213> ORGANISM: artificial sequence
<220> FEATURE:
<223> OTHER INFORMATION: A2A-CFP-C49 amino acid sequence

<400> SEQUENCE: 46

```
Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
```

-continued

```
                260                 265                 270
Ala Ile Val Leu Ser His Thr Asn Ser Val Val Asn Pro Phe Ile Tyr
            275                 280                 285
Ala Tyr Arg Ile Arg Glu Phe Arg Gln Thr Phe Arg Lys Ile Ile Arg
            290                 295                 300
Ser His Val Leu Arg Gln Gln Glu Pro Phe Lys Ala Ala Gly Thr Ser
305                 310                 315                 320
Ala Arg Val Leu Ala Ala His Gly Ser Asp Gly Glu Gln Val Ser Leu
            325                 330                 335
Arg Leu Asn Gly Val Ser Lys Gly Glu Glu Leu Phe Thr Gly Val Val
            340                 345                 350
Pro Ile Leu Val Glu Leu Asp Gly Asp Val Asn Gly His Arg Phe Ser
            355                 360                 365
Val Ser Gly Glu Gly Glu Gly Asp Ala Thr Tyr Gly Lys Leu Thr Leu
    370                 375                 380
Lys Phe Ile Cys Thr Thr Gly Lys Leu Pro Val Pro Trp Pro Thr Leu
385                 390                 395                 400
Val Thr Thr Leu Thr Trp Gly Val Gln Cys Phe Ser Arg Tyr Pro Asp
                405                 410                 415
His Met Lys Gln His Asp Phe Phe Lys Ser Ala Met Pro Glu Gly Tyr
            420                 425                 430
Val Gln Glu Arg Thr Ile Phe Phe Lys Asp Asp Gly Asn Tyr Lys Thr
            435                 440                 445
Arg Ala Glu Val Lys Phe Glu Gly Asp Thr Leu Val Asn Arg Ile Glu
    450                 455                 460
Leu Lys Gly Ile Asp Phe Lys Glu Asp Gly Asn Ile Leu Gly His Lys
465                 470                 475                 480
Leu Glu Tyr Asn Tyr Ile Ser His Asn Val Tyr Ile Thr Ala Asp Lys
                485                 490                 495
Gln Lys Asn Gly Ile Lys Ala His Phe Lys Ile Arg His Asn Ile Glu
            500                 505                 510
Asp Gly Ser Val Gln Leu Ala Asp His Tyr Gln Gln Asn Thr Pro Ile
            515                 520                 525
Gly Asp Gly Pro Val Leu Leu Pro Asp Asn His Tyr Leu Ser Thr Gln
    530                 535                 540
Ser Ala Leu Ser Lys Asp Pro Asn Glu Lys Arg Asp His Met Val Leu
545                 550                 555                 560
Leu Glu Phe Val Thr Ala Ala Gly Ile Thr Leu Gly Met Asp Glu Leu
                565                 570                 575
Tyr Lys
```

MILLISECOND ACTIVATION SWITCH FOR SEVEN-TRANSMEMBRANE PROTEINS

CROSS-REFERENCE TO RELATED APPLICATIONS

This application is a national phase application under 35 U.S.C. §371 of International Application No. PCT/EP03/14679 filed 19 Dec. 2003, which claims priority to German Application No. 10259874.6 filed 20 Dec. 2002 and European Application No. 03004394.7 filed 3 Mar. 2003.

The present invention relates to recombinant seven-transmembrane receptor, whereby the amino terminus of said recombinant receptor is located on an extracellular side and the carboxy-terminus is located on an intracellular side of a membrane, comprising at least two detectable labels, whereby a first of said at least two detectable labels is or is located on the carboxy-terminus and whereby a second of said at least two labels is or is located on the first or third intracellular loop or whereby a first of said at least two labels is or is located on the first intracellular loop and a second of at said at least two labels is or is located on the third intracellular loop. Furthermore, nucleic acid molecules encoding said recombinant seven-transmembrane receptors are described as well as vector and host cells comprising the same. Furthermore, the present invention provides for identification and screening methods for molecules or compounds which are capable of modifying the biological end of pharmacological function of seven-transmembrane receptor proteins. Finally, diagnostic compositions comprising the compounds of the present invention as well as kits comprising said compounds are disclosed.

Several seven-transmembrane proteins have been described within the last twenty years, whereby such proteins are mainly involved in signal transduction pathways. Most of these seven-transmembrane proteins are to be classified as proto-oncogenes or as specific receptors which are commonly linked to a signal transduction pathways involving G proteins. G protein-coupled seven transmembrane segment receptors (G protein-coupled receptors, GPCRs, or 7TM receptors) are a very heterogenous class of molecules comprising more than 1000 different members. Accordingly, GPCRs are one of the largest superfamilies of proteins in the human and mammalian body. GPCRs do not share any overall sequence homology yet, one characteristic structural feature, common to all GPCRs is the presence of the characteristic seven-transmembrane spanning α-helical segment connected by alternating intracellular and extracellular loops, whereby the amino terminal is located on the extracellular side and the carboxy terminus is located on the intracellular side. As summarized in Gether, Endocrine Rev. 21 (2000), 90 to 113, G protein-coupled receptors can be classified in several families, termed family "A to C" or family "1 to 3". Family A is normally classified as the rhodopsin/β2-adrenergic receptor-like GPCRs. This family again is subdivided phylogenetically into six subgroups, namely 1. biogenic amine receptors (adrenergic serotonin, dopamine, muscarinic, histamine); 2. CCK-, endothelin-, tachykinin-, neuropeptide Y-, TRH-, neurotensin-, bombesin- and growth hormone secretagogues-receptors plus vertebrate opsin(s)-receptors; 3. invertebrate opsins- and bradykinin-receptors; 4. adenosine-, canabinoid-, malenocortin- and biractory-receptors; 5. chemokine-, fMLP-, C5A-, GnRH-, eicosanoid-, leukotriene-, FSH-, LH-, TSH-, fMLP-, galanin-, nucleotide opioid-, oxytocin-receptors; as well as 6. melatonin receptors and other non-classified receptors. Family B is the family related to glucagons/VIP/calcitonin receptor-like GPCRs which comprise four GPCR-subfamilies, namely: 1. calcitonin-, CGRP- and -receptors; 2. PTH- and PTHrP-receptors; 3. glucagons-, glucagon-like peptide-, GIP-, GHRH-, PACAP-, VIP- and secretin-receptors as well as 4. latrotoxin-receptor. Finally, family C is characterized as the metabotropic neurtransmitter/calcium GPCRs. In this family the following receptors are, inter alia, comprised: 1. metabtropic glutamate-receptors; 2. metabotropic GABA-receptors; 3. calcium-receptors; 4. vornaronasal pheromone receptors; and 5. taste receptors.

As mentioned above, G-protein-coupled receptors (GPCRs) are the largest family of hormone or neurotransmitter receptors; they have a common structure containing seven transmembrane α-helices (Rohrer, Physiol. Rev. 78 (1998), 35-52; Gether, Endocr. Rev. 21 (2000) 90-113; Pierce, Mol. Cell Biol. 3 (2002), 639-650). Their activation by specific agonists—hormones or neurotransmitters—switches them into an active state that couples to and activates G-proteins, the signal transducers. The G-proteins, in turn, can activate a multitude of effector proteins such as ion channels or $2^{nd}$ messenger producing enzymes that alter many functions (e.g., cardiovascular, neural, endocrine) in virtually every type of cells. A large body of data suggests that agonist-induced activation leads to a relative rearrangement of the receptor's transmembrane helices, most notably of helix III and VI (Farrens, Science 274 (1996), 768-770; Sheikh, Nature 383 (1996), 347-350; Sheikh, J. Biol. Chem. 274 (1999),17033-17041).

A very special GPCR is the "light receptor" rhodopsin that senses light by using a covalently coupled ligand, 11-cis retinal, that isomerizes upon capture of a photon. In this case, conformational changes in the "receptor" protein can be inferred from spectroscopic studies of the bound retinal, and multiple activation states formed within milliseconds have been described (Farrens, (1996), loc. cit.); Okada, Trends Biochem. Sci. 26 (2001), 318-324). No comparable techniques are available for hormone- or transmitter-activated receptors. Spectroscopic studies have been done with purified β₂-adrenergic receptor chemically labelled with fluorophores and reconstituted into lipid membranes (Gether, J. Biol. Chem. 270 (1995), 28268-28275; Jensen, J. Biol. Chem. 276 (2001), 9279-9290; Ghanouni, J. Biol. Chem. 276 (2001), 24433-24436; Ghanouni, Proc. Natl. Acad. Sci. USA 98 (2001), 5997-6002). These studies observed agonist-mediated fluorescence changes in the minute time scale. This is much slower than biological responses to receptor activation, which can occur within seconds.

The advent of fluorescent proteins has allowed non-invasive intracellular labeling, especially of peptides, which are easily detectable by optical means. The green fluorescent protein (GFP) from *Aequorea victoria* is now the most widely used reporter gene in many organisms. Multiple variants with different spectral properties have been developed. Furthermore, combinations of fluorescent proteins exhibiting energy transfer provide for differential fluorescence in response to conformational changes in the protein's immediate environment. Based on this principle, fusion constructs have been developed which allow to detect specific analytes such as calcium ions, cAMP or cGMP (e.g. WO 98/40477; Honda, Proc. Natl. Acad. Sci. USA 98 (2001), 2437-2442; Zaccolo, Nat. Cell. Biol. 2 (2000), 25-29). Furthermore, in recent years, detection methods for monitoring fluorescence resonance energy transfer (FRET) have been described for verifying and/or detecting homo- or heterodimerization of molecules or receptor-mediated activation processes. US 02/0048811 describes the visualization of receptor-mediated activation of heterotimeric G-proteins by FRET. Here, the association and/or activation of pairs of G-proteins or of corresponding subunits were measured. DE-A1 101 08 263 relates to the analysis of modifications of proteins with ubiquitin-related proteins. DE-A1 101 08 263 provides a FRET-based test-system comprising ubiquitin-related donor parts and acceptor parts which relates to corresponding target molecules. Both patent applications, US 02/0048811 and DE-A1 101 08 263 exemplify the large body of literature relating to FRET-analysis of "two-component-assays". These assays relate to the distinct use of independent "donor" and "acceptor" molecules/moieties.

Some further limited approaches have been undertaken to employ FRET-technology on an intramolecular basis. For instance, WO 98/40477 describes such a system based on calmodulin which is useful for the measurement of calcium concentrations. However, this system requires as a second analyte binding portion a calcium-calmodulin binding target peptide moiety to which the conformationally flexible calmodulin binds. Thus, the applicability of the fusion protein of WO 98/40477 is restricted and limited in practical use since two binding portions are required and an ubiquitous and endogenous regulatory component is to be used.

U.S. Pat. No. 6,277,627 relates to a glucose biosensor comprising at least one fluorophore and in U.S. Pat. No. 6,197,534 a glucose biosensor is provided which comprises a glucose binding protein with two fluorophores to be employed in FRET-like technologies. Yet, these documents provide for fluorophore-labeled proteins of rather small size which are soluble.

However, the above discussed seven-transmembrane proteins, in particular proto-oncogenes or G protein-coupled receptors (GPCRs) are rather large ("bulky") membrane proteins, wherein FRET- or BRET-based assays have merely been described in dimerization studies.

Based on the large number of GPCR family members and the prominent role in regulating cellular signals, GPCRs represent the most important family of drug targets. The following methods are available to study interaction of potential ligands with GPCRs: a. Ligand-binding assay: This method is restricted to available radio- or fluorescent-labelled ligands, which limits its use to known receptors. Based on the nature of this assay, just the interaction of the ligand with the receptor can be studied but no information regarding the activating, blocking- or inhibiting properties of the ligand on the receptor can be gathered. b. Recording of the activity of G-protein effector systems has become the most important method for drug screening of GPCRs. (Milligan G & Rees S; Trends Pharmacol Sci. 1999 March; 20(3):118-24.) To measure the activity of G-protein effectors makes high-throughput screening on cell based assays possible, however because of the fact that the effector system is several steps downstream of the receptor activation this method has following disadvantages: 1. It is prone to unspecific drug effects, that are not mediated via the investigated GPCR, but rather result from either interaction with elements of the signalling cascade that are downstream of GPCRs or are mediated in parallel via other (endogenous) GPCRs of which many kind are present in various cell systems (world wide web at tumor-gene.org/GPCR/gpcr.html.) 2. Receptor activation and deactivation cannot be determined in real time. Therefore, it is impossible to distinguish between receptor activation and fast receptor desensitization. 3. Recording of GPCR activity depends on expression levels and specificity of subsequent G-proteins and effectors, preventing in many cases exact comparisons between different GPCR subtypes. 4. The strength of the signal or the potency of a ligand to induce full activation of a cellular signal will largely depend on the expression level of the receptor (Bünemann et al. J Biol Chem. 2001 Dec. 14; 276(50):47512-7.). Uncontrolled fluctuations of the expression level will cause variability of the result, and will again make comparisons between different GPCR subtypes difficult. 5. A possibility to measure agonism, partial agonism, inverse agonism and neutral antagonism on the level of the receptor is lacking.

Due to these disadvantages, novel methods that allow detection of receptor activity at the level of the receptor have been tried: Subsequent to the discovery that many GPCRs dimerize or oligomerize it was tried to detect agonist-mediated conformational changes of GPCRs via detection of changes in inter-molecular BRET or FRET (Angers, Annu Rev Pharmacol Toxicol 2002; 42:409-35). However, in the vast majority of tested receptors no ligand-induced change in BRET or FRET could be detected (Angers, (2002), loc. cit.; Rios, Pharmacol Ther 2001 November-December; 92(2-3): 71-87).

A second potential method to monitor GPCR activation based on fluorescence-quenching was developed by using β-2 adrenergic receptors which were mutated by eliminating all but one accessible cysteines and after purification were labelled with a fluorescent tag. In reconstituted membranes, this method was the first to detect ligand induced conformational changes in a GPCR in real time, however the obtained activation kinetics of these receptors were too slow to be in accordance with physiological responses induced via β2-adrenergic receptors (Kobilka & Gether, Methods Enzymol. 2002; 343:170-82).

As mentioned above the GPRC family as well as seven-transmembrane proto-oncogene provide for highly interesting target in drug development. However, the prior art as discussed above provided merely for test systems, wherein antagonists and agonists could be measured in unphysiological time frames. In particular, studies as described above observe agonist mediated changes on, for example, purified β2-adrenergic receptors in the minute time scale.

Therefore, apart from the requirements for detecting specific modifiers for seven-transmembrane proteins, in particular proto-oncogenes or GPCRs, there is also a need for means and methods that allow reliable, fast and easy measurement of the activation of such seven-transmembrane proteins. Such measurements have not been provided for or are not yet accessible by prior art techniques. Preferably, the desired means and methods allow for in vivo measurements.

This technical problem is solved by the provisions of the embodiments as characterized in the claims.

Accordingly, the present invention relates to a recombinant seven-transmembrane receptor, whereby the amino terminus of said recombinant receptor is located on an extracellular side and the carboxy-terminus is located on an intracellular side of a membrane, comprising at least two detectable labels, whereby a first of said at least two detectable labels is or is located (on) the carboxy-terminus and whereby a second of said at least two labels is or is located (on) the first or third intracellular loop or whereby a first of said at least two labels is or is located (on) the first intracellular loop and a second of at said at least two labels is or is located (on) the third intracellular loop.

Inter alia, hormones and neurotransmitters transduce signals via, seven-transmembrane proteins G-protein-coupled receptors as key switches in order to change cellular functions. Despite utilizing common signalling pathways, hormone, amino acids, drugs and neurotransmitter responses exhibit different temporal patterns. To reveal the molecular basis for such differences, the present invention provides for a generally applicable fluorescence-based technique for real-time monitoring of the activation switch for G protein-coupled receptors in single cells, liposomes or membrane preparations. Such direct measurements as disclosed herein were used to investigate the activation of three exemplified seven-transmembrane proteins, namely the $\alpha_{2A}$-adrenergic (neurotransmitter) receptor, the (adenosine) A2A-receptor and the parathyroid hormone (PTH, hormone) receptors. Surprisingly, kinetics that were much faster than previously thought could be observed, for example, ≈40 ms for the $\alpha_{2A}$-adrenergic receptor and ≈1 s for the PTH receptor. The different switch times are in agreement with the distinct biological functions of these receptors. Agonist, partial agonist and antagonist may rapidly switch on and off the receptors in proportion to their respective intrinsic activities. The means and methods provided herein permit the comparison even of agonists and partial agonists of intrinsic activities at the receptors or proto-oncogenes themselves and allow for the detection of millisecond activation-times of G-protein coupled receptors (GPCRs) as well as proto-oncogenes.

Previous work has shown that seven-transmembrane proteins in particular GPCR comprise an entire surface of the cytoplasmic part of about 40 Ångstrom (Bourne, Science 289 (2000), 733-4 and Teller, Biochemistry 40 (2001), 7768-7772). Yet, fluorophores, like GFP variants show a cylindrical or rod-like structure with a diameter of 30 Ångstrom. Accordingly, it was expected that insertion of two fluorophores into the intracellular parts of a seven-transmembrane protein, in particular a GPCR, would cover the entire surface of the cytoplasmic part of said protein or receptor and thereby prevent interaction with protein-coupled further signal transduction part of receptors like arrestins, kinases, or gene proteins. Here, it was surprisingly found that the use of two GFP analoga or fluorophores did not constrain or alter the movements of the transmembrane helices and the receptor was still functional and even provides for a test system wherein intramolecular movements of seven-transmembrane proteins can be monitored in a millisecond range. As documented in the appended examples, it was found that despite the fact that the size of even one GFP variant (diameter of 30 Angstrom, (Tsien, Annu. Rev. Biochem. 1998. 67:509-544) covers almost the entire intracellular surface of a GPCR, receptor constructs fused to two GFP variants are still capable to activate heterotrimeric G proteins. This is in particular surprising, since it was envisaged and speculated by the prior art that fusing or attaching large (protein) moieties, like YFP, GFP or FlAsH, to GPCRs constrains or grossly alters movements of transmembran helices of the receptor required for receptor activation.

The prior art has provided for modifications of GPCRs, for example for point mutation in the 3$^{rd}$ intracellular loop located after the 5$^{th}$ transmembrane region; see Huang, JBC 271 (1996), 33382-33389. However, in this study the introduced mutation caused dramatic changes in the activity of the GPCR studied. Similarly, modifications of proteins involved in signal transduction by incorporation of, inter alia, fluorophores often leads to complete inactivation of the additional protein. As documented in the appended examples, it could be shown that the introduction of green fluorescence protein on position Pro116 of the αA-αB loop of G protein receptor-interacting Gα completely inactivated said interacting protein and correspondingly, the signal transduction pathway. Similarly, Belke-Louis and Schulz (Naunyn-Schmiedebergs Arch. Pharmacol. 2000, 391(suppl.), R51 (189) reported N-terminal or C-terminal fusion proteins of Gαs with EGFP exhibited dramatically impaired functionality.

Furthermore, the expected actual movement of transmembrane helices in GPCRs upon activation by agonists are very small, in particular in the range of 2 to 8 Ångstrom (Altenbach, Biochemistry 25 (2001), 15493-15500). Accordingly, it could certainly not be expected that the recombinant membrane receptors as defined herein provide for assay systems which are capable of detecting this minor confirmation changes and movements by FRET- or BRET-technology, employing fluorophores or chromophores which are located at distal of the agonist activation side.

Accordingly, it could not be expected that the preparation of a recombinant seven-transmembrane receptor as described herein provides for a fast-kinetic, functional and reliable tool for the measurements of receptor-activation or -inhibition. Therefore, the recombinant seven-transmembrane receptor system provided in the present invention and the corresponding uses and methods disclosed herein exhibit major advantages over all other methods described in the prior art since it is now possible to measure receptor activation on the level of the receptor itself. The invention described herein is based on the measurement of conformational changes of a recombinant seven-transmembrane receptor, preferably a G-protein coupled receptor (GPCR) or a proto-oncogene, in response to ligand binding. This allows, inter alia, (as demonstrated in the appended examples) to detect, whether a given chemical compound acts as a full agonist, partial agonist, neutral antagonist or inverse agonist on a given seven-transmembrane receptor, preferably a GPCR or a proto-oncogene. Since the measurement of the conformational change of a seven-transmembrane receptor, preferably a GPCR or a proto-oncogene is based on detection of energy transfer between at least two detectable labels, which represents a non-invasive method, time resolved detection of the activation status of seven-transmembrane receptor, preferably a GPCR or a proto-oncogene can be achieved in living cells. Consequently, kinetics of binding or unbinding of known and unknown ligands can be studied in the natural environment. In fact, in intact cells the characteristics of, for example, a seven-transmembrane receptor, preferably a GPCR or a proto-oncogene induced cellular response is highly dependent on the expression level of receptors, G proteins and effectors and is also modified by a large number of regulatory mechanisms. In contrast the measurement of GPCR activation on the level of the receptor as taught herein is not dependent on downstream regulatory mechanisms and particularly not sensitive to alterations in receptor expression levels.

The term "recombinant seven-transmembrane receptor" as defined herein relates to a membrane protein which is recombinantly produced by methods known in the art; see, inter alia, Sambrook et al., Molecular Cloning: A Laboratory Manual, Cold Spring Harbor Laboratory Press, Cold Spring Harbor, N.Y., 2001. The "recombinant seven-transmembrane receptor" is preferably inserted into a biological and/or artificial membrane, like a cellular membrane, a crude membrane preparation, liposomes as well as artificial membranes comprising micelles, lipid monolayer or lipid bilayers. Yet, most preferably, in accordance with this invention, the recombinant seven-transmembrane receptors as defined herein are located in cellular membranes, for example membranes of cultured cells or membranes of oocytes. As detailed herein below, it is also envisaged that the recombinant seven-transmembrane receptors as defined herein are expressed in transgenic, non-human animals. Accordingly, also cells, tissues and organs of said non-human transgenic animal may express the recombinant seven-transmembrane receptors of the present invention and may be in particular useful in drug screenings.

The term "recombinant seven-transmembrane receptor" also relates to a seven-transmembrane protein, recombinantly produced and comprising said at least two detectable labels, whereby said recombinantly produced membrane receptor/ membrane protein may also consist of a chimeric receptor molecule, i.e. a receptor molecule which is derived from two or more naturally occurring seven-transmembrane proteins. It is, inter alia, envisaged that seven-transmembrane receptors are engineered and recombinantly produced which comprise parts of one GPCR and further parts of another GPCR.

The term "and/or" wherever used herein includes the meaning of "and", "or" all or any other combination of the elements connected by said term.

The terms "amino terminus" or "carboxy terminus" of the recombinant seven-transmembrane receptor corresponds to the amino terminus and carboxy terminus of non-modified naturally occurring seven-transmembrane receptors or proto-oncogenes. The corresponding topology and its verification is, inter alia, disclosed in Gether (2000), loc. cit. Accordingly, the natural orientation of seven-transmembrane receptors is known in the art as, for example, shown in Gether (2000), loc. cit. The orientation also relates to the topology of the inventive recombinant receptors in (crude) membrane preparations or liposomes. Accordingly, the N-terminus should in liposomes be oriented to the outside, whereas the C-terminus should be in the lumen of the liposomes, membrane vesicles. Furthermore, the person skilled in the art is aware of suitable techniques for detecting the orientation of a transmembrane protein and, accordingly, of the recombinant seven-transmembrane receptor of the present invention. Such techniques comprise but are not limited to crystallography, NMR-studies, modeling studies as well as microscopy techniques, like immunolabeling in electron microscopy preparation and the like.

The term "membrane" as used herein and in particular in context of the recombinant seven-transmembrane receptors/ proteins of the present invention relate to naturally occurring membranes as well as to artificial membranes. Preferably, the membranes consist of lipid bilayers. As pointed out above, specific examples are cellular membranes and bio-membranes, like the plasma membrane of cells, the endoplasmic reticulum, mitochondrial membrane, golgi vesicles, lysosomes, peroxisomes, but also cellular membranes of plant cells, like membranes of the chloroplasts or other organelles as well as vacuoles. Yet, most preferably, the cellular or bio-membrane into which the recombinant protein/receptor of the invention is inserted is the plasma membrane of an animal cell, most preferably of a mammalian cell, but also of amphibian cells, like frog oocytes. Yet, as also discussed herein, membrane preparations, like crude membrane preparations or liposomes are envisaged as "membranes" wherein the recombinant membrane receptor/protein of the present invention is inserted.

The term "at least two detectable labels" as used herein means that the recombinant membrane receptor/protein of the invention may comprise at least two, but also three or more detectable labels. The detectable labels will be detailed herein below and may, in particular comprise fluorophores as well as bio-luminescent substances. In accordance with the appended examples, however, most preferred are two detectable labels on one recombinant seven-transmembrane protein of the invention.

The term "said label is or is located on" as employed herein means that the label may either be part of the corresponding region of the recombinant seven-transmembrane receptor, i.e. the first or third intracellular loop or of the carboxy terminus or said label may completely replace the corresponding region of the recombinant seven-transmembrane receptor/ protein, i.e. the first or the third intracellular loop may be replaced by the corresponding label or the C-terminus may be replaced by the corresponding label. Yet, as documented in the appended examples and herein below, it is preferred that the labels are introduced in a region comprised in the first or the third intracellular loop or said at least one label replaces only parts of the C (carboxy)-terminus of the recombinant seven-transmembrane receptor. Accordingly, it is preferred that at least one of said labels is introduced within the first or third intracellular loop of the naturally occurring seven-transmembrane receptor, preferably in naturally occurring GPCRs. Some corresponding third intracellular loop regions are exemplified in the examples and comprise, inter alia, the amino acid sequences as shown in SEQ ID NO: 18, 22 or 26. These third intracellular loop regions may be encoded by sequences as depicted in SEQ ID NOS: 17, 21 and 25. Corresponding exemplified C-terminal region which may comprise one of the detectable labels are shown in form of amino acid sequences in SEQ ID NOS: 19, 23 and 28. In particular, SEQ ID NO: 28 depicts the carboxy terminus of human PTH/PTHrP receptor corresponding modifications of this C-terminus are exemplified in SEQ ID NOS: 29 to 37. Here, in this context, parts of the C-terminus have been deleted and replaced with a green fluorescent protein variant, namely YFP (yellow fluorescent protein). Preferred sites for introduction of the detectable labels are illustrated below and in the appended examples. Furthermore, the examples provide for naturally occurring seven-transmembrane receptors like the α2A-adrenergic receptor, the PTH/PTHrP receptor or the A2A-adenosine receptor which are modified by recombinant technology and comprise at least two detectable labels which are, in particular located on (or within) the third intracellular loop. Corresponding examples are shown in SEQ ID NOS: 12, 14 and 16. In a preferred embodiment of the present invention the detectable label is inserted into the third intracellular loop of the seven-transmembrane receptor/protein and preferably after the second amino acid of the transmembrane region 5 (TM5) and before the second amino acid before the beginning of transmembrane region 6 (TM6). Even more preferred, the detectable label is inserted after amino acid 8 after transmembrane region 5 (TM5) or after amino acid 22 after transmembrane region 5 (TM5). In a preferred embodiment the detectable label is inserted 10 or 12 amino acids before the transmembrane region 6 (TM6). As far as the insertion of the detectable label on the carboxy terminus is concerned, it is preferred that 5 to 25 amino acids of the natural carboxy terminus remain at the end of transmembrane region 7 (TM7). Preferably, the detectable label is inserted after the $16^{th}$ or $20^{th}$ amino acid after transmembrane region 7 (TM7). Therefore, it is envisaged that the detectable labels either replace naturally occurring amino acids on the first and/or third loop of seven-transmembrane receptors or the C-terminus of the same or that said detectable labels are inserted into the naturally occurring amino acid sequences of the same. The term "said label is or is located on" also comprises the possibility that said label specifically attaches to or binds to the first and/or the third loop as defined herein. A corresponding example of a label which specifically binds to a specific sequence artificially introduced into said loops is the FlAsH-compound described herein below.

As far as insertion of detectable labels of the first intracellular loop are concerned, again, it is preferred that said label is inserted two amino acids after the end of transmembrane region 1 (TM1) and two amino acids before the beginning of transmembrane region 2 (TM2). Most preferably, the detectable label is inserted in the middle of the first intracellular loop. The same applies, mutatis mutandis for the third intracellular loop insertion. Yet, it is to be noted that all insertions of the detectable label may lead to a deletion/replacement of naturally occurring amino acids in the first or third intracellular loop as well as the C-terminus.

In a most preferred embodiment of the recombinant membrane receptor of the invention, the first detectable label is or is located on the third intracellular loop of said membrane receptor and the second detectable label is or is located on the carboxy terminus. This most preferred embodiment of the recombinant membrane receptor/protein of the present invention is also exemplified in the appended scientific examples. Furthermore, corresponding recombinant constructs are depicted as nucleic acid sequences in appended SEQ ID NOS: 11, 13, 15, 39 and 41 and in the corresponding amino acid sequences SEQ ID NOS: 12, 14, 16, 40 and 42. However, it is of note that these amino acid sequences as well as the encoding nucleic acid sequences merely comprise illustrative examples.

The invention in particular relates to a recombinant membrane receptor/protein, whereby said membrane receptor is a G-protein-coupled receptor or a proto-oncogene. Accordingly, the present invention provides for recombinant membrane receptors which are derived from naturally occurring G protein-coupled receptors or naturally occurring proto-oncogenes. As shown in the appended examples the invention provides for genetically/recombinantly modified G protein-coupled receptors or proto-oncogenes which are particularly useful in methods provided herein, i.e. screening methods for antagonists as well as agonists of G protein-coupled receptors or proto-oncogenes, preferably involved in the signal transduction pathways. The proto-oncogenes which are in their naturally occurring form seven-transmembrane proteins and which are, in accordance with this invention, modified and recombinantly produced comprise the above-recited at least two detectable labels on the above-recited positions. In a preferred embodiment this proto-oncogene belongs to the "frizzled/smoothened family" and comprises the protein "frizzled" or "smoothened".

In a most preferred embodiment of the present invention the recombinant seven-transmembrane receptor is derived from a naturally occurring G protein-coupled receptor or is derived from a corresponding orphan receptor; i.e. putative or unclassified GPCRs. G protein-coupled receptors to be modified and recombinantly produced in accordance with this invention comprise the GPCRs as, inter alia, defined in Gether (2000), loc. cit. as well as GPCRs comprised in the following classes A to E. Further general classifications of the GPCR superfamily are provided by the classification in class A to E.

Class A (or class 1) comprises rhodopsin-like receptors family, class B (or class 2) comprises secretin-like receptors family, class C (or class 3) comprises calcium sensing-like receptors family, class D (or class 4) comprises yeast alpha factor-like receptors family, class E (or class 5) comprises dictyostelium attractant-like receptors family.

Class A rhodopsin like GPCRs comprise, but are not limited to amine-, peptide-, hormone protein-, (rhod)opsin-, olfactory-, prostanoid-, nucleotide-like-, cannabis-, platelet activating factor-, gonadotropin-releasing hormone-, thyrotropin-releasing hormone & secretagogue-, melatonin-, viral-, lysosphingolipid & LPA (EDG)-, leukotriene B4 receptor, class A Orphan/other receptor.

Class B Secretin like GPCRs comprise, but are not limited to calcitonin-, corticotropin releasing factor-, gastric inhibitory peptide-, glucagon-, growth hormone-releasing hormone-, parathyroid hormone-, PACAP-, secretin-, vasoactive intestinal polypeptide-, diuretic hormone-, EMR1-, latrophilin-, brain-specific angiogenesis inhibitor (BAI)-, methuselah-like proteins (MTH)-, cadherin EGF LAG (CELSR)-receptor.

Class C Metabotropic glutamate/pheromone like GPCRs comprise, but are not limited to metabotropic glutamate-, extracellular calcium-sensing-, putative pheromone receptors, GABA-B-, orphan GPRC5-receptor.

Class D Fungal pheromone comprise, but are not limited to fungal pheromone STE2-like-, fungal pheromone STE3-like-receptor.

Furthermore, the invention also provides for modified GPCRs from class E, namely cAMP receptors (Dictyostelium), like frizzled/Smoothened family-, frizzled-, Smoothened-receptor.

Accordingly, the present invention is not limited to a modified or recombinantly produced seven-transmembrane receptors of mammalian origin but also comprise recombinantly seven-transmembrane receptors from other eukaryotes, including yeasts, plants, fungi as well as non-vertebrates animals.

The recombinant membrane receptor/protein of the invention is, preferably derived from a naturally occurring proto-oncogene like smoothened receptor (Smo) or frizzled receptor or is a G-protein-coupled receptor (GPCR) is selected from the group consisting of a rhodopsin/$\beta 2$ adrenergic receptor-like GPCR, a glucagon/VIP/calcitonin receptor-like GPCR and a metabotropic neurotransmitter/calcium receptor. In a most preferred embodiment, said rhodopsin/$\beta 2$-adrenergic receptor-like GPCR is the $\alpha 2A$ adrenergic receptor or the adenosine receptor A2A and said glucagon/VIP/calcitonin receptor-like GPCR is the parathyroid hormone (PTH) receptor.

In accordance with this invention and as pointed out herein above, naturally occurring seven-transmembrane protein may be genetically/recombinantly modified in order to provide from the recombinant seven-transmembrane receptors of the present invention. For example, the human PTH/PTHrP receptor gene is well known in the art and deposited under GeneBank accession No. U22401. A mouse $\alpha 2A$-adrenergic receptor can be found under GeneBank accession No. M99377. The gene encoding for human A2A receptor can be found in GeneBank accession No. M97370. Corresponding sequences on nucleic acid as well as amino acid level are depicted and described in appended SEQ ID NOS: 1 to 6. Yet, it is of note that the G protein-coupled receptors or the proto-oncogene to be employed in accordance with the present invention for the generation of recombinant seven-transmembrane receptors as defined herein above are not limited to GPCRs or proto-oncogenes derived from human or mouse. It is in particular settings also envisaged to employ G protein-coupled receptors or proto-oncogenes from other vertebrates like rats, rabbits, guinea pigs, dogs, cats or frogs and fish.

The detectable labels to be introduced into the recombinant seven-transmembrane receptor/proteins of the present invention are preferably fluorescent labels or bioluminescent labels.

The fluorescence labels are, in particular, selected from "green fluorescent protein" or "GFP" and its variants or mutants. Preferably, said group comprises GFP (green), YFP (yellow), CFP (cyan), BFP (blue) and dsRed.

The bioluminescent labels may be luciferase (like renilla luciferase or firefly luciferase). Furthermore, it is envisaged that the fluorescence label is produced by binding the FlAsH compound to specific epitopes of said $1^{st}$ and $3^{rd}$ loop or said C-terminus of the recombinant seven-transmembrane receptor.

FlAsH (fluorescein arsenical helix binder, FlAsH-compound) can specifically bind a protein comprising the sequence Cys-Cys-X-X-Cys-Cys (X represents any amino acid but preferentially X-X is Pro-Gly). FlAsH fluoresces after binding to the sequence Cys-Cys-X-X-Cys-Cys, and thus allows site-specific fluorescent labeling of recombinant proteins in living cells. Accordingly, in context of the present invention, intramolecular FRET with GPCRs may be performed with a recombinant receptor containing the bound FlAsH (to the epitope, Cys-Cys-X-X-Cys-Cys; which may be recombinantly introduced in the first or third loop as defined herein or into the carboxy-terminus of a seven-transmembrane receptor as defined herein) and the, inter alia, CFP; see, Griffin, Science 281(1998), 269-272. A red-emitting analog of FlAsH (named REASH) is also known in the art and may be used for FRET experiment in accordance with this invention by use of, inter alia, YFP; see Gaietta, Science 296 (2002), 503-507. The appended examples provide for corresponding inventive recombinant constructs. These are also depicted in SEQ ID NO: 40 and 42 and may be encoded by nucleic acid molecules as shown in SEQ ID NOs: 39 and 40. In a particular preferred embodiment of the present invention a recombinant seven-transmembrane receptor as described herein is employed which comprise as a first label a fluorescein arsenical helix binder (FlAsH/flash/FlAsH) and as a second label CFP; whereby said label attaches to the artificially or recombinantly introduced CCXXCC sequence as defined above.

The use of the fluorophore FlAsH may in certain experimental settings be advantageous, for example if a "wildtype" (wt)-like complex of a receptor to its interacting molecule, for example a GPCR to its G-protein is desired. Furthermore, as documented in the appended examples, an increase of amplitude of agonist-induced FRET changes may be observed when FlAsH-compound (for example instead of YFP) is employed. This increases the signal to noise ratio.

The detection portions/labels present in the recombinant seven-transmembrane protein of the invention facilitate the detection of a conformational change, which, in turn, is indicative for change of the energy emitted by the detection portions/detectable labels.

In one embodiment of the recombinant seven-transmembrane receptor of the invention, these detection labels are portions of a split fluorescent protein. Preferably, this split fluorescent portions is a split green fluorescent protein (split GFP). The term "green fluorescent protein" or "GFP" as used throughout the present application refers to the GFP initially cloned by Prasher (Gene 111 (1992), 229-233) from Aequorea victoria and mutants thereof showing GFP activity. The term "GFP activity" refers to the known properties of a GFP, i.e. fluorescence emission upon excitation by a suitable light, the capacity of autocatalytic maturation involving folding into tertiary structure and the formation of the chromophore and the independence of any co-factors or metabolic energy supply for carrying out fluorescence as well as autocatalytic maturation. These properties are well known in the art and for example reviewed by Tsien (Ann. Rev. Biochem. 67 (1998), 509-544). For the purposes of the present invention, unless otherwise stated, any detectable emission wavelength of a GFP mutant can be useful for applying the recombinant seven-transmembrane protein of the invention. In the prior art, many GFP mutants are described, wherein specific amino acid residues are substituted with the effect of an improved fluorescence efficiency and/or a shifted excitation and/or emission wavelength (see, e.g., Heim, Methods Enzymol. 302 (1999), 408-423; Heikal et al., PNAS 97 (2000), 11996-12001). Particularly, mutating glutamine in position 69 to methionine can reduce the inherent pH and halide sensitivity of eYFP (Griesbeck et al., J. Biol. Chem. (2001) 276, 29188-29194). Thus, if eYFP, or a derivative thereof having substantially the same excitation and emission spectrum, is used as one detection portion of the fusion protein of the invention, it is preferred that the eYFP or derivative thereof shows this mutation. Yet, as shown in the appended examples, YFP is also useful in accordance with this invention. Examples for GFP mutants useful for applying the invention include (enhanced) yellow fluorescent protein ((e)YFP), (enhanced) cyan fluorescent protein ((e)CFP), (enhanced) blue fluorescent protein ((e)BFP), (enhanced) green fluorescent protein ((e)GFP), DsRED, Citrine and Sapphire. Within the scope of the present invention, any GFP mutant or functional analog of GFP may be used as long as it shows fluorescent activity. Preferably, such GFP variants/mutants are encoded by a nucleic acid molecule that hybridizes, preferably under stringent conditions, with the nucleotide sequence encoding the wild-type GFP, or with variants/mutants as the sequence depicted under SEQ ID NOS: 7 to 10. These GFP-mutants/variants shown in SEQ ID NOS: 7 to 10 relate to the most preferred GFP variants to be employed in this invention, namely enhanced cyan fluorescent protein (eCFP) and yellow fluorescent protein (YFP). Suitable preferred hybridization conditions and sequence identity values for preferred hybridizing nucleotide sequences encoding a mutant GFP are mentioned below in connection with functional analogs of the recombinant seven-transmembrane protein of the invention.

The term "split fluorescent protein" refers to a fluorescent protein the amino acid sequence of which is divided into two portions, whereby upon secondary spatial joining of these portions, the split fluorescent protein assumes a three-dimensional structure which allows it to emit fluorescence when excited by light of a suitable wavelength. It is for example contemplated that the split fluorescent protein is a split GFP, as it has been described by Baird (Proc. Natl. Acad. Sci. USA 96 (1999), 11241-11246). Following the teachings of the prior art, it is possible for a person skilled in the art to divide a GFP into two split GFP portions for fusing them to the $1^{st}$ and $3^{rd}$ loop or a C-terminus of the recombinant seven-transmembrane protein of the invention. It is furthermore conceivable that other fluorescent proteins than GFP, e.g. those mentioned infra, may be split so as to constitute two detection portions in the same manner as split GFP described herein.

In another embodiment of the present invention, the first detection label is an energy-emitting protein portion and the second detection portion is a fluorescent protein label or vice versa. In connection with this embodiment, it is unimportant on which part of the seven-transmembrane protein the first detection portion is located with respect to the other part defined herein, i.e. whether said detection label is located on the first or third intracellular loop or the C-terminus of the inventive recombinant protein. The term "energy-emitting protein portion" refers to proteins capable of radiative energy emission which can (i) take up energy in a suitable form and (ii) transmit at least part of this energy by resonance energy transfer (RET) to the second detection label being a fluorescent protein portion which is thereby elicited to energy emission. The form of energy uptake may be anything that is conceivable to the person skilled in the art and may involve, e.g., a chemical reaction (chemiluminescence or bioluminescence) or absorption of radiation (fluorescence or phosphorescence).

The term "fluorescent protein portion" refers to proteins that are capable of fluorescence, i.e. to absorb energy from radiation of a certain wave length, e.g. ultra-violet or visible light, and to emit this energy or a part thereof by radiation, wherein the emitted radiation has a higher wavelength than the eliciting radiation. There are many examples of fluorescent proteins described in the literature that may be useful in connection with the present invention such as GFPs as mentioned above, fluorescent proteins from non-bioluminescent organisms of the class Anthozoa (WO 00/34318, WO 00/34319, WO 00/34320, WO 00/34321, WO 00/34322, WO 00/34323, WO 00/34324, WO 00/34325, WO 00/34326, WO 00/34526) or the fluorescent protein bmFP from *Photobacterium phosphoreum* (Karatani, Photochem. Photobiol. 71 (2000), 230). Preferred, however, are fluorescent proteins being a YFP and eCFP as employed in the appended examples.

The term "resonance energy transfer" (RET) refers to a non-radiative transfer of excitation energy from a donor (first detection portion) to an acceptor molecule (second detection portion). The conformational change of the recombinant seven-transmembrane receptor results in a detectable change of RET between the detection portions. Such a change can for instance be taken from a comparison of the emission spectra of a recombinant seven-transmembrane receptor in the absence of a suitable binding compound/ligand/agonist or antagonist with the same recombinant seven-transmembrane receptor in the presence of such a compound. If, for example, RET is increased, the emission peak of the acceptor is raised and the emission peak of the donor is diminished. Thus, the ratio of the emission intensity of the acceptor to that of the donor is indicative for the degree of RET between the detection portions. The conformational change of the recombinant seven-transmembrane protein upon binding of a compound, ligand, agonist or antagonist may result either in a decrease or an increase of the distance between the detection portions.

In a most preferred embodiment of the invention, recombinant membrane receptor of the invention, is a G-protein-coupled receptor comprising at least two labels is selected from the group consisting of:
(a) a polypeptide as shown in SEQ ID NOS: 12, 14, 16, 40 or 42;
(b) a polypeptide encoded by a nucleic acid sequence as depicted in any one of SEQ ID NOS: 11, 13, 15, 39 or 41;
(c) a recombinant membrane receptor as defined herein encoded by a nucleotide sequence which hybridizes to a nucleotide sequence as defined (b); and
(d) a recombinant membrane receptor as defined herein encoded by a nucleic acid sequence being degenerate as a result of the genetic code to a nucleic acid sequence as defined in (b) or (c).

In accordance with this invention, a recombinant membrane receptor is described, wherein the third intracellular loop is or comprises the first detectable label whereby said third intracellular loop is selected from the group consisting of
(a) a polypeptide depicted in SEQ ID NOS: 18, 22 or 26;
(b) a polypeptide encoded by a nucleic acid sequence as depicted in SEQ ID NOS: 17, 21 or 25;
(c) a third intracellular loop encoded by a nucleotide sequence which hybridizes to a nucleotide sequence as defined (b); and
(d) a third intracellular loop encoded by a nucleic acid sequence being degenerate as a result of the genetic code to a nucleic acid sequence as defined in (b) or (c).

Accordingly, another embodiment of the present invention relates to nucleic acid molecules comprising a nucleotide sequence encoding the recombinant seven-transmembrane protein of the present invention.

The term "nucleic acid molecule" means DNA or RNA or both in combination or any modification thereof that is known in the state of the art (see, e.g., U.S. Pat. No. 5,525,711, U.S. Pat. No. 4,711,955, U.S. Pat. No. 5,792,608, or EP 302175 for examples of modifications). Such nucleic acid molecule(s) are single- or double-stranded, linear or circular and without any size limitation. The nucleic acid molecules of the invention can be obtained for instance from natural sources or may be produced synthetically or by recombinant techniques, such as PCR. In a preferred embodiment, the nucleic acid molecules of the invention are DNA molecules, in particular genomic DNA or cDNA, or RNA molecules. Preferably, the nucleic acid molecule is double-stranded DNA. Particular inventive nucleic acid molecules are depicted in SEQ ID NOS: 11, 13 and 15.

The nucleic acid molecule comprising a nucleotide sequence encoding it is a recombinant nucleic acid molecule, i.e. a nucleic acid molecule that has been produced by a technique useful for artificially combining nucleic acid molecules or parts thereof that were beforehand not connected as in the resulting recombinant nucleic acid molecule. Suitable techniques are for example available from the prior art, as represented by Sambrook and Russell (2001), Molecular Cloning: A Laboratory Manual, CSH Press and Ausubel, Current Protocols in Molecular Biology, Green Publishing Associates and Wiley Interscience, N.Y. (1989) as well as Vilardaga (1995), Biotechniques 18, 605-606. Furthermore, the corresponding techniques are illustrated in the appended examples. Said techniques comprise in particular site-directed mutagenesis.

In this context the term "hybridization" means hybridization under conventional hybridization conditions. They may be low stringent, preferably stringent (i.e. high stringent) hybridization conditions, as for instance described in Sambrook at al., Molecular Cloning, A Laboratory Manual, loc. cit. In an especially preferred embodiment the term "hybridization" means that hybridization occurs under the following conditions.

Furthermore, the present invention relates to expression cassettes comprising the above-described nucleic acid molecule of the invention and operably linked thereto control sequences allowing expression in prokaryotic or eukaryotic cells.

Suitable expression control sequences include promoters that are applicable in the target host organism or host cell. Such promoters are well known to the person skilled in the art for diverse hosts from prokaryotic and eukaryotic organisms and are described in the literature. For example, such promoters can be isolated from naturally occurring genes or can be synthetic or chimeric promoters. Likewise, the promoter can already be present in the target genome and will be linked to the nucleic acid molecule by a suitable technique known in the art, such as for example homologous recombination. Specific examples of expression control sequences and sources from where they can be derived are given further below and in the appended examples. All constructs were in pcDNA3.

Expression cassettes according to the invention are particularly meant for an easy to use insertion into target nucleic acid molecules such as vectors or genomic DNA. For this purpose, the expression cassette is preferably provided with nucleotide sequences at its 5'- and 3'-flanks facilitating its removal from and insertion into specific sequence positions like, for instance, restriction enzyme recognition sites or target sequences for homologous recombination as, e.g. catalyzed by recombinases.

The present invention also relates to vectors, particularly plasmids, cosmids, viruses and bacteriophages used conventionally in genetic engineering, that comprise a nucleic acid molecule or an expression cassette of the invention. In a preferred embodiment of the invention, the vectors of the invention are suitable for the transformation of fungal cells, plant cells, cells of microorganisms (i.e. bacteria, protists, yeasts, algae etc.) or animal cells, in particular mammalian cells. Preferably, such vectors are suitable for the transformation of human cells. Methods which are well known to those skilled in the art can be used to construct recombinant vectors; see, for example, the techniques described in Sambrook and Russell (2001), loc. cit. Alternatively, the vectors may be liposomes into which the nucleic acid molecules or expression cassettes of the invention can be reconstituted for delivery to target cells. Likewise, the term "vector" refers to complexes containing such nucleic acid molecules or expression cassettes which furthermore comprise compounds that are known to facilitate gene transfer into cells such as polycations, cationic peptides and the like.

In addition to the nucleic acid molecule or expression cassette of the invention, the vector may contain further genes such as marker genes which allow for the selection of said vector in a suitable host cell and under suitable conditions. Generally, the vector also contains one or more origins of replication.

Advantageously, the nucleic acid molecules contained in the vectors are operably linked to expression control sequences allowing expression, i.e. ensuring transcription and synthesis of a translatable RNA, in prokaryotic or eukaryotic cells.

In one aspect, the expression of the nucleic acid molecules of the invention in prokaryotic or eukaryotic cells is interesting because it permits a more precise characterization of the function of the recombinant seven-transmembrane protein encoded by these molecules. In addition, it is possible to insert different additional mutations into the nucleic acid molecules by methods usual in molecular biology (see for instance Sambrook and Russell (2001), loc. cit.), leading to the synthesis of proteins possibly having modified properties, e.g. as concerns binding affinity or energy emission (e.g. RET) efficiency. In this regard, it is possible to mutate the nucleic acid molecules present in the vector by inserting or deleting coding sequences or to introduce amino acid substitutions by replacing the corresponding codon tripletts.

For genetic engineering, e.g. in prokaryotic cells, the nucleic acid molecules of the invention or parts of these molecules can be introduced into plasmids which permit mutagenesis or sequence modification by recombination of DNA sequences. Standard methods (see Sambrook and Russell (2001), loc. cit.) allow base exchanges to be performed or natural or synthetic sequences to be added. Similarly, for expression in eukaryotic cells, corresponding expression vectors, like pCDNA3 may be employed. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, sequence analysis, restriction analysis and other methods of biochemistry and molecular biology are carried out as analysis methods. The expression of the nucleic acid molecule of the present invention is preferably in a stable cell line. Procedure for selection of stably transfected cell lines are known in the art; see, inter alia, Vilardaga (2001), JBC 276, 33435-33443. Preferred host cells are CHO-cells, HEK293 cells, PC12 cells or even primary cells like primary cardiomyocytes or primary brain cells like cultured neurons, cerebral cortex astrocytes, dorsal root ganglia cells and the like.

In a further embodiment, the invention relates to a method for producing cells or hosts capable of expressing the recombinant seven-transmembrane protein/receptor of the invention comprising genetically engineering cells or hosts with an above-described nucleic acid molecule, expression cassette or vector of the invention.

Another embodiment of the invention relates to host cells, in particular prokaryotic or eukaryotic cells, genetically engineered with an above-described nucleic acid molecule, expression cassette or vector of the invention, and to cells descended from such transformed cells and containing a nucleic acid molecule, expression cassette or vector of the invention and to cells obtainable by the above-mentioned method for producing the same. As pointed out below, the invention also relates to non-human transgenic animals comprising nucleic acid sequences encoding the recombinant seven-transmembrane protein/receptor of the invention.

Preferably, host cells are bacterial, fungal, insect, plant or animal host cells. In a preferred embodiment, the host cell is genetically engineered in such a way that it contains the introduced nucleic acid molecule stably integrated into the genome. More preferably the nucleic acid molecule can be expressed so as to lead to the production of the recombinant seven-transmembrane protein of the invention.

A classical overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antoine von Leuwenhoek 67 (1995), 261-279), Bussineau (Developments in Biological Standardization 83 (1994), 13-19), Gellissen et al. (Antoine van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072). Particular preferred expression systems are described in the appended examples and in scientific references cited therein. Expression vectors have been widely described in the literature. As a rule, they contain not only a selection marker gene and a replication origin ensuring replication in the host selected, but also a bacterial or viral promoter and, in most cases, a termination signal for transcription. Between the promoter and the termination signal, there is in general at least one restriction site or a polylinker which enables the insertion of a coding nucleotide sequence. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of proteins. These promoters often lead to higher protein yields than do constitutive promoters. In order to obtain an optimum amount of protein, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (isopropyl-β-D-thiogalactopyranoside) (deBoer et al., Proc. Natl. Acad. Sci. USA 80 (1983), 21-25). Termination signals for transcription such as the SV40-poly-A site or the tk-poly-A site useful for applications in mammalian cells are also described in the literature. Suitable expression vectors are known in the art such as Okayama-Berg cDNA expression vector pcDV1 (Pharmacia), pCDM8, pRc/CMV, pcDNA1, pcDNA3 (Invitrogene; see also appended examples), pSPORT1 (GIBCO BRL)) or pCI (Promega).

The transformation of the host cell with a nucleic acid molecule or vector according to the invention can be carried out by standard methods, as for instance described in Sambrook and Russell (2001), loc. cit. The host cell is cultured in nutrient media meeting the requirements of the particular host cell used, in particular in respect of the pH value, temperature, salt concentration, aeration, antibiotics, vitamins, trace elements etc. The recombinant seven-transmembrane protein according to the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromography and lectin chromatography. In view of the possession of seven-transmembrane regions, the recombinant protein may be purified applying detergents, like TritonX-100 or SDS. Protein refolding steps can be used, as necessary, in completing the configuration of the protein. Such a purified recombinant protein may, inter alia, be reassembled and/or introduced into artificial biological membrane, like liposomes, crude membrane preparations or lipid bilayers.

Accordingly, a further embodiment of the invention relates to a method for producing the recombinant seven-transmembrane protein of the invention comprising culturing the above-described host cells under conditions allowing the expression of said recombinant protein and recovering said recombinant protein from the membranes of the host cell or host organism. Since the recombinant protein is localized in the membranes of the host cells, the protein can be recovered from the cultured cells by detergent-treatment.

Moreover, the invention relates to recombinant seven-transmembrane proteins which are obtainable by a method for their production as described above.

The recombinant seven-transmembrane protein of the present invention may, e.g., be a product of chemical synthetic procedures and is preferably produced by recombinant techniques from a prokaryotic or eukaryotic host (for example, by bacterial, yeast, higher plant, insect or mammalian cells in culture). Since the inventive protein is a membrane protein, it is preferably produced in a eukaryotic host cell or organism. Depending upon the host employed in a recombinant production procedure, the expressed protein may be modified, e.g. glycosylated or may be non-glycosylated, phosphorylated, palmytolated, ubiquitinated, methylated and the like. The recombinant protein of the invention may also include an initial methionine amino acid residue. The protein according to the invention may be further modified to contain additional chemical moieties not normally part of the protein. Those derivatized moieties may, e.g., improve the stability, solubility, the biological half life or absorption of the protein. The moieties may also reduce or eliminate any undesirable side effects of the protein and the like. An overview for these moieties can be found, e.g., in Remington's Pharmaceutical Sciences (18$^{th}$ edition, Mack Publishing Co., Easton, Pa. (1990)).

The present invention furthermore relates to non-human transgenic organisms, i.e. multicellular organisms comprising a nucleic acid molecule encoding a fusion protein of the invention or an expression cassette or vector as described above, preferably stably integrated into its genome, at least in a subset of the cells of that organism, or to parts thereof such as tissues or organs. Most preferably, such non-human transgene origin is a mammal like mouse, a rat, a sheep, a goat, a pig, a dog, a rat or a horse.

The transgenic animal expressing the recombinant seven-transmembrane protein of the present invention are particularly useful in pharmacological studies, screening and identification method as provided herein. It is of note that in particular for these studies not only cells but also organs or parts of organs of said non-human transgenic animals are particularly useful. It is envisaged that, for example brains or slice cultures of brain of the herein described non-human transgenic animal are employed in the screening and identification method provided herein. Besides the non-human transgenic animals which are mammals, it is also envisaged that said non-human transgenic organisms may be an amphibian, an insect, a fungi or even a plant. Particular preferred non-human transgenic animals in this context are *Drosphila, C. elegans, Xenopus* as well as yeasts like *S. pombe* or *S. cerevisae* or the *Aspergillus* species. Transgenic plants comprise, but are not limited to, wheat, tobacco, parsley or Arabidopsis.

As mentioned herein above and as in particular illustrated in the appended examples, the recombinant seven-transmembrane proteins defined herein are in particular useful in screening and identification methods for molecules or compounds which are capable of modifying the biological and/or pharmacological action of seven-transmembrane proteins, in particular of GPCRs and proto-oncogenes. As the examples show, the present invention is based on the surprising finding that intramolecular RET-analysis can be carried out on rather complex proteins comprising seven-transmembrane regions. It was in particularly surprising that recombinant seven-transmembrane proteins as defined herein provide for a direct measurement system to investigate activation (or de-activation) of GPCR in very fast time frames. The prior art, like Gether (1995), JBC 270, 28268-28275; Jensen (2001), JBC 276, 9279-9290, Ghanouni (2001), JBC 276, 24433-24436 or Ghanouni (2001), PNAS 98, 5997-6002 has provided for screening methods comprising spectroscopic studies where, inter alia, agonists-mediated changes in GPCRs could be measured on a minute time scale. This is much slower than the biological responses to receptor activation which can occur within seconds, even milliseconds. Accordingly, the present invention provides for the first time means and methods whereby activation (as well as de-activation) of seven-transmembrane proteins, in particular GPCRs may be observed with a high resolution and within physiological kinetics. In particular, high resolution assays for conformational changes/switches of receptor activation in living cells are provided.

Accordingly, the present invention provides in one embodiment a method for identifying molecules or compounds which are capable of activating, deactivating or inactivating the (biological/pharmacological) function of (a) seven-transmembrane receptor(s), comprising the steps of (a) contacting the recombinant seven-transmembrane receptor, a host or a host cell as defined herein with (a) molecule(s) or compound(s) to be tested; and (b) measuring as a response whether said molecule(s) or compound(s) to be tested lead(s) to a modification of a signal provided by said at least two detectable labels.

Furthermore, a method of screening for molecules or compounds which are activators (agonists) or inhibitors (antagonists) of the (biological/pharmacological) function of (a) seven-transmembrane receptor(s) is provided, said method comprising the steps of (a) contacting a recombinant seven-transmembrane receptor, a host or a host cell as defined herein with the molecule or compound to be tested;
(b) measuring and/or detecting a response comprising a modification of a signal provided by said at least two detectable labels; and
(c1) comparing said response to a standard response as measured in the absence of said candidate molecule/compound;
(c2) comparing said response to the response of a control membrane receptor which comprises at least two detectable labels on the C-terminus; or
(c3) comparing said response to control seven-transmembrane receptor which comprises only one detectable label.

Similarly, the invention provides for a method for identifying molecules or compounds which are capable of eliciting a (biological/pharmacological) response of (a) seven-transmembrane protein(s), comprising the steps of (a) contacting a recombinant seven-transmembrane protein, a host or host cell of the invention with the molecule or compound to be tested; and
(b) identifying among these molecules/compounds the molecules/compounds which are capable of eliciting a change in energy emitted by said at least two detectable labels comprised on the recombinant membrane receptor as defined above.

According to the methods provided herein, the invention provides for identifying, characterizing, screening as well as derivatized molecules which are capable of interacting with seven-transmembrane protein, in particular with GPCRs or proto-oncogenes, whereby said interaction may lead to an activation, a partial activation, an inhibition or a partial inhibition of the biological and/or pharmacological function of said seven-transmembrane protein. Therefore, the present invention provides for distinct screening as well as identification methods for agonists, partial agonists, inverse agonists as well as antagonists of seven transmembrane receptors, in particular of GPCRs. In context of this invention as well as in accordance with the pharmacological sciences, the term "agonist" can be confined as a molecule or a compound that binds to and activates the corresponding receptor. As "partial agonists" the art defines molecules/compounds that behave like agonists, but that, even at high concentrations, cannot activate the receptors to the same maximal extend as full agonists. The term "inverse agonist" relates to molecules/compounds that bind to and inhibit activity of the corresponding receptor. These inverse agonists are of particular importance and visible, when the receptors exhibit intrinsic agonist-independent activity. Inverse agonism is a process by which a ligand reduces or suppresses the basal activity of a receptor that activates for example the endogenous G protein activation in the absence of agonist binding (Trends Pharmacol Sci 2002, 23(2):89-95). A long-standing question on the pharmacology of seven-transmembrane receptors, in particular of GPCRs, is how inverse agonists act on receptors and what is the nature of the conformational change mediated by inverse agonists on said receptors. To characterize the mechanism by which inverse agonists generate a conformational change within the receptor, recombinant seven-transmembrane receptors as described in the present invention have been employed. As documented in the appended examples, an illustrative recombinant $\alpha_{2A}$-adrenergic receptor ($\alpha_{2A}$AR-cam) was employed, whereby said $\alpha_{2A}$-adrenergic receptor ($\alpha_{2A}$AR-cam) comprises the two detectable labels YFP and CFP on the first intracellular loop and the third intracellular loop. The fluorescence resonance energy transfer (FRET) was recorded in living neural cells in presence of an agonist (noradrenaline) and two distinct well established inverse agonists (yohimbine and rauwolscine, Mol. Pharmacol. 2001, 59:532-542) (see, inter alia, FIG. 14). The data as documented in the appended examples show that agonists and inverse agonists transduce opposite conformational changes of the receptor. Thus, "sensors", i.e. the recombinant seven-transmembrane receptors, of the present invention are particularly useful for differentiating between agonists and inverse agonists at the receptor level.

The term "antagonist" relates to molecules/compounds that bind to receptors but do not alter the intrinsic activity of said receptor. They may also prevent binding of the corresponding receptor ligand and they may prevent the binding and activation of the receptors by their agonists or partial agonists.

In accordance with the present invention, the term "antagonist" denotes molecules/substances, which are capable of inhibiting and/or reducing an agonisitic effect. The term "antagonist" comprises competitive, non-competitive, functional and chemical antagonists as described, inter alia, in Mutschler, "Arzneimittelwirkungen" (1986), Wissenschaftliche Verlagsgesellschaft mbH, Stuttgart, Germany. The term "partial antagonist" in accordance with the present invention means a molecule/substance that is capable of incompletely blocking the action of agonists through, inter alia, a non-competitive mechanism. As "agonist", in accordance with this invention, molecules/substances are denoted which have an affinity as well as an intrinsic activity. Mostly, said intrinsic activity ($\alpha$) is defined as being proportional to the quotient of the effect, triggered by said agonist ($E_A$) and the effect which can be maximally obtained in a given biological system ($E_{max}$): therefore, the intrinsic activity can be defined as $$\alpha \sim \frac{E_A}{E_{max}}$$

The highest relative intrinsic activity results from $E_A/E_{max}=1$. Agonists with an intrinsic activity of 1 are full agonists, whereas substances/molecules with an intrinsic activity of >0 and <1 are partial agonists. Partial agonists show a dualistic effect, i.e. they comprise agonistic as well as antagonistic effects.

The person skilled in the art can, therefore, easily employ the compounds and the methods of this invention in order to elucidate the agonistic and/or antagonistic effects and/or characteristics of a compound/molecule/substance to be identified and/or characterized in accordance with any of the above described methods.

The identification and/or characterization of molecules which are capable of interacting with seven-transmembrane receptors, may be, inter alia, achieved by transfecting an appropriate host with a nucleic acid molecule encoding the same and as defined above. Said hosts comprise, but are not limited to, HEK 293 cells, CHO-cells, (primary) cardiomyocytes, (primary) cultured nerve cells, or frog oocytes. After expression of a recombinant seven-transmembrane protein of the invention, membrane currents may be deduced in the absence and/or presence of the molecule to be identified and/or characterized. Methods for the deduction of membrane currents are well known in the art and comprise, e.g., patch clamp methods as described in Hamill, Pfluger's Arch. 391 (1981), 85-100 or two-electrode voltage clamp in oocytes, as described in Methfessel, Pflügers Archive 407 (1986) 577-588.

However, as the appended examples illustrate, the particular preferred measurement methods comprise the FRET- or BRET-measurements as will be detailed below. Yet, also GIRK current measurements are envisaged and shown in the appended examples.

Furthermore, the present invention relates to a method of screening for molecules which are capable of interacting with seven-transmembrane proteins, comprising the steps of (a) contacting a recombinant seven-transmembrane protein of the invention or as encoded by a nucleic acid molecule, a vector or a host of the invention with a candidate molecule; and (b) measuring and/or detecting a response; and (c) comparing said response to a standard response as measured in the absence of said candidate molecule.

Potential candidate molecules or candidate mixtures of molecules may be, inter alia, substances, compounds or compositions which are of chemical or biological origin, which are naturally occurring and/or which are synthetically, recombinantly and/or chemically produced. Thus, candidate molecules may be proteins, protein-fragments, peptides, amino acids and/or derivatives thereof or other compounds, such as ions, which bind to and/or interact with, inter alia, GPCRs.

A person skilled in the art will immediately appreciate that the methods of the invention may present an important contribution to pharmacological research, in particular in the field of drug screening. Thus, corresponding techniques for drug screening described in the literature are incorporated herein by reference. This includes for instance Kyranos (Curr. Opin. Drug. Discov. Devel. 4 (2001), 719-728), Pochapsky (Curr. Top. Med. Chem. 1 (2001), 427441) and Bohets (Curr. Top. Med. Chem. 1 (2001), 367-383).

According to the present embodiment, in principle any kind of cell, membrane, membrane preparation or liposome may be used for the present method that is amenable to optical detection. The cell to be used can be transformed so as to express a heterologous protein, i.e. the recombinant seven-transmembrane protein of the present invention. Thus, the cells may be single cells such as bacteria, yeasts, protozoa or cultured cells, e.g., of vertebrate, preferably mammalian, more preferably human origin. For certain applications, it may be useful to take pathogenetically affected cells such as tumor cells or cells infected by an infectious agent, e.g. a virus, wherein preferentially measurements are conducted in comparison with corresponding healthy cells. Likewise, the cells may be part of a tissue, organ or organism, in particular of a non-human transgenic animal defined above.

The candidate compounds or test compounds can in principle be taken from any source. They may be naturally occurring substances, modified naturally occurring substance, chemically synthesized substances or substances produced by a transgenic organism and optionally purified to a certain degree and/or further modified. Practically, the candidate compound may be taken from a compound library as they are routinely applied for screening processes.

The term "contacting" refers to the addition of a candidate compound/test compounds to the analyzed cell in a way that the compound may become effective to the cell at the cell surface or upon cellular uptake. Typically, the candidate compound or a solution containing it may be added to the assay mixture. Step (a) of the methods of the present invention, i.e. the "contacting step" may likewise be accomplished by adding a sample containing said candidate compound or a plurality of candidate compounds to the assay mixture. If such a sample or plurality of compounds is identified by the present method to contain a compound of interest, then it is either possible to isolate the compound from the original sample or to further subdivide the original sample, for example, if it consists of a plurality of different compounds, so as to reduce the number of different substances per sample and repeat the method with the subdivisions of the original sample. Depending on the complexity of the sample, the steps described herein can be performed several times, preferably until the sample identified according to the method of the invention only comprises a limited number of or only one substance(s). Preferably said sample comprises substances of similar chemical and/or physical properties, and most preferably said substances are identical.

Step (b), i.e. the "measuring or identification step" may be carried out in accordance with the explanations regarding measuring a change in energy emission of the fusion proteins of the invention as given hereinabove. Particularly preferred are optical measurement techniques that allow a resolution of fluorescence on the level of single cells, preferably at the subcellular level. Suitable imaging techniques are described in the literature such as in Periasamy A., Methods in Cellular Imaging, 2001, Oxford University Press or in Fluorescence Imaging Spectroscopy and Microscopy, 1996, edited by: X. F. Wang; Brian Herman. John Wiley and Sons. They may involve fluorescence, preferably confocal, microscopy, digital image recording, e.g. by way of a CCD camera, and suitable picture analysis software. The appended examples also provide for useful settings for measuring candidate compounds. Preferentially, step (b) is carried out by running parallel control experiments. For instance, a corresponding cell expressing the same recombinant seven-transmembrane protein may be observed under corresponding conditions as in steps (a) and (b), however, without contacting a candidate compound.

Accordingly, potential candidate molecules may be contacted with a cell, such as an oocyte, a HEK 293 cell, a CHO cell, a PC12 cell, or an (primary) cardiomyocytes which express a recombinant seven-transmembrane protein of the invention or with a membrane patch, a membrane preparation, comprising a recombinant seven-transmembrane protein of the invention and measuring a corresponding response (inter alia, a dose-response, a current-response, or a concentration response) in order to elucidate any effect said candidate molecule causes. Said response is most preferably measured by methods provided herein and in particular by FRET or BRET technology.

Within the scope of the present invention are also methods for identifying, characterizing and for screening of molecules which are capable of interacting with seven-transmembrane receptors which comprise so-called high-throughput screening methods and similar approaches which are known in the art (Spencer, Biotechnol. Bioeng. 61 (1998), 61-67; Oldenburg, Annu. Rep. Med. Chem. 33 (1998), 301-311; Milligan, Trends Pharmacol. Sci. 20 (1999), 118-124) carried out using 96-well, 384-well, 1536-well (and other) commercially available plates. Further methods to be employed in accordance with the present invention comprise, but are not limited to, homogenous fluorescence readouts in high-throughput screenings (as described, inter alia, in Pope, Drug Discovery Today 4 (1999), 350-362). The method of the present invention for identification, characterization and/or screening of molecules capable of interacting with seven transmembrane-proteins, in particular GPCRs, can, inter alia, employ hosts as defined herein which express the recombinant protein of the present invention. Cell-based assays, instrumentation for said assays and/or measurements are well-known in the art and described, inter alia, in Gonzalez, Drug Discovery Today 4 (1999), 431-439 or Ramm, Drug Discovery Today 4 (1999), 401-410.

In this context, it is envisaged that agonists as well as antagonists as defined herein may be verified, measured and/or deduced by the methods provided herein. It is also envisaged that modifications, derivatives and the like of known agonists and/or antagonists are measured and screened by the methods of the present invention. For example, the activity of a derivate/derivative of a known agonist or antagonist of a GPCR may be compared to the activity of the corresponding, non-modified (not-derivatized) agonist/antagonist. As non-limiting examples the following list provides for antagonists/agonists of the exemplified GPCRs α2A-adrenergic receptor, PTH-receptor and A2A adenosine receptor. Also provided are pharmaceutical/medical uses of the corresponding agonists/antagonists.

1. $\alpha_{2A}$-Adrenergic Receptor:
Compounds:
Agonists: clonidine and similar drugs (centrally acting antihypertensive; treatment of withdrawal syndrome, open angle glaucoma, diarrhea in patients with neuropathies); oxymetazoline and many similar drugs (direct vasoconstrictor: decongestion in rhinitis, conjunctivitis etc); apraclonidine, brimonidine (open angle glaucoma); dexmedetomidine (anaesthetic, sedative).

Possible further medical use: psychiatric and neurologic (presynaptic inhibition of neurotransmitter release)

Antagonists: Phentolamine (peripherally acting antihypertensive, particularly in pheochromocytoma)

Possible further medical use: psychiatric (presynaptic desinhibition), functional treatment of degenerative CNS diseases Diseases (in addition to those mentioned above) to be treated by agonists comprise Risk factor in cardiovascular diseases (increased release of neurotransmitter if receptor dysfunctional: hypertension, heart failure; in CNS-dysfunctions, agonists and antagonists are envisaged)

2. PTH-Receptor:
Agonists: parathyroid hormone (PTH) itself and smaller fragments thereof, e.g. PTH(1-34) (hypoparathyroidism, osteoporosis, diagnostic use in different forms of hypoparathyroidism).

Antagonists: Small fragments of. PTH, e.g. PTH(7-34) possible medical use: hyperparathyroidism Diseases (in addition to those mentioned above) to be treated by agonists comprise diseases of vitamin-D-metabolism, Ca-homeostasis; diseases of defective bone formation or metabolism (like osteoporosis)

3. $A_{2A}$ Adenosine Receptor:
Agonists: Adenosine and several of its purine modified derivatives, e.g. N-ethylcarboxamidoadenosine (NECA);
Effects: Vasodilation, inhibition of platelet aggregation, various CNS-effects.

Possible medical use: disorders of platelet aggregation and consequences of such disorders (atherosclerosis, stroke, myocardial infarction, heart failure), vasodilation for hypertension, vasospasm, various psychiatric/neurological illnesses have been postulated as potential indications.

Antagonists: theophylline, caffeine and other methylxanthines

Bronchial asthma—bronchodilation, central stimulation, diuresis, apnea—particularly in infants (not actually proven that this receptor subtype is the target in these therapeutic effects—other homologous adenosine receptors ($A_1$, $A_{2B}$, $A_3$) might also be involved)

possible medical use: disorders of attention such as e.g. ADHS

Further GPCRs to be modified in form of recombinant seven-transmembrane receptors of the present invention comprise, but are not limited to: $\beta_1$-, $\beta_2$-, $\beta_3$-, $\alpha_{1A, B, \Delta}$-, $\alpha_{2A,B}$, x-adrenergic receptor; $M_{1-5}$ muscarinic receptor; $H_1$-, $H_2$-histamine receptor, $AT_1$-angiotensin receptor; serotonin-receptor(s) as well as opiate receptors. Corresponding agonists/antagonists and medical indications are given in the following table. Again it is envisaged that derivatives and/or modifications of the given agonists/antagonists be tested by the methods provided herein.

| Receptor | Agonists (Indication) | Antagonists (Indication) |
|---|---|---|
| Adrenergic | | |
| $\beta_1$ | Noradrenaline, adrenaline, dobutamine (cardiac shock, acute heart failure) | metoprolol, bisoprolol and many others (hypertension, arrhythmias, heart failure, myocardial infarction) |
| $\beta_2$ | Isoprenaline, terbutaline, salbutamol and many others (bronchial asthma - bronchodilation, premature labour) | propranolol and many others (as for $\beta_1$; also: open angle glaucoma, hyperthyroidism, tremor, some forms of anxiety) |
| $\beta_3$ | Isoprenaline, several experimental compounds, e.g. BRL37344 (lipolysis) | several experimental compounds, e.g. ICI118551 |
| $\alpha_{1A,B,\Delta}$ | Noradrenaline, adrenaline, phenylephrine (Constriction of smooth muscle, eg. vasoconstriction, activation of gastrointestinal smooth muscles) | prazosin, terazosin, tamsulosin and others (hypertension, prostatism) |
| $\alpha_{2A,B,X}$ | Noradrenaline, adrenaline, clonidine, oxymetazoline (see above) | yohimbin (use as aphrodisiac) |
| Muscarinic | | |
| $M_{1-5}$ | Acetylcholine, carbachol, pilocarpine (glaucoma, activation of gastrointestinal motility, tacharrhythmias | Atropine, scopolamine (bradycardia, (pre-) anasthesia, bronchial asthma, vagal reflexes, poisoning with E605 and similar compounds including nerve gas) |
| Histamine | | |
| $H_1$ | histamine | loratadine, clemastine (antiallergic, sedative-hypnotic) |
| $H_2$ | histamine | ranitidine and many others (gastric acid secretion: gastric and duodenal ulcers) |
| Angiotensin | | |
| $AT_1$ | angiotensin | losartan (antihypertensive) |
| Serotonin (5-HT) 14 receptor sutypes, e.g.: | | |
| 5-$HT_{1B/D}$ | sumatriptan and others (migraine) | |
| 5-$HT_{2C}$ | | methysergide, pizotifen (migraine, carcinoid syndrome) |

-continued

| Receptor | Agonists (Indication) | Antagonists (Indication) |
|---|---|---|
| 5-HT$_4$ | partial agonists: metoclopramide (gastrointestinal motility disorders) | |
| Opiate | | |
| μ | morphine and many others (analgesia, CNS-stimulation (euphoria) and depression, alterations in smooth muscle contraction: increase-spasm/decrease) | naloxone, naltrexone Treatment of opiate overdose, termination of opiate effects |
| κ | ethylketocyclazozine and many others (analgesia, diuresis, central nervous system effects) | naloxone, naltrexone as above |
| δ | etorphine, deltorphin and others (analgesia, alterations in smooth muscle contraction: decrease) | naloxone, naltrexone as above |

Additionally, the present invention relates to a method for the production of a pharmaceutical composition comprising the steps of the method of the invention for identifying, characterizing and/or screening of molecules which are capable of interacting with seven-transmembrane receptors, like GPCRs, and further comprising a step, wherein a derivative of said identified, characterized and/or screened molecule is generated. Such a derivative may be generated by, inter alia, peptidomimetics.

The invention furthermore relates to a method for the production of a pharmaceutical composition comprising the steps of the method of the invention for identifying, characterizing, screening and/or derivatizing of molecules which are capable of interacting with seven-transmembrane receptors, like GPCRs and formulating the molecules identified, characterized, screened and/or derivatized in pharmaceutically acceptable form.

In a preferred embodiment, the response or energy changes to be measured in the methods provided herein correspond to an increase or a decrease of fluorescence resonance energy transfer (FRET).

In FRET, both donor and acceptor, i.e. both detection portions, are fluorescent protein portions and, for measuring FRET, the fusion protein is supplied with energy, i.e. radiation, appropriate for exciting energy emission by the first detection portion.

Accordingly, it is a preferred embodiment of the recombinant seven-transmembrane protein of the present invention, that the first detection label is a fluorescent protein portion.

The efficiency of FRET is dependent on the distance between the two fluorescent partners. The mathematical formula describing FRET is the following: $E=R_0^6/(R_0^6+r^6)$, where E is the efficiency of FRET, r is the actual distance between the fluorescent partners, and $R_0$ is the Förster distance at which FRET is 50% of the maximal FRET value which is possible for a given pair of FRET partners. $R_0$, which can be determined experimentally, is dependent on the relative orientation between the fluorescent partners (κ), refractive index of the media (n), integral overlap of the emission of the donor with the excitation of the acceptor partner (J(λ)), and the quantum yield of the fluorescent donor partner ($Q_D$) ($R_0^6=8.79\times10^{-25}[\kappa^2 n^{-4} Q_D J(\lambda)]$ (in cm$^6$)). In classical FRET based applications the orientation factor $\kappa^2$ is assumed to equal ⅔, which is the value for donors and acceptors that randomize by rotational diffusion prior to energy transfer (Lakovicz, Principles of Fluorescence spectroscopy, second edition, page 370). Thus, at randomized rotational diffusion, the change in ratio is assumed to be only due to a change in distance between the chromophores. For perpendicular dipoles $\kappa^2$ is 0.

In accordance with the appended examples, a decrease in FRET-signal can be determined by the following equation: $r(t)=A\times(1-e^{-t/\tau})$, where τ is the time constant (s) and A is the magnitude of the signal. When necessary for calculating τ, agonist-independent changes in FRET due to photobleaching were subtracted. In order to apply FRET for detection of agonists, antagonists, partial agonists and partial antagonists as well as inverse agonists, the person skilled in the art is capable of selecting suitable detection labels (defined above) for the seven-transmembrane protein of the invention that show a detectable FRET and a detectable change of FRET upon a conformational change in its structure. Preferably, maximum FRET efficiency is at least 5%, more preferably at least 50% and most preferably 80% of the energy released by the first detection label upon excitation. Additionally, the two detection labels need to have a spectral overlap. The greater the overlap of the emission spectrum of the donor with the absorption spectrum of the acceptor, the higher is the value of $R_0$. Acceptors with larger extinction coefficients lead to higher $R_0$ values. In contrast, the overlap in excitation spectra of both detection portions should be small enough to prevent coexcitation of the acceptor chromophore. Likewise, the spectra of both detection portions should only overlap to an extent that discrimination between the two emission signals is still possible.

As detailed in the appended examples, in a particularly preferred embodiment, the first detection portion is cyan fluorescent protein (CFP) and the second detection portion is enhanced yellow fluorescent protein (eYFP).

It has been shown that CFP and YFP are particularly well suited for the recombinant membrane protein of the present invention since they show an efficient change in FRET. CFP and eYFP are well known in the art and nucleic acid molecules containing corresponding coding sequences are commercially available e.g. from Clonetech. Said nucleic acid sequences are also shown in appended SEQ ID NOS: 7 to 10.

In a further preferred embodiment of the present invention the methods provided herein are based on the detection of responses or energy changes which comprise an increase or a decrease of bioluminescent resonance energy transfer (BRET). BRET-technology is very well known in the art and, inter alia, described in Angars, (2000) PNAS 97, 3684-3689; in Mercier (2002), JBC 277, 44925-44931; in Barcock, (2003), JBC 278, 3378-3385 or in WO 99/66324. As pointed out herein above a preferred bioluminescent protein is renilla luciferase but also firefly luciferase may be employed. As a preferred fluorescent protein portion in the recombinant seven-transmembrane receptor of the present invention comprising renilla luciferase as a first detection system, enhanced yellow fluorescent protein or yellow fluorescent protein may be employed.

In accordance with the methods provided herein in a most preferred embodiment, the recombinant seven-transmembrane protein of the present invention is located, respectively inserted, into a biological membrane. Most preferably, said biological membrane is a plasma membrane of a cultured cell or is a membrane in (a) cell(s) of an organ or tissue of a non-human transgenic animal expressing the recombinant seven-transmembrane protein of the present invention. Further embodiments of the remaining and/or identification methods of the present invention are given and illustrated in the appended examples. It is of note that in context of the present invention several control as already briefly discussed herein above may be employed. For example, recombinant seven-transmembrane proteins comprising only one detectable label may be used as controls. Such recombinant protein will not provide for any change in energy emitted or to a detectable response which may be measured. Accordingly, the test molecules or test compounds or samples comprised either alone or in combination such molecules or compounds may be tested in parallel experiment on recombinant seven-transmembrane proteins of the present invention, capable of eliciting a distinct response upon conformational change and recombinant seven-transmembrane receptors which only comprise one of the above-identified detectable labels and are, accordingly, not capable of eliciting a corresponding signal, in particular of eliciting an resonance energy transfer. Another control protein to be employed in accordance with the method of the present invention is the recombinant seven-transmembrane receptor protein which comprises both detectable labels on the C-terminus. Such a control protein is, inter alia, illustrated in appended SEQ ID NO: 38 and was employed in accordance with this invention in the appended examples. This control molecule leads to strong resonance energy transfer. However, upon testing with corresponding ligands, specific for the seven-transmembrane receptor to be tested no further chain of the RET is expected. For example, the here defined control for a PTH receptor comprising both detectable labels in the carboxy terminal provides for a strong FRET signal which does not change when the corresponding ligand, namely parathyroid hormone is applied.

The invention also provides for a diagnostic composition comprising the recombinant membrane protein, the nucleic acid molecule, the vector, the host cell or the organs or cells of the non-human transgenic animal of the invention. Such a diagnostic composition is particularly useful in the methods of the present invention. Similarly, kits are provided which comprise the compounds of the invention, in particular; the recombinant membrane protein, the nucleic acid molecule, the vector, the host cell or the organs or cells of the non-human transgenic animal of the invention.

Finally, the invention relates to the use of the recombinant membrane protein or the nucleic acid molecule, the vector, the host cell or the organs or cells of the non-human transgenic animal of the invention for the detection of (a) modifier(s) of the biological activity of seven-transmembrane receptors in vivo or in vitro.

The embodiments of the method(s) of the invention apply here mutatis mutantis.

BRIEF DESCRIPTION OF THE DRAWINGS

FIG. 1 Part 1: FRET efficiency and time-resolved changes in the FRET signal of PTHR-cam. (A) Overall transmembrane topology of the GPCR-cam constructs.

(B) Fluorescence emission spectra of selected PTHR constructs. Shown are the emission spectra of PTHR-CFP$_{3\text{-}loop}$ (blue), PTHR-YFP$_{C\text{-}term}$ (yellow) and PTHR-cam (red) upon excitation at 433 nm. (C) Effects of photobleaching. Emission intensities of YFP (535 nm, yellow) and CFP (480 nm, blue) were recorded simultaneously from single cells expressing PTHR-cam using fluorescence microscopy. Emission intensities were recorded before and after the acceptor fluorophore was photobleached by 5 min exposure to light at 480 nm. (D) Time-resolved changes in the ratio $F^*_{535}/F^*_{480}$ in single HEK293 cells stably expressing PTHR-cam. Emission intensities of YFP (535 nm, yellow), CFP (480 nm, blue) and the ratio $F^*_{535}/F^*_{480}$ (red) were recorded simultaneously from single cells. Shown are the changes induced by rapid superfusion with 1 µM PTH (arrow). The decrease of the ratio $F^*_{535}/F^*_{480}$ was fitted by a simple mono-exponential curve giving a time-constant in this experiment of 3.5 s. Changes in the ratio are expressed as % decrease from the initial value at t=0 s.

FIG. 1, Part 2: Guanine nucleotide sensitivity of agonist binding at the $\alpha_{2A}$AR-cam stably expressed in HEK-293 cells. In the presence of exogenous $G_o$ protein (at a molar ratio 1:100, receptor:$G_o$) the binding affinity for the $\alpha_{2A}$AR agonist UK14,304 for membranes containing $\alpha_{2A}$AR-cam decreases ≈3-fold in presence of 10 µM GTPγS ($K_d$=3.4±0.8 nM vs $K_d$=9.6±1.1 nM, n=3) reflecting the shift of the receptor population to a lower affinity state.

FIG. 2: Pharmacological properties of the GPCR-cam constructs.

(A-B) Comparison between the binding and signalling properties of PTHR-cam (A), $\alpha_{2A}$-AR-cam (B) and their respective wild type receptor stably expressed in HEK293 cells. The expression level of the receptors were $1.01 \times 10^6$ and $0.34 \times 10^6$ receptors/cells for PTHR and PTHR-cam, respectively; 24 and 6 pmol/mg for $\alpha_{2A}$AR and $\alpha_{2A}$AR-cam, respectively. The data are the means±S.E. of at least 4 separate experiments carried out in duplicate. (C) Visualization PTHR-cam stably expressed in HEK293 cells by confocal microscopy.

Figure 3:
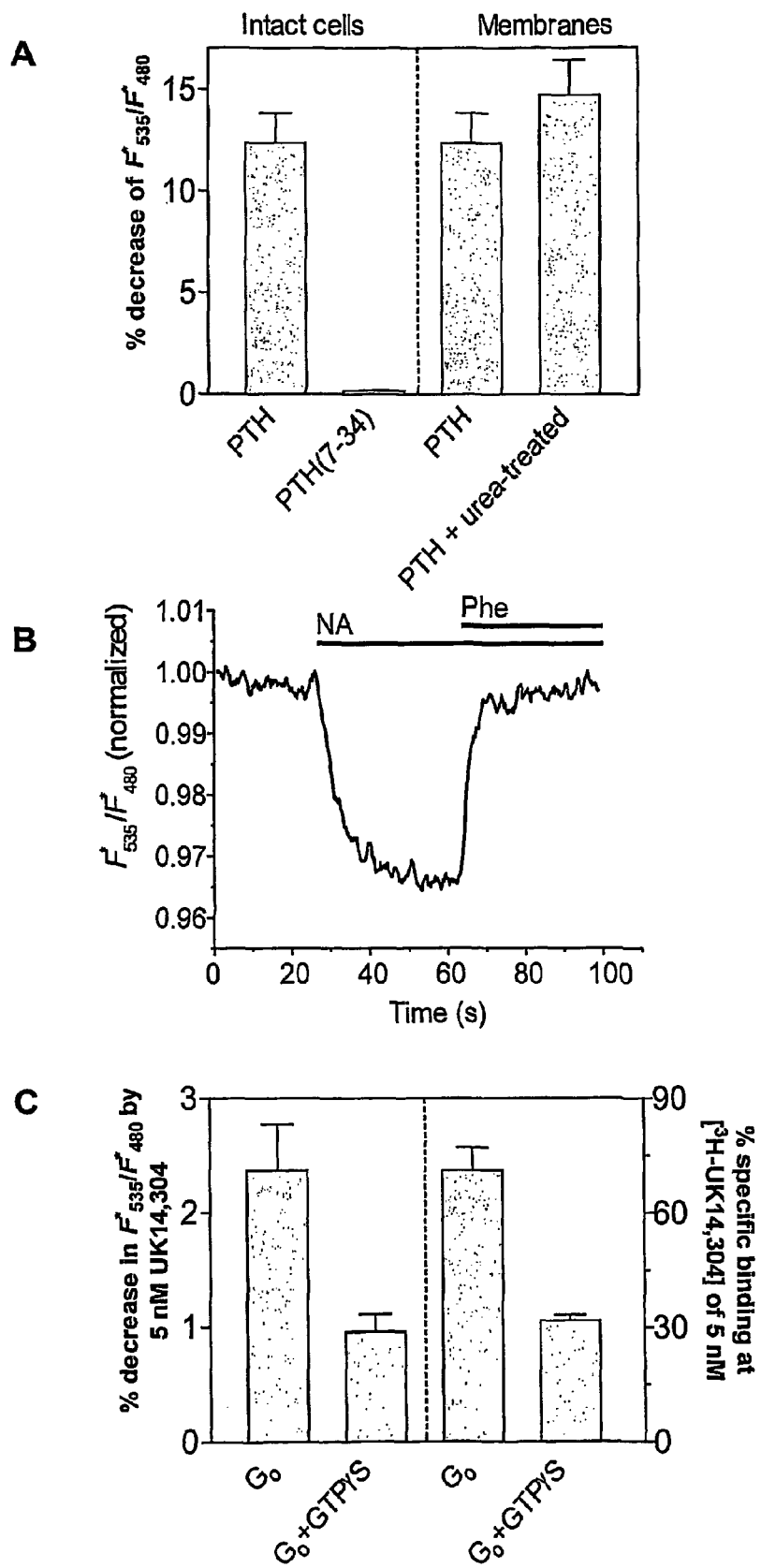

FIG. 3: Agonist-induced decrease in FRET signal corresponds to receptor activation. (A) Intact cell panel shows the effects of the agonist PTH (1 µM) and the antagonist PTH(7-34) (3 µM) on the ratio $F^*_{535}/F^*_{480}$ of PTHR-cam in intact HEK293 cells. Membranes panel shows the effects of PTH (1 µM) in cell membranes prepared from HEK293 cells stably expressing PTHR-cam. The membranes were measured either without further treatment (left), or after treatment with 6 M urea (right). Bars represent the % decrease in the ratio $F^*_{535}/F^*_{480}$ upon PTH exposure. (B) Effect of the antagonist phentolamine (10 µM) on the FRET signal caused by 10 µM noradrenaline (NA) in HEK293 cells stably expressing $\alpha_{2A}$AR-cam (n=4). (C) Comparison of the guanine nucleotide sensitivity of the FRET signal (left panel) and agonist binding (right panel) evoked by sub-saturating concentration of UK14304 in membranes containing $\alpha_{2A}$AR-cam in the presence of $G_o$ proteins (ratio receptor:$G_o$ 1:100) with or without GTPγS (10 µM). Data are the means±S.E. of at least 4 separate experiments.

Figure 4:
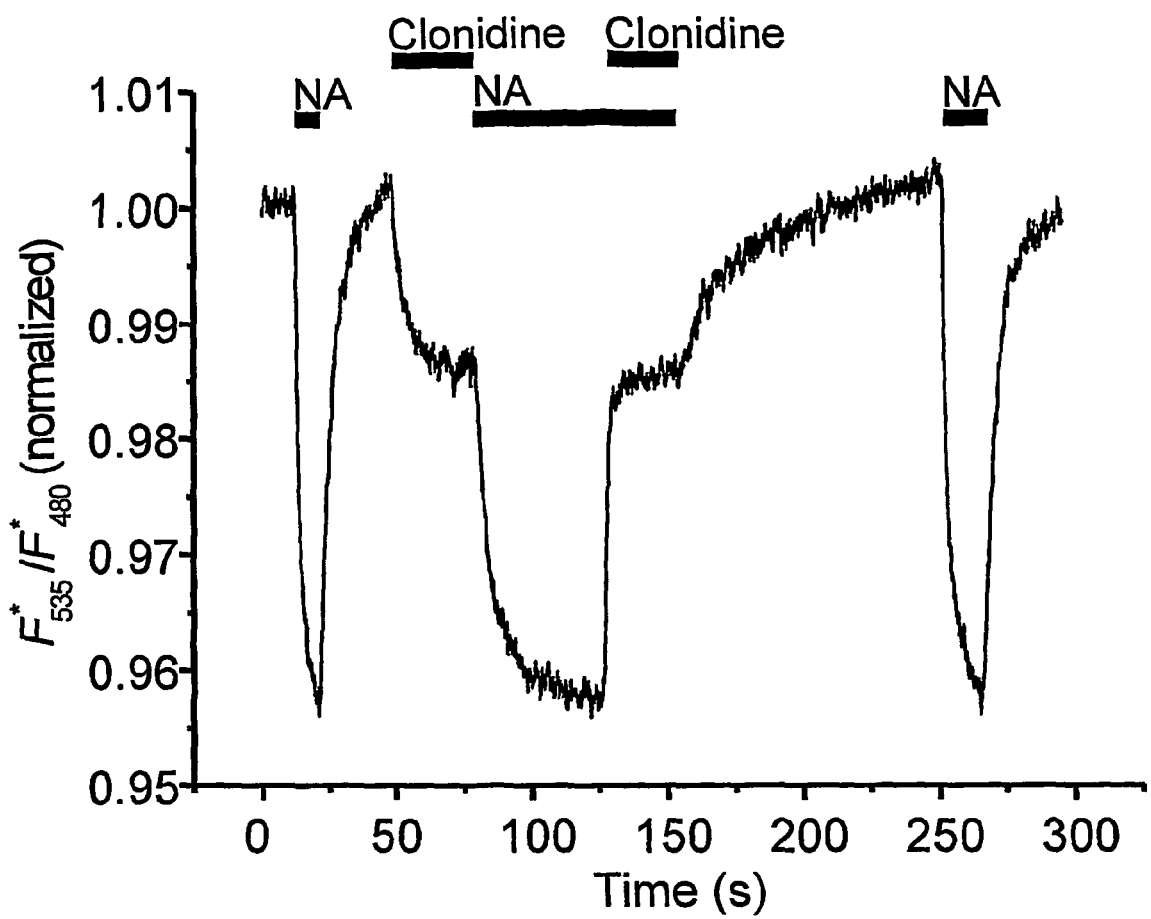

FIG. 4: Action of the partial agonist clonidine on $\alpha_{2A}$AR-cam. Changes in FRET in response to 10 µM noradrenaline (NA) or 10 µM clonidine added alone or together were recorded in a single HEK293 cell expressing $\alpha_{2A}$AR-cam. The recording is representative of 4 independent experiments.

Figure 5:
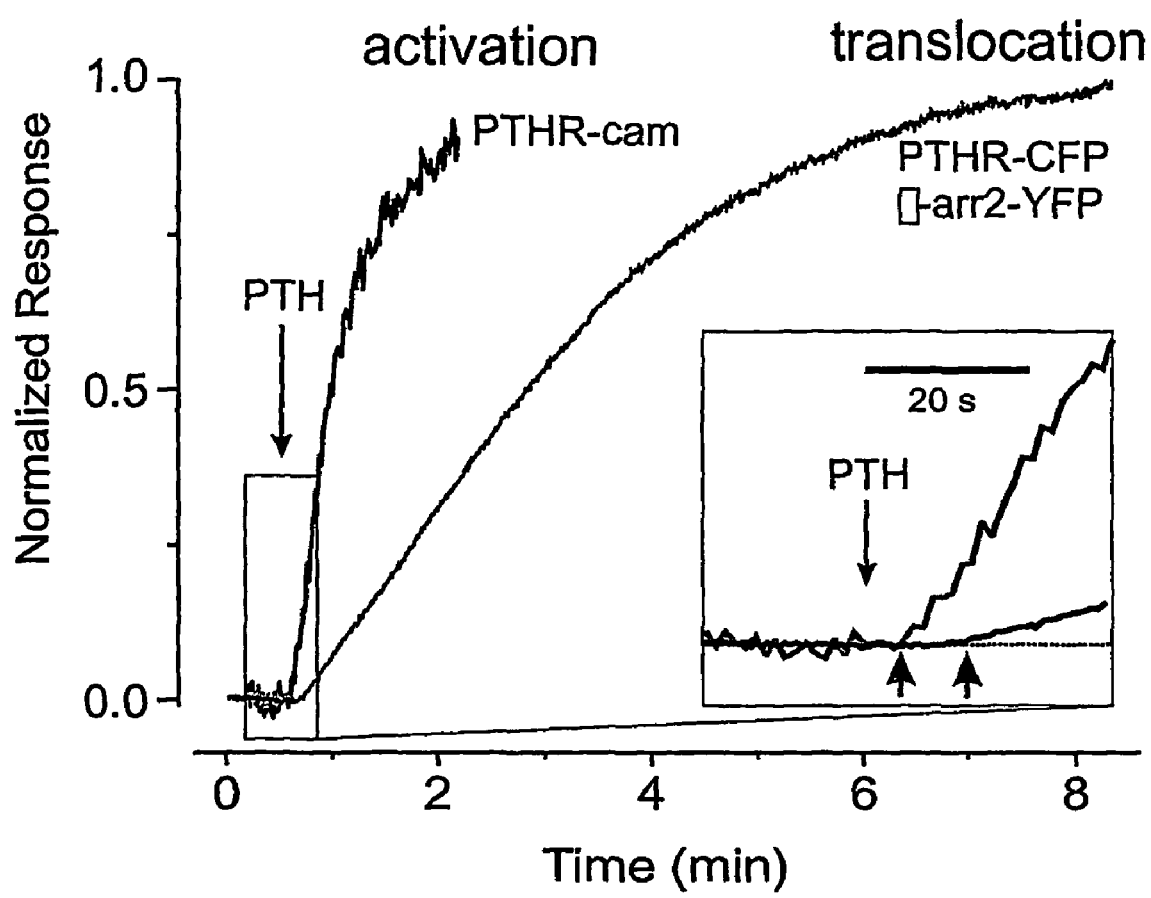

FIG. 5: Comparison between the dynamics of receptor activation and desensitization of PTHR-cam. The kinetics of activation of PTHR-cam and of β-arrestin2-YFP binding to the PTHR-CFP$_{c\text{-}term}$ were measured as changes in the ratio $F^*_{535}/F^*480$ in single cells expressing PTHR-cam or co-expressing PTHR-CFP$_{C\text{-}term}$ and β-arrestin2-YFP in response to 100 nM PTH. The recordings are expressed as % of the respective maximal response and are representative of at least 3 independent experiments. Note that in the case of PTHR-CFP$_{C\text{-}term}$/β-arrestin2-YFP the ratio $F^*_{535}/F^*_{480}$ does indeed increase, while in the PTHR-cam the ratio decreases and is depicted as a positive signal just to facilitate the comparison of the kinetics. The inset represents a time scale expansion to illustrate the differences in response delays.

Figure 6:
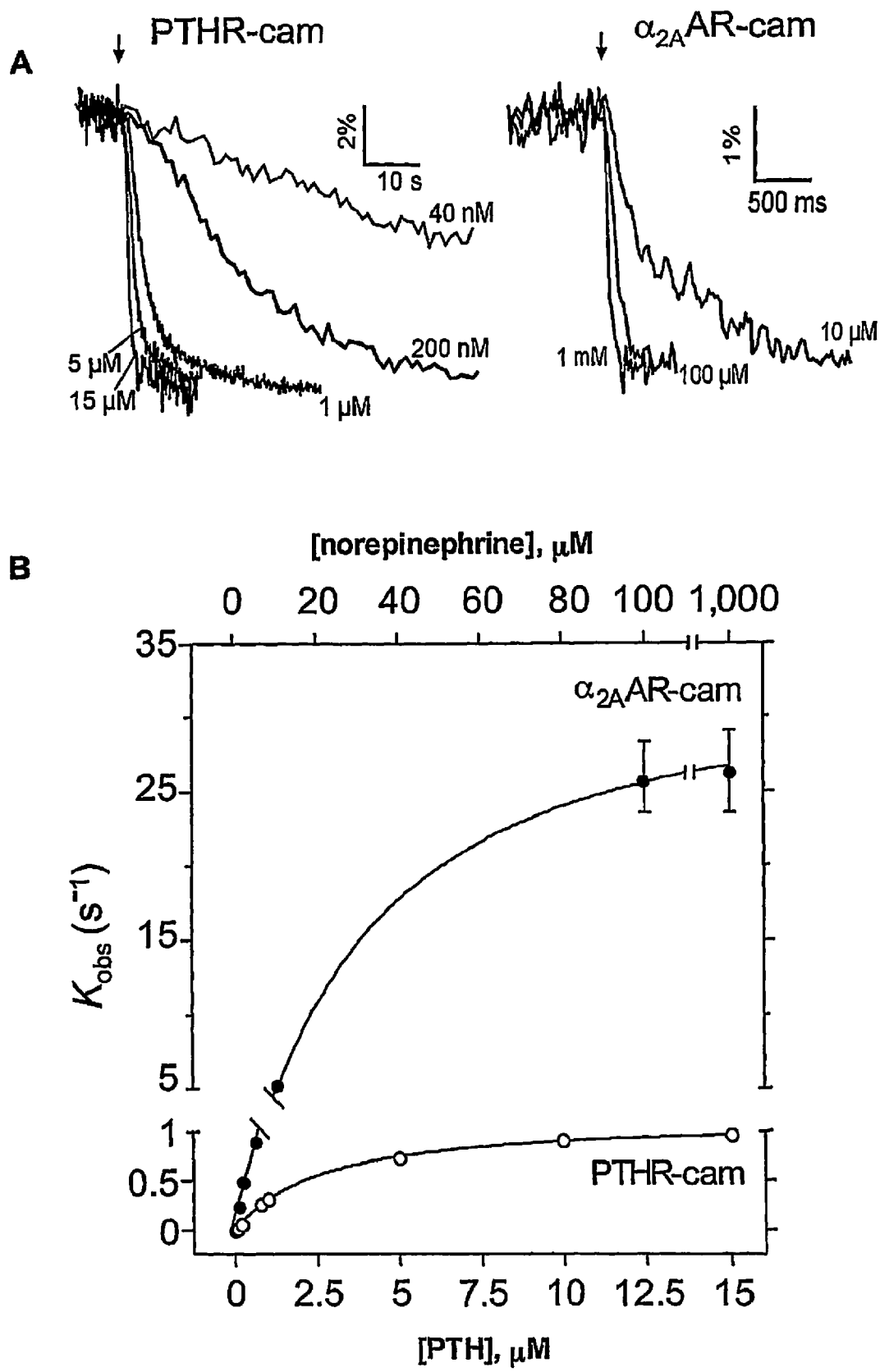

FIG. 6: Dynamics of agonist-mediated receptor conformational change. (A) Time-resolved changes in the ratio $F^*_{535}$/

F*$_{480}$ of the PTHR-cam (left panel) and α$_{2A}$AR-cam (right panel) expressed in HEK293 cells at various concentrations of PTH and norepinephrine, respectively. (B) Relationship between the apparent rate constant, k$_{obs}$ and agonist concentration. k$_{obs}$-values were also obtained from fitting the kinetic data of FIG. 6A with a mono-exponential equation. At low concentrations of agonist, k$_{obs}$-values were directly proportional to the agonist-concentration, whereas at higher concentrations of agonist the values approached a maximal value of about 1 s$^{-1}$ and 26 s$^{-1}$ for PTHR-cam and α$_{2A}$AR-cam, respectively. Note that the k$_{obs}$ values depicted in FIG. 6B saturated at much higher ligand concentrations than the binding data shown in FIG. 2. This is due to the fact that the k$_{obs}$ values are not measured at equilibrium. Data indicate the mean±SEM of at least 7 separate experiments.

Figure 7:
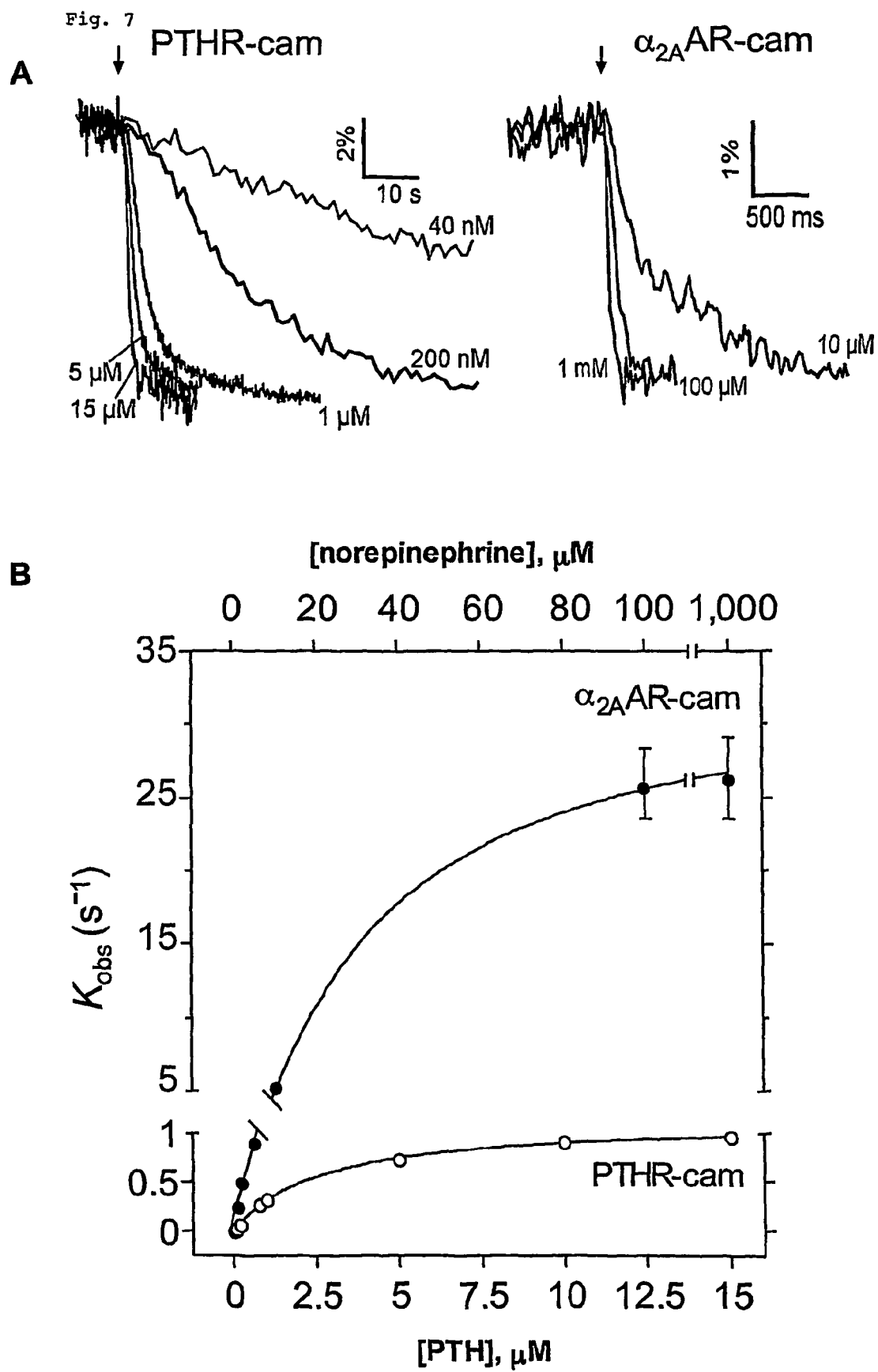

FIG. 7: Specific labelling of proteins containing the CCPGCC motif. Three individual constructs were transiently transfected into HeLa cells and incubated with FlAsH as described in the general methods. Only the constructs A2A-CFP-ModelPG-C49 (SEQ ID NOS: 43 and 44) and A2A-FlAsHPG-CFP-C49 (SEQ ID NOS: 39 and 40) contain the CCPGCC motif to specifically bind FlAsH while the construct A2A-CFP-C49 (SEQ ID NOS: 45 and 46) does not contain the binding motif for FlAsH. Fluorescence was measured by confocal microscopy. Cells were visualized twice under different excitation conditions. The top row shows the fluorescence of the cells when excited at 430 nm (excitation wavelength of CFP) and fluorescence was collected from 460-550 nm. The observed fluorescence reflects the fluorescence of CFP. The lower row shows the same cells when excited at 514 nm (excitation wavelength of FlAsH) and fluorescence was collected from 530-580 nm. For the constructs A2A-CFP-ModelPG-CFP-C49 (SEQ ID NOS: 43 and 44) and A2A-FlAsHPG-CFP-C49 (SEQ ID NOS: 39 and 40) a strong yellow fluorescence is observed that co-localises with the CFP-Fluorescence seen in the top row, while no such intense fluorescence is visible for the construct A2A-CFP-C49 (SEQ ID NOS: 45 and 46).

FIGS. 8A and B: Time resolved changes in the FRET ratio (535 nm/480 nm) in a single HeLa cell transiently transfected with A2A-CFP-C49 (SEQ ID NOS: 45 and 46). Emission intensities of FlAsH (535 nm, red), CFP (480 nm, blue), and the ratio (535 nm/480 nm, black) were recorded simultaneously from single cells. No change is observed upon rapid superfusion of 100 μM adenosine (black bar) since this construct does not specifically bind FlAsH. The timescales reflect the time points of the actual experiment.

Figure 9A:
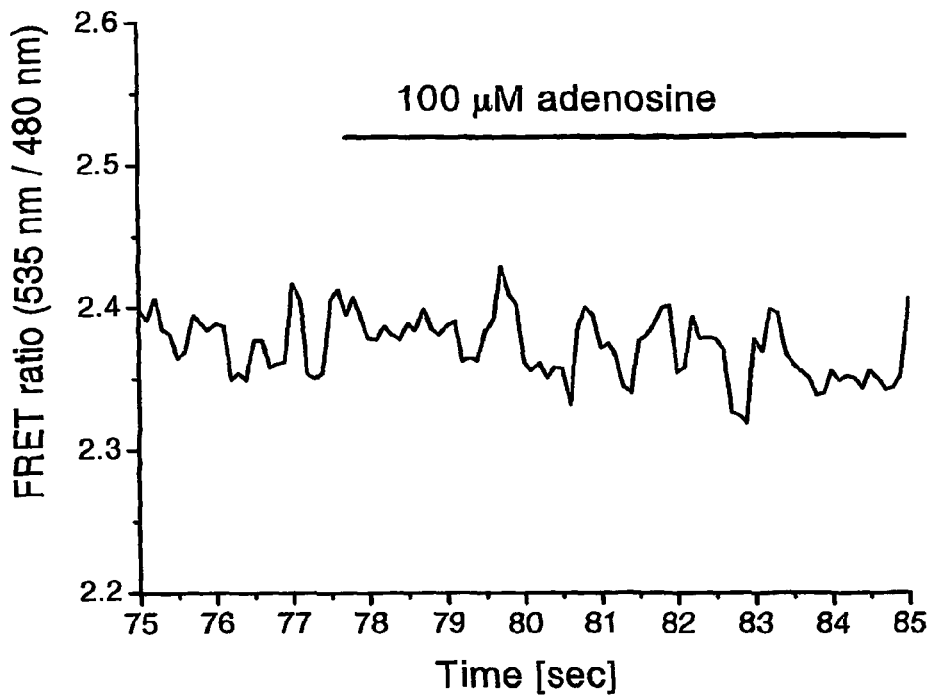

FIGS. 9A and B: Time resolved changes in the FRET ratio (535 nm/480 nm) in a single HeLa cell transiently transfected with A2A-CFP-ModelPG-C49 (SEQ ID NOS: 43 and 44). Emission intensities of FlAsH (535 nm, red), CFP (480 nm, blue), and the ratio (535 nm/480 nm, black) were recorded simultaneously from single cells. No change is observed upon rapid superfusion of 100 μM adenosine (black bar). As shown in FIG. 7 this construct does specifically bind FlAsH however, since both fluorophores are connected, it can not undergo an agonist dependent change in the FRET signal. The timescales reflect the time points of the actual experiment.

Figure 10A:
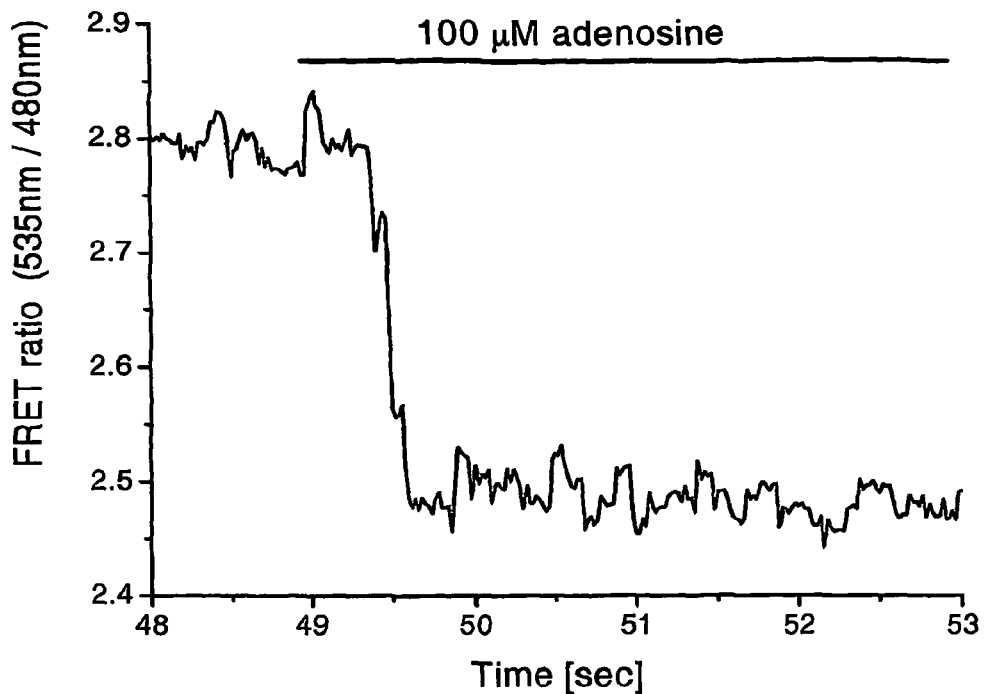

FIGS. 10A and B: Time resolved changes in the FRET ratio (535 nm/480 nm) in a single HeLa cell transiently transfected with A2A-FlAsHPG-CFP-C49 (SEQ ID NOS: 39 and 40). Emission intensities of FlAsH (535 nm, red), CFP (480 nm, blue), and the ratio (535 nm/480 nm, black) were recorded simultaneously from single cells. A strong and rapid signal change is observed upon rapid superfusion of 100 μM adenosine (black bar). As shown in FIG. 7 this construct does specifically bind FlAsH and as seen here can undergo an agonist dependent change in the FRET signal. The change of the signal is about 10% of the total signal. The decrease of the FRET ratio (535 nm/480 nm) was fitted by a simple mono-exponential curve giving a time constant in the experiment of 60 msec. The timescales reflect the time points of the actual experiment.

Figure 11:
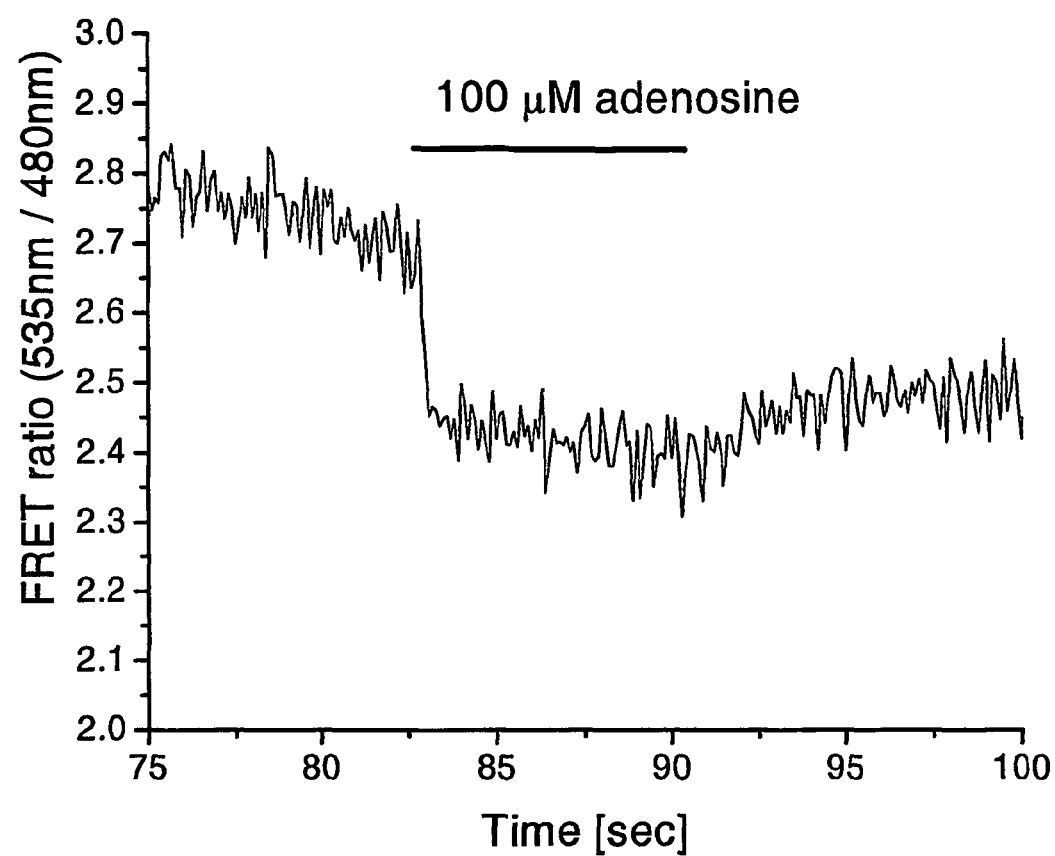

FIG. 11: Time resolved changes in the FRET ratio (535 nm/480 nm) in a single HeLa cell transiently transfected with A2A-FlAsHPG-CFP-C33 (SEQ ID NOS: 41 and 42). The fluorescence ration of FlAsH and CFP was recorded from single cells. A strong and rapid signal change is observed upon rapid superfusion of 100 μM adenosine (black bar). This construct is similar to the A2A-"chameleon" (SEQ ID NOS: 15 and 16) with respect to the relative positions of the fluorophores. As seen here the receptor can undergo an agonist dependent change in the FRET signal. The change of the signal is about 10% of the total signal. The timescales reflect the time points of the actual experiment.

Figure 12:
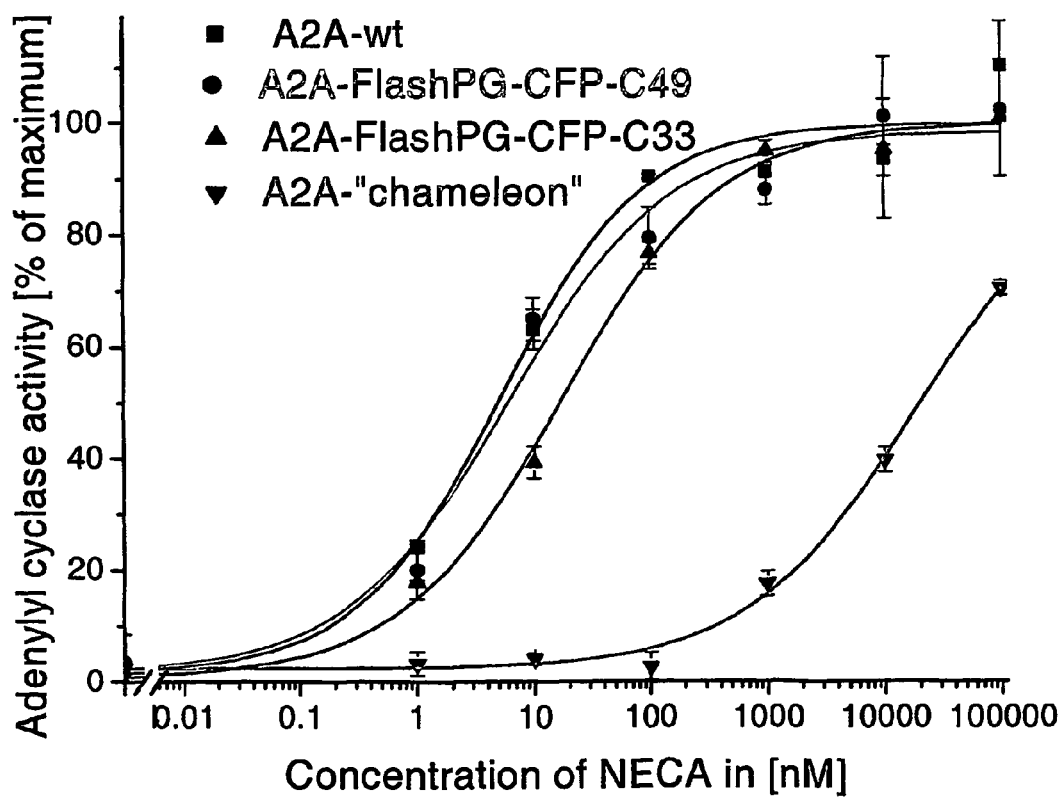

FIG. 12: Pharmacological properties of the Adenosine receptor constructs. A-B) Comparison between the binding (A) and signalling properties (B) of several adenosine receptor constructs with their respective wild-type receptor in transiently transfected COS cells. Adenylylcyclases activity was determined in membranes from transiently transfected COS cells as previously published (Jakobs et al., J cyclic Nucleotide Res 2 (1976) 381-392, Klotz et al., Naunyn-Schmiedeberg's Arch Pharmacol 357 (1998) 1-9). For binding of the radioligand $^3$H-NECA no significant difference was observed between wild-type A2A receptors at the different receptor constructs. The signalling properties of the FlAsH constructs (SEQ ID NOS: 39 and 40, as well as 41 and 42) were almost identical to the wild-type A2A receptor (SEQ ID NOS: 5 and 6), whereas with respect to functional response the A2A-"chameleon" receptor (SEQ ID NOS: 15 and 16) is shifted significantly to the right. Data are the mean±sd of at least 3 separate experiments.

Figure 13:
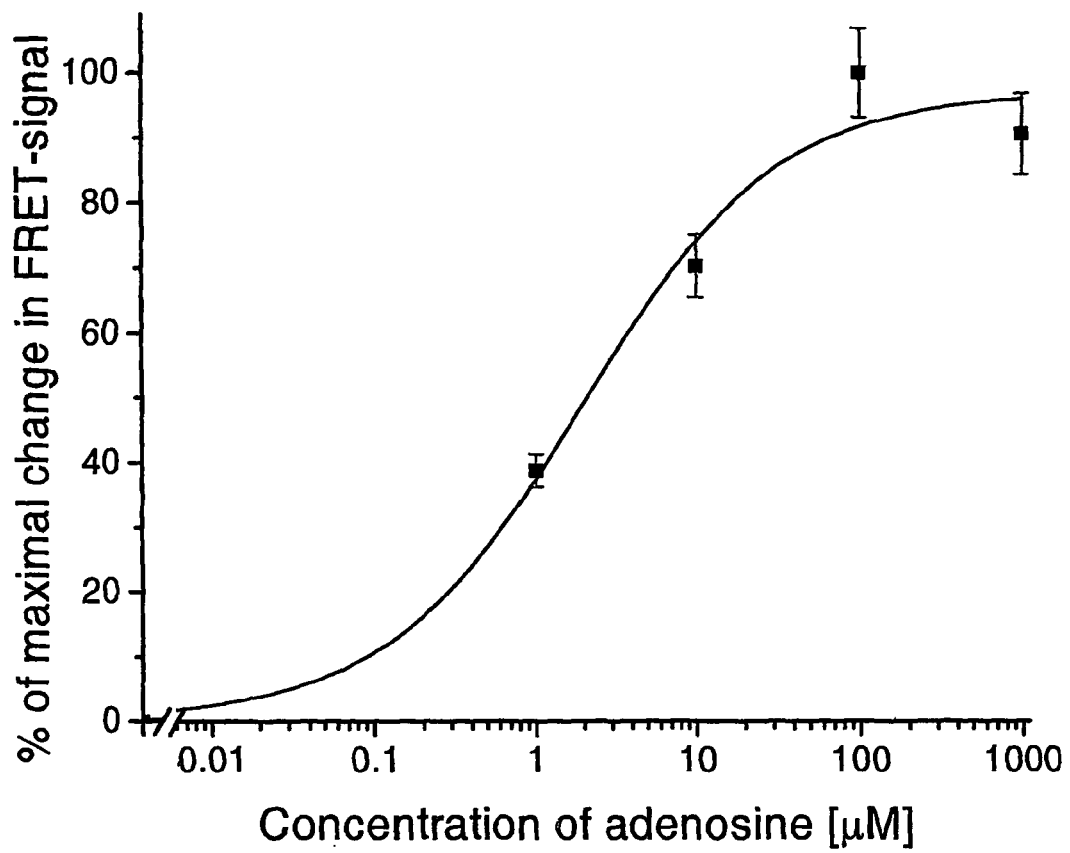

FIG. 13: The percent change of the FRET signal is concentration dependent of the agonist.

The changes of the FRET ratio (535 nm/480 nm) in a single HeLa cell transiently transfected with A2A-FlAsHPG-CFP-C49 (SEQ ID NOS: 39 and 40) were measured in dependence of the agonist concentration. Changes of the FRET signal during superfusion with agonist solutions were calculated as percent of the maximal change occurring upon stimulation with 100 μM adenosine. The results were plotted against agonist concentration. The figure clearly demonstrates a concentration dependent effect on the FRET signal FIG. 14: Different conformational changes in GPCR in response to agonist and inverse agonists. The α$_{2A}$AR-cam receptors were stably expressed in the neuronal cell line PC-12. A single cell was excited at 436 nm using a monochromator and fluorescence was detected simultaneously at 480 nm (CFP) and 535 nm (YFP). The signals were recorded before and after exposure to agonist (NA: noradrenaline, 100 μM) and two different inverse agonists (Yoh: yohimbine and Rau:rauwolscine, 100 μM).

The examples illustrate the invention.

EXAMPLE I

Experimental Protocol and Sequences Encoding Membrane Receptors of the Invention Molecular biology and cell culture. Site-directed mutagenesis was performed on the human PTH/PTHrP receptor (PTHR) and the mouse α$_{2A}$-adrenergic receptor cDNAs. The cDNAs encoding the enhanced yellow- and cyan fluorescent protein (YFP and CFP) were fused to position G418 of the COOH-terminus of the PTHR and inserted between Gly395 and Arg396 into the third intracellular loop of the PTHR, respectively. For the $\alpha_{2A}$-adrenergic receptor, YFP was inserted in the third intracellular loop between Ala250 and Ser371, and CFP was fused to Val461 in the C-terminus. Constructions were performed by polymerase chain reactions as described (Vilardaga, Biotechniques 18 (1995), 605-606). β-Arrestin2-YFP was constructed following the procedure described for the construction of arrestin3-GFP (Groarke, J. Biol. Chem. 274 (1999), 23263-23269). Constructions were verified by sequencing. Receptor cDNAs were cloned into pCDNA3 (Invitrogen) for transient and stable expression in mammalian cells. HEK293, CHO and PC12 cell lines served as the expression systems for the wild-type and chimeric receptors. The procedure for the selection of stable cell line has been previously described (Vilardaga, J. Biol. Chem. 276 (2001), 33435-33443).

Pharmacology. Ligand binding, receptor number determination, cAMP assays, measurement of $\alpha_{2A}$-adrenergic receptor-activated GIRK currents and reconstitution of receptor-$G_o$ coupling were measured as previously described (Vilardaga, (2001) loc. cit.; Bünemann, J. Bio. Chem. 276 (2001), 47512-47517; Vilardaga, J. Biol. Chem. 277 (2002), 8121-8129; Richardson, J. Biol. Chem. 274 (1999), 13525-13533). Saturation and competition binding studies were analysed with the program Prism to calculate $K_D$- and $K_i$-values.

Electrophysiology. Whole cell GIRK currents were measured in HEK293 cells stably expressing 6 pmol/mg membrane protein $\alpha_{2A}$R-cam 20-28 h after transient transfection with GIRK1 and GIRK4 as described previously (Bünemann, (2001), loc. cit.). Membrane currents were recorded using an EPC 9 amplifier and Pulse software (HEKA Instruments) for voltage control, data acquisition and data evaluation. Experimental conditions such as patch pipettes, internal and external solutions, voltage-clamp protocol as well as the superfusion system were the same as described previously (Bünemann, (2001), loc. cit.).

Fluorescence measurements. Cells were washed with PBS, scraped from the plate and resuspended in buffer A (137 mM NaCl, 5 mM KCl, 1 mM $CaCl_2$, 1 mM $MgCl_2$, 20 mM Hepes, 0.1% BSA, pH 7.4) at a density of $\approx 10^7$ cells/ml. Steady-state fluorescence emission spectra of the cells suspension were measured with a spectrofluorimeter (Perkin-Elmer) in cuvettes containing HEK293 cells expressing the indicated receptors, and were normalized to the respective maxima for PTHR-CFP$_{3\text{-}loop}$ and PTHR-cam. PTHR-YFP$_{C\text{-}term}$ was normalized relative to the maximal response upon exposure to 480 nm light.

FRET measurements. Cells grown on coverslips were maintained in buffer A at room temperature and placed on a Zeiss inverted microscope (Axiovert135) equipped with an oil immersion 63× objective and a dual emission photometric system (Till Photonics). Samples were excited with light from a polychrome IV (Till Photonics). In order to minimize photobleaching, the illumination time was set to 5 ms applied with a frequency between 1 and 75 Hz dependent on agonist concentration. FRET was monitored as the emission ratio of YFP to CFP, $F_{535}/F_{480}$, where $F_{535}$ and $F_{480}$ are the emission intensities at 535±15 nm and 480±20 nm (beam splitter DCLP 505 nm) upon excitation at 436±10 nm (beam splitter DCLP 460 nm). The emission ratio was corrected by the respective spill-over of CFP into the 535 nm channel (spill-over of YFP into the 480 nm channel was negligible) to give a corrected ratio $F^*_{535}/F^*_{480}$. FRET between CFP and YFP in cells stably expressing the receptor constructs was also determined by donor recovery after acceptor bleaching. The increase in emission at 480 nm was 50±2% after >80% bleaching of YFP (induced by 3-5 min continuous illumination with 480±15 nm). To determine agonist-induced changes in FRET, cells were continuously superfused with buffer A and agonist was applied using a computer assisted solenoid valve controlled rapid superfusion device ALA-VM8, ALA Scientific Instruments (solution exchange 5 to 10 ms). Signals detected by avalanche photodiodes were digitalized using a AD converter (Digidata1322A, Axon Instruments) and stored on PC using Clampex 8.1 software (Axon Instruments). The decrease in FRET ratio was fitted to the equation: $r(t)=A\times(1-e^{-t/\tau})$, where $\tau$ is the time constant (s) and A is the magnitude of the signal. When necessary for calculating $\tau$, agonist-independent changes in FRET due to photobleaching were subtracted.

Membrane preparation. Membrane fractions were obtained after two centrifugations at 4° C., first at 800×g for 10 min and the second at 100,000×g for 30 min. Membranes were treated with 6 M urea in 20 mM Hepes, pH 7.4, for 30 min on ice followed by centrifugation at 100,000×g for 15 min. After two washing steps at 4° C. in buffer B the membranes were resuspended in a buffer A (without BSA) and immediately used in the experiments. 20 µl aliquots of membranes were subjected to fluorescence microscopy similar to intact cells using a 20× objective.

The following sequences and constructs have been employed in course of the following experiments:

```
SEQ ID NO: 1: wildtype Mouse alpha2a adenergic
receptor cDNA sequence: Genbank M99377
(corresponding to human alpha 2A:Genbank:
NM_000681)
ATGGGCTACCCATACGACGTCCCAGACTACGCCAGCATGGGCTCACTGCA

GCCGGATGCCGGCAACAGCAGCTGGAACGGGACCGAAGCGCCCGGAGGCG

GCACCCGAGCCACCCCTTACTCCCTGCAGGTGACACTGACGCTGGTTTGC

CTGGCTGGCCTGCTCATGCTGTTCACAGTATTTGGCAACGTGCTGGTTAT

TATCGCGGTGTTCACCAGTCGCGCGCTCAAAGCTCCCCAAAACCTCTTCC

TGGTGTCCCTGGCCTCAGCGGACATCCTGGTGGCCACGCTGGTCATTCCC

TTTTCTTTGGCCAACGAGGTTATGGGTTACTGGTACTTTGGTAAGGTGTG

GTGTGAGATCTATTTGGCTCTCGACGTGCTCTTTTGCACGTCGTCCATAG

TGCACCTGTGCGCCATCAGCCTTGACCGCTACTGGTCCATCACGCAGGCC

ATCGAGTACAACCTGAAGCGCACGCCGCGTCGCATCAAGGCCATCATTGT

CACCGTGTGGGTCATCTCGGCTGTCATCTCCTTCCCGCCACTCATCTCCA

TAGAGAAGAAGACCAGAAGTGGTATGTGATCTCCTCGTCCATCGGTTCCT

TCTTCGCGCCTTGCCTCATCATGATCCTGGTCTACGTGCGTATTTACCAG

ATCGCGAAGCGTCGCACCCGCGTGCCTCCCAGCCGCCGGGGTCCGGACGC

CTGTTCCGCGCCGGCGGGGGCGCCGATCGCAGGCCCAACGGGCTGGGCC

CGGAGCGCGGCGCGGGTCCCACGGGCGCTGAGGCGGAGCCGCTGCCCACC

CAGCTTAACGGTGCCCCGGGGAGCCCGCGCCCGCCGGGCCCCGCGATGG

GGATGCGCTGGACCTAGAGGAGAGTTCGTCGTCCGAGCACGCCGAGCGGC

CCCCGGGGCCCGGCAGACCCGACCGCGGCCCCCGAGCCAAGGGCAAGACC

CGGGCGAGTCAGGTGAAGCCGGGGGACAGTCTGCCGCGCGCGGGCCCGG

GGCCGCGGGGCCGGGGGCTTCGGGGTCCGGGCACGGAGAGGAGCGCGGCG
```

-continued

```
GGGGCGCCAAAGCGTCGCGCTGGCGCGGGAGGCAAAACCGGGAGAAACGC

TTCACGTTCGTGCTGGCGGTGGTGATCGGCGTGTTCGTGGTGTGTTGGTT

TCCGTTCTTTTTCACCTACACGCTCATAGCGGTCGGCTGCCCGGTGCCCA

GCCAGCTCTTCAACTTCTTCTTCTGGTTGGGCTACTGCAACAGCTCGCTG

AACCCTGTTATCTACACCATCTTCAACCACGACTTCCGACGCGCCTTCAA

GAAGATCCTCTGCCGTGGGGACAGAAAACGCATCGTGTGA TTC AAC

CAC GAC TTC CGA CGC GCC TTC AAG AAG ATC CTC TGC

CGT GGG GAC AGA AAA CGC ATC GTG TGA

SEQ ID NO: 2: wildtype Mouse alpha2a adenergic
receptor amino acid sequence:
MGYPYDVPDYASMGSLQPDAGNSSWNGTEAPGGGTRATPYSLQVTLTLVC

LAGLLMLFTVFGNVLVIIAVFTSRALKAPQNLFLVSLASADILVATLVIP

FSLANEVMGYWYFGKVWCEIYLALDVLFCTSSIVHLCAISLDRYWSITQA

IEYNLKRTPRRIKAIIVTVWVISAVISFPPLISIEKKGAGGGQQPAEPSC

KINDQKWYVISSSIGSFFAPCLIMILVYVRIYQIAKRRTRVPPSRRGPDA

CSAPPGGADRRPNGLGPERGAGPTGAEAEPLPTQLNGAPGEPAPAGPRDG

DALDLEESSSSEHAERPPGPRRPDRGPRAKGKTRASQVKPGDSLPRRGPG

AAGPGASGSGHGEERGGGAKASRWRGRQNREKRFTFVLAVVIGVFVVCWF

PFFFTYTLIAVGCPVPSQLFNFFFWFGYCNSSLNPVIYTIFNHDFRRAFK

KILCRGDRKRIV

SEQ ID NO: 3: wildtype Human PTH/PTHrP receptor
cDNA sequence: Genbank: U22401 (corresponding
to mouse PTH/PTHrP receptor: NM_011199)
ATGGGGACCGCCCGGATCGCACCCGGCCTGGCGCTCCTGCTCTGCTGCCC
CGTGCTCAGCTCCGCGTACGCGCTGGTGGA TGCAGATGACGTCATGACTAAAGAGGAACAGATCTTCCTGCTGCAGCGTG
CTCAGGCCCAGTGCGAAAAACGGCTCAAGG AGGTCCTGCAGAGGCCAGCCAGCATAATGGAATCAGACAAGGGATGGACA
TCTGCGTCCACATCAGGGAAGCCCAGGAAA GATAAGGCATCTGGGAAGCTCTACCCTGAGTCTGAGGAGGACAAGGAGGC
ACCCACTGGCAGCAGGTACCGAGGGCGCCC GTGTCTGCCGGAATGGGACCACATCCTGTGCTGGCCGCTGGGGGCACCAG
GTGAGGTGGTGGCTGTGCCCTGTCCGGACT ACATTTATGACTTCAATCACAAAGGCCATGCCTACCGACGCTGTGACCGC
AATGGCAGCTGGGAGCTGGTGCCTGGGCAC AACAGGACGTGGGCCAACTACAGCGAGTGTGTCAAATTTCTCACCAATGA
GACTCGTGAACGGGAGGTGTTTGACCGCCT GGGCATGATTTACACCGTGGGCTACTCCGTGTCCCTGGCGTCCCTCACCG
TAGCTGTGCTCATCCTGGCCTACTTTAGGC GGCTGCACTGCACGCGCAACTACATCCACATGCACCTGTTCCTGTCCTTC
ATGCTGCGCGCCGTGAGGATCTTCGTCAAG GACGCTGTGCTCTACTCTGGCGCCACGCTTGATGAGGCTGAGCGCCTCAC
CGAGGAGGAGCTGCGCGCCATCGCCCAGGC GCCCCCGCCGCCTGCCACCGCCGCTGCCGGCTACGCGGGCTGCAGGGTGG
CTGTGACCTTCTTCCTTTACTTCCTGGCCA CCAACTACTACTGGATTCTGGTGGAGGGGCTGTACCTGCACAGCCTCATC
TTCATGGCCTTCTTCTCAGAGAAGAAGTAC CTGTGGGGCTTCACAGTCTTCGGCTGGGGTCTGCCCGCTGTCTTCGTGGC
TGTGTGGGTCAGTGTCAGAGCTACCCTGGC
```

```
CAACACCGGGTGCTGGGACTTGAGCTCCGGGAACAAAAAGTGGATCATCC
AGGTGCCCATCCTGGCCTCCATTGTGCTCA

ACTTCATCCTCTTCATCAATATCGTCCGGGTGCTCGCCACCAAGCTGCGG
GAGACCAACGCCGGCCGGTGTGACACACGG

CAGCAGTACCGGAAGCTGCTCAAATCCACGCTGGTGCTCATGCCCCTCTT
TGGCGTCCACTACATTGTCTTCATGGCCAC

ACCATACACCGAGGTCTCAGGGACGCTCTGGCAAGTCCAGATGCACTATG
AGATGCTCTTCAACTCCTTCCAGGGATTTT

TTGTCGCAATCATATACTGTTTCTGCAATGGCGAGGTACAAGCTGAGATC
AAGAAATCTTGGAGCCGCTGGACACTGGCA

CTGGACTTCAAGCGAAAGGCACGCAGCGGGAGCAGCAGCTATAGCTACGG
CCCCATGGTGTCCCACACAAGTGTGACCAA

TGTCGGCCCCGTGTGGGACTCGGCCTGCCCCTCAGCCCCCGCCTACTGC
CCACTGCCACCACCAACGGGCACCCTCAGC

TGCCTGGCCATGCCAAGCCAGGGACCCCAGCCCTGGAGACCCTCGAGACC
ACACCACCTGCCATGGCTGCTCCCAAGGAC

GATGGGTTCCTCAACGGCTCCTGCTCAGGCCTGGACGAGGAGGCCTCTGG
GCCTGAGCGGCCACCTGCCCTGCTACAGGA

AGAGTGGGAGACAGTCATGTGATGA

SEQ ID NO: 4: wildtype Human PTH/PTHrP receptor
amino acid sequence:
MGTARIAPGLALLLCCPVLSSAYALVDADDVMTKEEQIFLLHRAQAQCEK
RLKEVLQRPASIMESDKGWTSASTSGKPRK DKASGKLYPESEEDKEAPTGSRYRGRPCLPEWDHILCWPLGAPGEVVAVP
CPDYIYDFNHKGHAYRRCDRNGSWELVPGH NRTWANYSECVKFLTNETREREVFDRLGMIYTVGYSVSLASLTVAVLILA
YFRRLHCTRNYIHMHLFLSFMLRAVSIFVK

DAVLYSGATLDEAERLTEEELRAIAQAPPPPATAAAGYAGCRVAVTFFLY
FLATNYYWILVEGLYLHSLIFMAFSEKKY

LWGFTVFGWGLPAVFVAVWVSVRATLANTGCWDLSSGNKKWIIQVPILAS
IVLNFILFINIVRVLATKLRETNAGRCDTR

QQYRKLLKSTLVLMPLFGVHYIVFMATPYTEVSGTLWQVQMHYEMLFNSF
QGFFVAIIYCFCNGEVQAEIKKSWSRWTLA

LDFKRKARSGSSSYSYGPMVSHTSVTNVGPRVGLGLPLSPRLLPTATTNG
HPQLPGHAKPGTPALETLETTPPAMAAPKD

DGFLNGSCSGLDEEASGPERPPALLQEEWETVM

SEQ ID NO: 5: witdtype A2A adenosine receptor
(human) cDNA: Genbank: M97370 (corresponding to
mouse: XM_125720)
ATGCCCATCATGGGCTCCTCGGTGTACATCACGGTGGAGCTGGCCATTGC

TGTGCTGGCCATCCTGGGCAATGTGCTGGTGTGCTGGGCCGTGTGGCTCA

ACAGCAACCTGCAGAACGTCACCAACTACTTTGTGGTGTCACTGGCGGCG

GCCGACATCGCAGTGGGTGTGCTCGCCATCCCGTTTGCCATCACCATCAG

CACCGGGTTCTGCGCTGCCTGCCACGGCTGCCTCTTCATTGCCTGCTTCG

TGCTGGTCCTCACGCAGAGCTCCATCTTCAGTCTCCTGGCCATCGCCATT

GACCGCTACATTGCCATGCGCATCCCGCTCCGGTACAATGGCTTGGTGAC

CGGCACGAGGGCTAAGGGCATCATTGCCATCTGCTGGGTGCTGTCGTTTG

CCATCGGCCTGACTCCCATGCTAGGTTGGAACAACTGCGGTCAGCCAAAG

GAGGGCAAGAACCACTCCCAGGGCTGCGGGGAGGGCCAAGTGGCCTGTCT

CTTTGAGGATGTGGTCCCCATGAAGTACATGGTGTACTTCAACTTCTTTC

CTGTGTGCTGGTGCCCCTGCTGCTCATGCTGGGTGTCTATTTGCGGATCT
```

TCCTGGCGGCGCGACGACAGCTGAAGCAGATGGAGAGCCAGGCTCTGCCG

GGGGAGCGGGCACGGTCCACACTGCAGAAGGAGGTCCATGCTGCCAAGTC

ACTGGCCATCATTGTGGGGCTCTTTGCCCTCTGCTGGCTGCCCCTACACA

TCATCAACTGCTTCACTTTGTTCTGCCCCGAGTGCAGCCACGCCCCTCTC

TGGCTCATGTACCTGGCCATCGTCCTCTCCCACACCAATTCGGTTGTGAA

TCCCCTTCATCTACGCCTACCGTATCCGCGAGTTCCGCCAGACCTTCCGCA

AGATCATTCGCAGCCACGTCCTGAGGCAGCAAGAACCTTTCAAGGCAGCT

GGCACCAGTGCCCGGGTCTTGGCAGCTCATGGCAGTGACGGAGAGCAGGT

CAGCCTCCGTCTCAACGGCCACCCGCCAGGAGTGTGGGCCAACGGCAGTG

CTCCCCACCCTGAGCGGAGGCCCAATGGCTATGCCCTGGGGCTGGTGAGT

GGAGGGAGTGCCCAAGAGTCCCAGGGGAACACGGGCCTCCCAGACGTGGA

GCTCCTTAGCCATGAGCTCAAGGGAGTGTGCCCAGAGCCCCCTGGCCTAG

ATGACCCCCTGGCCCAGGATGGAGCAGGAGTGTCCTGA

SEQ ID NO: 6: wildtype A2A adenosine receptor
(human) amino acid sequence
MPIMGSSVYITVELAIAVLA1LGNVLVCWAVWLNSNLQNVTNYFVSLAAA

DIAVGVLAIPFAITISTGFCAACHGCLFIACFVLVLTQSSIFSLLAIAID

RYIAIRIPLRYNGLVTGTRAKGIIAICWVLSFAIGLTPMLGWNNCGQPKE

GKNHSQGCGEGQVACLFEDVVPMNYMVYFNFFACVLVPLLLMLGVYLR1F

LAARRQLKQMESQPLPGERARSTLQKEVHAAKSLAIIVGLFALCWLPLHI

INCFTFFCPDCSHAPLWLMYLAIVLSHTNSVVNPFIYAYRIREFRQTFRK

IIRSHVLRQQEPFKAAGTSARVLAAHGSDGEQVSLRLNGHPPGVWANGSA

PHPERRPNGYALGLVSGGSAQESQGNTGLPDVELLSHELKG

The following fluorophore sequences have been employed in the appended examples:

SEQ ID NO: 7: eCFP (enhanced CFP) cDNA sequence
(Clonetech)
ATGGTGAGCAAGGGCGAGGAGCTGTTCACCGGGGTGGTGCCCATCCTGGT
CGAGCTGGACGGCGACGTAAACGGCCACAA GTTCAGCGTGTCCGGCGAGGGCGAGGGCGATGCCACCTACGGCAAGCTGA
CCCTGAAGTTCATCTGCACCACCGGCAAGC TGCCCGTGCCCTGGCCCACCCTCGTGACCACCCTGACCTGGGGCGTGCAG
TGCTTCAGCCGCTACCCCGACCACATGAAG CAGCACGACTTCTTCAAGTCCGCCATGCCCGAAGGCTACGTCCAGGAGCG
CACCATCTTCTTCAAGGACGACGGCAACTA CAAGACCCGCGCCGAGGTGAAGTTCGAGGGCGAGACCCTGGTGAACCGCA
TCGAGCTGAAGGGCATCGACTTCAAGGAGG ACGGCAACATCCTGGGGCACAAGCTGGAGTACAACTACATCAGCCACAAC
GTCTATATCACCGCCGACAAGCAGAAGAAC GGCATCAAGGCCAACTTCAAGATCCGCCACAACATCGAGGACGGCAGCGT
GCAGCTCGCCGACCACTACCAGCAGAACAC CCCCATCGGCGACGGCCCCGTGCTGCTGCCCGACAACCACTACCTGAGCA
CCCAGTCCGCCCTGAGCAAAGACCCCAACG AGAAGCGCGATCACATGGTCCTGCTGGAGTTCGTGACCGCCGCCGGGATC
ACTCTCGGCATGGACGAGCTGTACAAGTAA SEQ ID NO: 8: eCFP (enhanced CFP) amino acid
sequence:
MVSKGEELFTGVVPILVELDGDVNGHKFSVSGEGEGDATYGKLTLKFICT
TGKLPVPWPTLVTTLTWGVQCFSRYPDHMK QHDFFKSAMPEGYVQERTIFFKDDGNYKTRAEVKFEGDTLVNRIELKGID
FKEDGNILGHKLEYNYISHNVYITADKQKN

GIKANFKIRHNIEDGSVQLADHYQQNTPIGDGPVLLPDNHYLSTQSALSK
DPNEKRDHMVLLEFVTAAGITLGMDELYK

SEQ ID NO: 9: YFP cDNA sequence: (Clonetech)
ATGGTGAGCAAGGGCGAGGAGCTGTTCACCGGGGTGGTGCCCATCCTGGT
CGAGCTGGACGGCGACGTAAACGGCCACAA GTTCAGCGTGTCCGGCGAGGGCGAGGGCGATGCCACCTACGGCAAGCTGA
CCCTGAAGTTCATCTGCACCACCGGCAAGC TGCCCGTGCCCTGGCCCACCCTCGTGACCACCTTCGGCTACGGCCTGCAG
TGCTTCGCCCGCTACCCCGACCACATGAAG CAGCACGACTTCTTCAAGTCCGCCATGCCCGAAGGCTACGTCCAGGAGCG
CACCATCTTCTTCAAGGACGACGGCAACTA CAAGACCCGCGCCGAGGTGAAGTTCGAGGGCGACACCCTGGTGAACCGCA
TCGAGCTGAAGGGCATCGACTTCAAGGAGG ACGGCAACATCCTGGGGCACAAGCTGGAGTACAACTACAACAGCCACAAC
GTCTATATCATGGCCGACAAGCAGAAGAAC GGCATCAAGGTGAACTTCAAGATCCGCCACAACATCGAGGACGGCAGCGT
GCAGCTCGCCGACCACTACCAGCAGAACAC CCCCATCGGCGACGGCCCCGTGCTGCTGCCCGACAACCACTACCTGAGCT
ACCAGTCCGCCCTGAGCAAAGACCCCAACG AGAAGCGCGATCACATGGTCCTGCTGGAGTTCGTGACCGCCGCCGGGATC
ACTCTCGGCATGGACGAGCTGTACAAGTAA SEQ ID NO: 10: YFP amino acid sequence:
MVSKGEELFTGVVPILVELDGDVNGHKFSVSGEGEGDATYGKLTLKFICT
TGKLPVPWPTLVTTFGYGLQCFARYPDHMK QHDFFKSAMPEGYVQERTIFFKDDGNYKTRAEVKFEGDTLVNRIELKGID
FKEDGNILGHKLEYNYNSHNVYIMADKQKN

GIKVNFKIRHNIEDGSVQLADHYQQNTPIGDGPVLLPDNHYLSYQSALSK
DPNEKRDHMVLLEFVTAAGITLGMDELYK

In the following receptor-cam ("chameleon") sequences the CFP and YFP Sequences are identified by bold printing:

SEQ ID NO: 11: alpha2a adrenergic receptor-cam
cDNA sequence:
ATGGGCTACCCATACGACGTCCCAGACTACGCCAGCATGGGCTCACTGCA
GCCGGATGCCGGCAACAGCAGCTGGAACGG GACCGAAGCGCCCGGAGGCGGCACCCGAGCCACCCCTTAGTCCCTGCAGG
TGACACTGACGCTGGTTTGCCTGGCTGGCC TGCTCATGCTGTTCACAGTATTTGGCAACGTGCTGGTTATTATCGCGGTG
TTCACCAGTCGCGCGCTCAAAGCTCCCCAA AACCTCTTCCTGGTGTCCCTGGCCTCAGCGGACATCCTGGTGGCCACGCT
GGTCATTCCCTTTTCTTTGGCCAACGAGGT TATGGGTTACTGGTACTTTGGTAAGGTGTGGTGTGAGATCTATTTGGCTC
TCGACGTGCTCTTTTGCACGTCGTCCATAG TGCACCTGTGCGCCATCAGCCTTGACCGCTACTGGTCCATCACGCAGGCC
ATCGAGTACAACCTGAAGCGCACGCCGCGT CGCATCAAGGCCATCATTGTCACCGTGTGGGTCATCTCGGCTGTCATCTC
CTTCCCGCCACTCATCTCCATAGAGAAGAA GGGCGCTGGCGGCGGGCAGCAGCCGGCCGAGCCAAGCTGCAAGATCAACG
ACCAGAAGTGGTATGTCATCTCCTCGTCCA -continued TCGGTTCCTTCTTCGCGCCTTGCCTCATCATGATCCTGGTCTACGTGCGT
ATTTACCAGATCGCCAAGCGTCGCACCCGC

**GTGCCTCCCAGCCGCCGGGGTCCGGACGCCATGGTGAGCAAGGGCGAGGA
GCTGTTCACCGGGGTGGTGCCCATCCTGGT**

**CGAGCTGGACGGCGACGTAAACGGCCACAAGTTCAGCGTGTCCGGCGAGG
GCGAGGGCGATGCCACCTACGGCAAGCTGA**

**CCCTGAAGTTCATCTGCACCACCGGCAAGCTGCCCGTGCCCTGGCCCACC
CTCGTGACCACCTTCGGCTACGGCCTGCAG**

**TGCTTCGCCCGCTACCCCGACCACATGAAGCAGCACGACTTCTTCAAGTC
CGCCATGCCCGAAGGCTACGTCCAGGAGCG**

**CACCATCTTCTTCAAGGACGACGGCAACTACAAGACCCGCGCCGAGGTGA
AGTTCGAGGGCGACACCCTGGTGAACCGCA**

**TCGAGCTGAAGGGCATCGACTTCAAGGAGGACGGCAACATCCTGGGGCAC
AAGCTGGAGTACAACTACAACAGCCACAAC**

**GTCTATATCATGGCCGACAAGCAGAAGAACGGCATCAAGGTGAACTTCAA
GATCCGCCACAACATCGAGGACGGCAGCGT**

**GCAGCTCGCCGACCACTACCAGCAGAACACCCCCATCGGCGACGGCCCCG
TGCTGCTGCCCGACAACCACTACCTGAGCT**

**ACCAGTCCGCCCTGAGCAAAGACCCCAACGAGAAGCGCGATCACATGGTC
CTGCTGGAGTTCGTGACCGCCGCCGGGATC**

ACTCTCGGCATGGACGAGCTGTACAAGCGCTGGCGCGGGAGGCAAAACCG
GGAGAAACGCTTCACGTTCGTGCTGGCGGT

GGTGATCGGCGTGTTCGTGGTGTGTTGGTTTCCGTTCTTTTTTCACCTACA
CGCTCATAGCGGTCGGCTGCCCGGTGCCCA

GCCAGCTCTTCAACTTCTTCTTCTGGTTCGGCTACTGCAACAGCTCGCTG
AACCCTGTTATCTACACCATCTTCAACCAC

GACTTCCGACGCGCCTTCAAGAAGATCCTCTGCCGTGGGGACAGAAAACG
CATCGTGATGGTGAGCAAGGGCGAGGAGCT

**GTTCACCGGGGTGGTGCCCATCCTGGTCGAGCTGGACGGCGACGTAAACG
GCCACAAGTTCAGCGTGTCCGGCGAGGGCG**

**AGGGCGATGCCACCTACGGCAAGCTGACCCTGAAGTTCATCTGCACCACC
GGCAAGCTGCCCGTGCCCTGGCCCACCCTC**

**GTGACCACCCTGACCTGGGGCGTGCAGTGCTTCAGCCGCTACCCCGACCA
CATGAAGCAGCACGACTTCTTCAAGTCCGC**

**CATGCCCGAAGGCTACGTCCAGGAGCGCACCATCTTCTTCAAGGACGACG
GCAACTACAAGACCCGCGCCGAGGTGAAGT**

**TCGAGGGCGACACCCTGGTGAACCGCATCGAGCTGAAGGGCATCGACTTC
AAGGAGGACGGCAACATCCTGGGGCACAAG**

**CTGGAGTACAACTACATCAGCCACAACGTCTATATCACCGCCGACAAGCA
GAAGAACGGCATCAAGGCCAACTTCAAGAT**

**CCGCCACAACATCGAGGACGGCAGCGTGCAGCTCGCCGACCACTACCAGC
AGAACACCCCCATCGGCGACGGCCCCGTGC**

**TGCTGCCCGACAACCACTACCTGAGCACCCAGTCCGCCCTGAGCAAAGAC
CCCAACGAGAAGCGCGATCACATGGTCCTG**

**CTGGAGTTCGTGACCGCCGCCGGGATCACTCTCGGCATGGACGAGCTGTA
CAAGTAA**

SEQ ID NO: 12: Alpha2a adrenergic receptor-cam
"chameleon" amino acid sequence:
MGYPYDVPDYASMGSLQPDAGNSSWNGTEAPGGGTRATPYSLQVTLTLVC
LAGLLMLFTVFGNVLVIIAVFTSRALKAPQ NLFLVSLASADILVATLVIPFSLANEVMGYWYFGKVWCEIYLALDVLFCT
SSIVHLCAISLDRYWSITQAIEYNLKRTPR RIKAIIVTVWVISAVISFPPLISIEKKGAGGGQQPAEPSCKINDQKWYVI
SSSIGSFFAPCLIMILVYVRIYQIAKRRTR VPPSRRGPDA**MVSKGEELFTGVVPILVELDGDVNGHKFSVSGEGEGDATYG
KLTLKFICTTGKLPVPWPTLVTTFGYGLQ**

**CFARYPDHMKQHDFFKSAMPEGYVQERTIFFKDDGNYKTRAEVKFEGDTL
VNRIELKGIDFKEDGNILGHKLEYNYNSHN**

**VYIMADKQKNGIKVNFKIRHNIEDGSVQLADHYQQNTPIGDGPVLLPDNH
YLSYQSALSKDPNEKRDHMVLLEFVTAAGI**

TLGMDELYKRWRGRQNREKRFTFVLAVVIGVFVVCWFPFFFTYTLIAVGC
PVPSQLFNFFFWFGYCNSSLNPVIYTIFNH

DFRRAFKKILCRGDRKRIV**MVSKGEELFTGVVPILVELDGDVNGHKFSVS
GEGEGDATYGKLTLKFICTTGKLPVPWPTL**

**VTTLTWGVQCFSRYPDHMKQHDFFKSAMPEGYVQERTIFFKDDGNYKTRA
EVKFEGDTLVNRIELKGIDFKEDGNILGHK**

**LEYNYISHNVYITADKQKNGIKANFKIRHNIEDGSVQLADHYQQNTPIGD
GPVLLPDNHYLSTQSALSKDPNEKRDHMVL**

LEFVTAAGITLGMDELYK

SEQ ID NO: 13: PTH receptor-cam "chameleon" 8 cDNA
sequence:
ATGGGGACCGCCCGGATCGCACCCGGCCTGGCGCTCCTGCTCTGCTGCCC
CGTGCTCAGCTCCGCGTACGCGCTGGTGGA TGCAGATGACGTCATGACTAAAGAGGAACAGATCTTCCTGCTGCACCGTG
CTCAGGCCCAGTGCGAAAAACGGCTCAAGG AGGTCCTGCAGAGGCCAGCCAGCATAATGGAATCAGACAAGGGATGGACA
TCTGCGTCCACATCAGGGAAGCCCAGGAAA GATAAGGCATCTGGGAAGCTCTACCCTGAGTGTGAGGAGGACAAGGAGGC
ACCCACTGGCAGCAGGTACCGAGGGCGCCC CTGTCTGCCGGAATGGGACCACATCGTGTGCTGGCCGCTGGGGGCACCAG
GTGAGGTGGTGGCTGTGCCCTGTCCGGACT ACATTTATGACTTCAATCACAAAGGCCATGCCTACCGACGCTGTGACCGG
AATGGCAGCTGGGAGCTGGTGCCTGGGCAC AACAGGACGTGGGCCAACTACAGCGAGTGTGTCAAATTTCTCACCAATGA
GACTCGTGAACGGGAGGTGTTTGACCGCCT GGGCATGATTTACACCGTGGGCTACTCCGTGTCCCTGGCGTCCCTCACCG
TAGCTGTGCTCATCCTGGCCTACTTTAGGC GGCTGCACTGCACGCGCAACTACATCCACATGCACCTGTTCCTGTCCTTC
ATGCTGCGCGCCGTGAGCATCTTCGTCAAG GACGCTGTGCTCTACTCTGGCGCCACGCTTGATGAGGCTGAGCGCCTCAC
CGAGGAGGAGCTGCGCGCCATCGCCCAGGC GCCCCCGCCGCCTGCCACCGCCGCTGCCGGCTACGCGGGCTGCAGGGTGG
CTGTGACCTTCTTCCTTTACTTCCTGGCCA

CCAACTACTACTGGATTCTGGTGGAGGGGCTGTACCTGCACAGCCTCATC
TTCATGGCCTTCTTCTCAGAGAAGAGTAC

CTGTGGGGCTTCACAGTCTTCGGCTGGGGTCTGCCCGCTGTCTTCGTGGC
TGTGTGGGTCAGTGTCAGAGCTACCCTGGC

CAACACCGGGTGCTGGGACTTGAGCTCCGGGAACAAAAGTGGATCATCC
AGGTGCCCATCCTGGCCTCCATTGTGCTCA

ACTTCATCCTCTTCATCAATATCGTCCGGGTGCTCGCCACCAAGCTGCGG
GAGACCAACGCCGGATGGTGAGCAAGGGC

**GAGGAGCTGTTCACCGGGGTGGTGCCCATCCTGGTCGAGCTGGACGGCGA
CGTAAACGGCCACAAGTTCAGCGTGTCCGG**

**CGAGGGCGAGGGCGATGCCACCTACGGCAAGCTGACCCTGAAGTTCATCT
GCACCACCGGCAAGCTGCCCGTGCCCTGGC**

**CCACCCTCGTGACCACCCTGACCTGGGGCGTGCAGTGCTTCAGCCGCTAC
CCCGACCACATGAAGCAGCACGACTTCTTC**

AAGTCCGCCATGCCCGAAGGCTACGTCCAGGAGCGCACCATCTTCTTCAA

-continued
```
GGACGACGGCAACTACAAGACCCGCGCCGA

GGTGAAGTTCGAGGGCGACACCCTGGTGAACCGCATCGAGCTGAAGGGCA
TCGACTTCAAGGAGGACGGCAACATCCTGG

GGCACAAGCTGGAGTACAACTACATCAGCCACAACGTCTATATCACCGCC
GACAAGCAGAAGAACGGCATCAAGGCCAAC

TTCAAGATCCGCCACAACATCGAGGACGGCAGCGTGCAGCTCGCCGACCA
CTACCAGCAGAACACCCCCATCGGCGACGG

CCCCGTGCTGCTGCCCGACAACCACTACCTGAGCACCCAGTCCGCCCTGA
GCAAAGACCCCAACGAGAAGCGCGATCACA

TGGTCCTGCTGGAGTTCGTGACCGCCGCCGGGATCACTCTCGGCATGGAC
GAGCTGTACAAGCGGTGTGACACACGGCAG

CAGTACCGGAAGCTGCTCAAATCCACGCTGGTGCTCATGCCCCTCTTTGG
CGTCCACTACATTGTCTTCATGGCCACACC

ATACACCGAGGTCTCAGGGACGCTCTGGCAAGTCCAGATGCACTATGAGA
TGCTCTTCAACTCCTTCCAGGGATTTTTTG

TCGCAATCATATACTGTTTCTGCAATGGCGAGGTACAAGCTGAGATCAAG
AAATCTTGGAGCCGCTGGACACTGGCACTG

GACTTCAAGCGAAAGGCACGCAGCGGGAGCAGCAGCTATAGCTACGGCAT
GGTGAGCAAGGGCGAGGAGCTGTTCACCGG

GGTGGTGCCCATCCTGGTCGAGCTGGACGGCGACGTAAACGGCCACAAGT
TCAGCGTGTCCGGCGAGGGCGAGGGCGATG

CCACCTACGGCAAGCTGACCCTGAAGTTCATCTGCACCACCGGCAAGCTG
CCCGTGCCCTGGCCCACCCTCGTGACCACC

TTCGGCTACGGCCTGCAGTGCTTCGCCCGCTACCCCGACCACATGAAGCA
GCACGACTTCTTCAAGTCCGCCATGCCCGA

AGGCTACGTCCAGGAGCGCACCATCTTCTTCAAGGACGACGGCAACTACA
AGACCCGCGCCGAGGTGAAGTTCGAGGGCG

ACACCCTGGTGAACCGCATCGAGCTGAAGGGCATCGACTTCAAGGAGGAC
GGCAACATCCTGGGGCACAAGCTGGAGTAC

AACTACAACAGCCACAACGTCTATATCATGGCCGACAAGCAGAAGAACGG
CATCAAGGTGAACTTCAAGATCCGCCACAA

CATCGAGGACGGCAGCGTGCAGCTCGCCGACCACTACCAGCAGAACACCC
CCATCGGCGACGGCCCCGTGCTGCTGCCCG

ACAACCACTACCTGAGCTACCAGTCCGCCCTGAGCAAAGACCCCAACGAG
AAGCGCGATCACATGGTCCTGCTGGAGTTC

GTGACCGCCGCCGGGATCACTCTCGGCATGGACGAGCTGTACAAGTAA
```

SEQ ID NO: 14: PTH receptor-cam8 "chameleon" amino
acid sequence:
MGTARIAPGLALLLCCPVLSSAYALVDADDVMTKEEQIFLLHRAQAQCEK
RLKEVLQRPASIMESDKGWTSASTSGKPRK DKASGKLYPESEEDKEAPTGSRYRGRPCLPEWDHILCWPLGAPGEVVAVP
CPDYIYDFNHKGHAYRRCDRNGSWELVPGH NRTWANYSECVKFLTNETREREVFDRLGMIYTVGYSVSLASLTVAVLILA
YFRRLHCTRNYIHMHLFLSFMLRAVSIFVK DAVLYSGATLDEAERLTEEELRAIAQAPPPPATAAAGYAGCRVAVTFFLY
FLATNYYWILVEGLYLHSLIFMAFFSEKKY LWGFTVFGWGLPAVFVAVWVSVRATLANTGCWDLSSGNKKWIIQVPILAS
IVLNFILFINIVRVLATKLRETNAGMVSKG

**EELFTGVVPILVELDGDVNGHKFSVSGEGEGDATYGKLTLKFICTTGKLP
VPWPTLVTTLTWGVQCFSRYPDHMKQHDFF**

**KSAMPEGYVQERTIFFKDDGNYKTRAEVKFEGDTLVNRIELKGIDFKEDG
NILGHKLEYNYISHNVYITADKQKNGIKAN**

**FKIRHNIEDGSVQLADHYQQNTPIGDGPVLLPDNHYLSTQSALSKDPNEK
RDHMVLLEFVTAAGITLGMDELYK**RCDTRQ

QYRKLLKSTLVLMPLFGVHYIVFMATPYTEVSGTLWQVQMHYEMLFNSFQ
GFFVAIIYCFCNGEVQAEIKKSWSRWTLAL

DFKRKARSGSSSYSYG**MVSKGEELFTGVVPILVELDGDVNGHKFSVSGEG
EGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

**NYNSHNVYIMADKQKNGIKVNFKIRHNIEDGSVQLADHYQQNTPIGDGPV
LLPDNHYLSYQSALSKDPNEKRDHMVLLEF**

VTAAGITLGMDELYK

SEQ ID NO: 15: A2A-CFP14/10-YFP-C33 cDNA sequence;
A2A "chameleon"
```
ATGCCCATCATGGGCTCCTCGGTGTACATCACGGTGGAGCTGGCCATTGC

TGTGCTGGCCATCCTGGGCAATGTGCTGGTGTGCTGGGCCGTGTGGCTCA

ACAGCAACCTGCAGAACGTCACCAACTACTTTGTGGTGTCACTGGCGGCG

GCCGACATCGCAGTGGGTGTGCTCGCCATGCCCTTTGCCATCACCATCAG

CACCGGGTTCTGCGCTGCCTGCCACGGCTGCCTCTTCATTGCCTGCTTCG

TCCTGGTCC TCACGCAGAG CTCCATCTTC AGTCTCCTGG CCATCGC

CAT TGACCGCTAC ATTGCCATCC GCATCCCGCT CCGGTACAAT GGC

TTGGTGA CCGGCACGAG GGCTAAGGGC ATCATTGCCA TCTGCTGGGT

GCTGTCGTTT GCCATCGGCC TGACTCCCAT GCTAGGTTGG AACAACTGC

GGTCAGCCAA AGGAGGGCAA GAACCAGTCC CAGGGCTGCG GGGAGGGCCA

AGTGGCCTGT CTCTTTGAGG ATGTGGTCCC ATGAACTACA TGGTGTA

CTTCAACTTC TTTGCCTGTG TGCTGGTGCC CCT GCTGCTCATG CTGGG

TGTCT ATTTGCGGAT CTTCCTGGCG GCGCGACGACAGCTGAAGCAGATG

GA**GGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTG

GGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACATCAGCCACAAC

GTCTATATCACCGCCGACAAGCAGAAGAACGGCATCAAGGCCAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAG** CTTCAGA AGGAGGTCCA TGCTGCCAAG TC

ACTGGCCA TCATTGTGGG GCTCTTTGCC CTCTGCTGGC TGCCCCTA

CA CATCATCAAC TGCTTCACTT TCTTCTGCCC CGACTGCAGC CAC

GCCCCTC TCTGGCTCAT GTACCTGGCC ATCGTCCTCT CCCACACCA
```

-continued

A TTCGGTTGTG AATCCCTTCA TCTACGCCTA

CCGTATCCGCGAGTTCCGCCAGACCTTCCGCAAGATCATTCGCAGCCACG

TCCTGAGGCAGCAAGAACCTTTCAAGGCAG CTGGCACCAGTGCCCGGGT

CGTGAGCAAGGGCGAGGAGCTGTTCACCGGGGTGGTGCCCATCCTGGTCG

AGCTGGACGGCGACGTAAACGGCCACAAGTTCAGCGTGTCCGGCGAGGGC

GAGGGCGATGCCACCTACGGCAAGCTGACCCTGAAGTTCATCTGCACCAC

CGGCAAGCTGCCCGTGCCCTGGCCCACCCTCGTGACCACCTTCGGCTACG

GCCTGCAG

TGTTCGCCCGCTACCCCGACCACATGAAGCAGCACGACTTCTTCAAGTCC
GCCATGCCCGAAGGCTACGTCCAGGAGCG

CACCATCTTCTTCAAGGACGACGGCAACTACAAGACCCGCGCCGAGGTGA
AGTTCGAGGGCGACACCCTGGTGAACCGCA

TCGAGCTGAAGGGCATCGACTTCAAGGAGGACGGCAACATCCTGGGGCAC
AAGCTGGAGTACAACTACAACAGCCACAAC

GTCTATATCATGGCCGACAAGCAGAAGAACGGCATCAAGGTGAACTTCAA
GATCCGCCACAACATCGAGGACGGCAGCGT

GCAGCTCGCCGACCACTACCAGCAGAACACCCCCATCGGCGACGGCCCCG
TGCTGCTGCCCGACAACCACTACCTGAGCT

ACCAGTCCGCCCTGAGCAAAGACCCCAACGAGAAGCGCGATCACATGGTC
CTGCTGGAGTTCGTGACCGCCGCCGGGATC

*ACTCT*

SEQ ID NO: 16: A2A-CFP14/10-YFP-C33 amino acid
sequence; "A2A chameleon"
MPIMGSSVYITVELAIAVLAILGNVLVCWAVWLNSNLQNVTNYFVSLAAA

DIAVGVLAIPFAITISTGFCAACHGCLFIACFVLVLTQSSIFSLLAIAID

RYIAIRIPLRYNGLVTGTRAKGIIAICWVLSFAIGLTPMLGWNNCGQPKE

GKNHSQGCGEGQVACLFEDVVPMNYMVYFNFFACVLVPLLLMLGVYLRIF

LAARRQLKQMEVSKGEELFTGVVPILVELDGDVNGHKFSVSGEGEGDATY

GKLTLKFICTTGKLPVPWPTLVTTLTWGVQCFSRYPDHMKQHDFFKSAMP

EGYVQERTIFFKDDGNYKTRAEVKFEGDTLVNRIELKGIDFKEDGNILGH

KLEYNYISHNVYITADKQKNGIKANFKIRHNIEDGSVQLADHYQQNTPIG

DGPVLLPDNHYLSTQSALSKDPNEKRDHMVLLEFVTAAGITLGMDELYKL

QKEVHAAKSLAIIVGLFALCWLPLHIINCFTFFCPDCSHAPLWLMYLAIV

LSHTNSVVNPFIYAYRIREFRQTFRKIIRSHVLRQQEPFKAAGTSARVMV

SKGEELFTGVVPILVELDGDVNGHKFSVSGEGEGDATYGKLTLKFICTTG

KLPVPWPTLVTTFGYGLQCFARYPDHMKQHDFFKSAMPEGYVQERTIFFK

DDGNYKTRAEVKFEGDTLVNRIELKGIDFKEDGNILGHKLEYNYNSHNVY

IMADKQKNGIKVNFKIRHNIEDGSVQLADHYQQNTPIGDGPVLLPDNHYL

SYQSALSKDPNEKRDHMVLLEFVTAAGITLGMDE

Further chameleon-constructs, in particular, PTH-constructs are defined by appended SEQ ID NOS: 29 to 37. A control-construct as employed in accordance with this invention is appended in SEQ ID NO: 38.

Loops and C-termini to be modified for chameleon-constructs of the invention are exemplified in the following SEQ ID NOS: 17 to 28.

SEQ ID NO: 17: Mouse alpha2a adrenergic receptor
third intracellular loop cDNA sequence:
GTGCGTATTTACCAGATCGCCAAGCGTCGCACCCGCGTGCCTCCCAGCCG
CCGGGGTCCGGACGCCTGTTCCGCGCCGCC GGGGGGCGCCGATCGCAGGCCCAACGGGCTGGGCCCGGAGCGCGGCGCGG
GTCCCACGGGCGCTGAGGCGGAGCCGCTGC CCACCCAGCTTAACGGTGCCCCGGGGGAGCCCGCGCCCGCCGGGCCCCGC
GATGGGGATGCGCTGGACCTAGAGGAGAGT TCGTCGTCCGAGCACGCCGAGCGGCCCCCGGGGCCCCGCAGACCCGACCG
CGGCCCCCGAGCCAAGGGCAAGACCCGGGC

GAGTCAGGTGAAGCCGGGGACAGTCTGCCGCGGCGCGGGCCCGGGGCCG
CGGGGCCGGGGGCTTCGGGGTCCGGGCACG

GAGAGGAGCGCGGCGGGGCGCCAAAGCGTCGCGCTGGCGCGGGAGGCAA
AACCGGGAGAAACGCTTCACGTTCGTG

SEQ ID NO: 18: Mouse alpha2a adrenergic receptor
third intracellular loop amino acid sequence:
VRIYQIAKRRTRVPPSRRGPDACSAPPGGADRRPNGLGPERGAGPTGAEA
EPLPTQLNGAPGEPAPAGPRDGDALDLEES

SSSEHAERPPGPRRPDRGPRAKGKTRASQVKPGDSLPRRGPGAAGPGASG
SGHGEERGGGAKASRWRGRQNREKRFTFV

SEQ ID NO: 19: Mouse alpha2a adrenergic receptor
carboxy terminus tail cDNA sequence:
CACGACTTCCGACGCGCCTTCAAGAAGATCCTCTGCCGTGGGGACAGAAA
ACGCATCGTGTGA SEQ ID NO: 20: Mouse alpha2a adrenergic receptor
carboxy terminus tail amino acid sequence:
HDFRRAFKKILCRGDRKRIV SEQ ID NO. 21: human A2A adenosine receptor
3$^{rd}$.loop sequence cDNA:
GGATCTTCCTGGCGGCGCGACGACAGCTGAAGCAGATGGAGAGCCAGCCT
CTGCCGGGGGAGCGGGCACGGTCCACACTGCAGAAGGAGGTCCATGCTGC
CAAGTCA SEQ ID NO: 22: human A2A adenosine receptor
3$^{rd}$.loop amino acid sequence:
RIFLAARRQLKQMESQPLPGERARSTLQKEVHAAKS SEQ ID NO: 23: human A2A adenosine receptor
c-terminus cDNA sequence:
CGTATCCGCGAGTTCCGCCAGACCTTCCGCAAGATCATTCGCAGCCACGT
CCTGAGGCAGCAAGAACCTTTCAAGGCAGCTGGCACCAGTGCCCGGGTCT
TGGCAGCTCATGGCAGTGACGGAGAGCAGGTCAGCCTCCGTGTCAACGGC
CACCCGCCAGGAGTGTGGGCCAACGGCAGTGCTCCCCACCCTGAGCGGAG
GCCCAATGGCTATGCCCTGGGGCTGGTGAGTGGAGGGAGTGCCCAAGAGT
CCCAGGGGAACACGGGCCTCCCAGACGTGGAGCTCCTTAGCCATGAGCTC
AAGGGAGTGTGCCCAGAGCCCCCTGGCCTAGATGACCCCCTGGCCCAGGA
TGGAGCAGGAGTGTCCTGA SEQ ID NO: 24: human A2A adenosine receptor
c-terminus amino acid sequence:
RIREFRQTFRKIIRSHVLRQQEPFKAAGTSARVLAAHGSDGEQVSLRLNG
HPPGVWANGSAPHPERRPNGYALGLVSGGSAQESQGNTGLPDVELLSHEL
KG SEQ ID NO: 25: human PTH/PTHrP receptor third
intracellular loop cDNA sequence:
ACCAAGCTGCGGGAGACCAACGCCGGCCGGTGTGACACACGGCAGCAGTA
CCGGAAG SEQ ID NO: 26: human PTH/PTHrP receptor third
intracellular loop amino acid sequence:
TKLRETNAGRCDTRQQYRK SEQ ID NO: 27: human PTH/PTHrP receptor carboxy
terminus cDNA sequence:
GAGGTACAAGCTGAGATCAAGAAATCTTGGAGCCGCTGGACACTGGCACT
GGACTTCAAGCGAAAGGCACGCAGCGGGAG CAGCAGCTATAGCTACGGCCCCATGGTGTCCCACACAAGTGTGACCAATG
TCGGCCCCCGTGTGGGACTCGGCCTGCCCC

TCAGCCCCCGCCTACTGCCCACTGGCACCACCAACGGCCACCCTCAGCTG
CCTGGCCATGCCAAGCAGGGACCCCAGCC

CTGGAGACCCTCGAGACCACACCACCTGCCATGGCTGCTCCCAAGGACGA
TGGGTTCCTCAACGGCTCCTGCTCAGGCCT

GGACGAGGAGGCCTCTGGGCCTGAGCGGCCACCTGCCCTGCTACAGGAAG
AGTGGGAGACAGTCATGTGATGA

SEQ ID NO: 28: human PTH/PTHrP receptor carboxy
terminus amino acid sequence:
EVQAEIKKSWSRWTLALDFKRKARSGSSSYSYGPMVSHTSVTNVGPRVGL
GLPLSPRLLPTATTNGHPQLPGHAKPGTPA

LETLETTPPAMAAPKDDGFLNGSCSGLDEEASGPERPPALLQEEWETVM

As mentioned above, further exemplifying PTH/PTHrP receptor chameleons have been constructed. These constructs, in particular relate to amino acid sequence junction between PTH/PTHrP receptor's carboxy terminal tail and YFP for various PTH receptor-cam constructs.

The best FRET efficiency are in the following order: PTHR-cam8>PTHR-cam9>PTHR-cam7>PTHR-cam2>PTHR-cam5>PTHR-cam 1>PTHR-cam4≧PTHR-cam3=PTHR-cam10. PTH mediated a FRET decrease in these constructions.

PTHR-cam8 is the construct described above in SEQ ID NOS: 13 and 14.

Further constructs are defined below. These constructs correspond to PTHR-cam8, yet, they comprise a modified C-terminus.

SEQ ID NO: 29: PTKR-cam7 amino acid sequence:
**EVQAEIKKSWSRWTLALDFKRKARSMVSKGEELFTGVVPILVELDGDVNG
HKFSVSGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 30: PTHR-cam9 amino acid sequence:
EVQAEIKKSWSRWTLALDFKRKARSGSSSYS**MVSKGEELFTGVVPILVEL
DGDVNGHKFSVSGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 31: PTHR-cam8 amino acid sequence:
EVQAEIKKSWSRWTLALDFKRKARSGSSSYSYG**MVSKGEELFTGVVPILV
ELDGDVNGHKFSVSGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 32: PTHR-cam2 amino acid sequence:
EVQAEIKKSWSRWTLALDFKRKARSGSSSYSYGPMV**MVSKGEELFTGVVP
ILVELDGDVNGHKFSVSGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 33: PTHR-cam5 amino acid sequence:
EVQAEIKKSWSRWTLALDFKRKARSGSSSYSYGPMVSHTSVTNVGPRVGL
**MVSKGEELFTGVVPILVELDGDVNGHKFSVSGEGEGDATYGKLTLKFICT
TGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 34: PTHR-cam1 amino acid sequence:
EVQAEIKKSWSRWTLALDFKRKARSGSSSYSYGPMVSHTSVTNVGPRVGL
GLPLSPRLLPTATTNGHPQLPGHAKPGTPA

LETLET**MVSKGEELFTGVVPILVELDGDVNGHKFSVSGEGEGDATYGKLT
LKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 35: PTHR-cam4 amino acid sequence:
EVQAEIKKSWSRWTLALDFKRKARSGSSSYSYGPMVSHTSVTNVGPRVGL
GLPLSPRLLPTATTNGHPQLPGHAKPGTPA LETLETTPPAMAAPKDDGFL**MVSKGEELFTGVVPILVELDGDVNGHKFSV
SGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 36: PTHR-cam3 amino acid sequence:
EVQAEIKKSWSRWTLALDFKRKARSGSSSYSYGPMVSHTSVTNVGPRVGL
GLPLSPRLLPTATTNGHPQLPGHAKPGTPA LETLETTPPAMAAPKDDGFLNGSCSGLDEEASGPE**MVSKGEELFTGVVPI
LVELDGDVNGHKFSVSGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

NYNSHNVYIMADKQKNGIKVNFKIRHNIEDGSVQLADHYQQNTPIGDGPV
LLPDNHYLSYQSALSKDPNEKRDHMVLLEF

VTAAGITLGMDELYK

SEQ ID NO: 37: PTHR-cam10 amino acid sequence:
EVQAEIKKSWSRWTLALDFKRKARSGSSSYSYGPMVSKTSVTNVGPRVGL
GLPLSPRLLPTATTNGHPQLPGHAKPGTPA LETLETTPPAMPAPKDDGFLNGSCSGLDEEASGPERPPALLQEEWETVM**M
VSKGEELFTGVVPILVELDGDVNGHKFSVSGEGEGDATYGKLTLKFICTT
GKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

**NYNSHNVYIMADKQKNGIKVNFKIRHNIEDGSVQLADHYQQNTPIGDGPV
LLPDNHYLSYQSALSKDPNEKRDHMVLLEF**

VTAAGITLGMDELYK

The following control construct is exemplified: Amino acid Sequence junction between PTH/PTHrP receptor's carboxy terminal tail and YFP and CFP in PTHR-FRET$^{control}$.

This construction gave a strong FRET efficiency. However, PTH, as ligand, does not mediated a change in FRET in this construction.

SEQ ID NO: 38: PTHR-PTHR-FRET$^{control}$ amino acid sequence:
EVQAEIKKSWSRWTLALDFKRKAR**MVSKGEELFTGVVPILVELDGDVNGH
KFSVSGEGEGDATYGKLTLKFICTTGKLPVPWPTLVTT**

**FGYGLQCFARYPDHMKQHDFFKSAMPEGYVQERTIFFKDDGNYKTRAEVK
FEGDTLVNRIELKGIDFKEDGNILGHKLEY**

**NYNSHNVYIMADKQKNGIKVNFKIRHNIEDGSVQLADHYQQNTPIGDGPV
LLPDNHYLSYQSALSKDPNEKRDHMVLLEF**

VTAAGITLGMDELYKSGSSSYSYGPMVSHTSMVSKG

**EELFTGVVPILVELDGDVNGHKFSVSGEGEGDATYGKLTLKFICTTGKLP
VPWPTLVTTLTWGVQCFSRYPDHMKQHDFF**

**KSAMPEGYVQERTIFFKDDGNYKTRAEVKFEGDTLVNRIELKGIDFKEDG
NILGHKLEYNYISHNVYITADKQKNGIKAN**

**FKIRHNIEDGSVQLADHYQQNTPIGDGPVLLPDNHYLSTQSALSKDPNEK
RDHMVLLEFVTAAGITLGMDELYK**

Further constructs comprise

SEQ ID No 39: A2A-FIAsHPG-CFP-C49 cDNA sequence
ATGCCCATCATGGGCTCCTCGGTGTACATCACGGTGGAGCTGGCCATTGC
TGTGCTGGCCATCCTGGGCAATGTGCTGGTGTGCTGGGCCGTGTGGCTCA
ACAGCAACCTGCAGAACGTCACCAACTACTTTGTGGTGTCACTGGCGGCG
GCCGACATCGCAGTGGGTGTGCTCGCCATCCCCTTTGCCATCACCATCAG
CACCGGGTTCTGCGCTGCCTGCCACGGCTGCCTCTTCATTGCCTGCTTCG
TCCTGGTCCTCACGCAGAGCTCCATCTTCAGTCTCCTGGCCATCGCCATT
GACCGCTACATTGCCATCCGCATCCCGCTCCGGTACAATGGCTTGGTGAC
CGGGACGAGGGCTAAGGGCATCATTGCCATCTGCTGGGTGCTGTCGTTTG
CCATCGGCCTGACTCCCATGCTAGGTTGGAACAACTGCGGTCAGCCAAAG
GAGGGCAAGAACCACTCCCAGGGCTGCGGGGAGGGCCAAGTGGCCTGTCT
CTTTGAGGATGTGGTCCCCATGAACTACATGGTGTACTTCAACTTCTTTG
CCTGTGTGCTGGTGCCCCTGCTGCTCATGCTGGGTGTCTATTTGCGGATC
TTCCTGGCGGCGCGACGACAGCTGAAGCAGATGGAGAGCCAGT**GTTGTCC
GGGGTGTTGT**GCACGGTCCACACTGCAGAAGGAGGTCCATGCTGCCAGT
CACTGGCCATCATTGTGGGGCTCTTTGCCCTCTGCTGGCTGCCCCTACAC
ATCATCAACTGCTTCACTTTCTTCTGCCCCGACTGCAGCCACGCCCCTCT
CTGGCTCATGTACCTGGCCATCGTCCTCTCCCACACCAATTCGGTTGTGA
ATCCCTTCATCTACGCCTACCGTATCCGCGAGTTCCGCCAGACGTTCCGC
AAGATCATTCGCAGCCACGTCCTGAGGCAGAAGAACCTTTCAAGGCAGC
TGGCACCAGTGCCCGGGTCTTGGCAGCTCATGGCAGTGACGGAGAGCAGG
TCAGCCTCCGTCTCAACGGT**GTGAGCAAGGGCGAGGAGCTGTTCACCGGG
GTGGTGCCCATCCTGGTCGAGCTGGACGGCGACGTAAACGGCCACAGGTT
CAGCGTGTCCGGCGAGGGCGAGGGCGATGCCACCTACGGCAAGCTGACCC
TGAAGTTCATCTGCACCACCGGCAAGCTGCCCGTGCCCTGGCCCACCCTC
GTGACCACCCTGACCTGGGGCGTGCAGTGCTTCAGCCGCTACCCCGACCA
CATGAAGCAGCACGACTTCTTCAAGTCCGCCATGCCCGAAGGCTACGTCC
AGGAGCGTACCATCTTCTTCAAGGACGACGGCAACTACAAGACCCGCGCC
GAGGTGAAGTTCGAGGGCGACACCCTGGTGAACCGCATCGAGCTGAAGGG
CATCGACTTCAAGGAGGACGGCAACATCCTGGGGCACAAGCTGGAGTACA
ACTACATCAGCCACAACGTCTATATCACCGCCGACAAGCAGAAGAACGGC
ATCAAGGCCCACTTCAAGATCCGCCACAACATCGAGGACGGCAGCGTGCA
GCTCGCCGACCACTACCAGCAGAACACCCCCATCGGCGACGGCCCCGTGC
TGCTGCCCGACAACCACTACCTGAGCACCCAGTCCGCCCTGAGCAAAGAC
CCCAACGAGAAGCGCGATCACATGGTCCTGCTGGAGTTCGTGACCGCCGC
CGGGATCACTCTCGGCATGGACGAGCTGTACAAGTAA**

SEQ ID No 40: A2A-FIAsHPG-CFP-C49 amino acid sequence
MPIMGSSVYITVELAIAVLAILGNVLVCWAVWLNSNLQNVTNYFVVSLAA
ADIAVGVLAIPFAITISTGFCAACHGCLFIACFVLVLTQSSIFSLLAIAI
DRYIAIRIPLRYNGLVTGTRAKGIIAICWVLSFAIGLTPMLGWNNCGQPK
EGKNHSQGCGEGQVACLFEDVVPMNYMVYFNFFACVLVPLLLMLGVYLRI
FLAARRQLKQMESQCCPGCCARSTLQKEVHAAKSLAIIVGLFALCWLPLH
IINCFTFFCPDCSHAPLWLMYLAIVLSHTNSVVNPFIYAYRIREFRQTFR
KIIRSHVLRQQEPFKAAGTSARVLAAHGSDGEQVSLRLNG**VSKGEELFTG
VVPILVELDGDVNGHRFSVSGEGEGDATYGKLTLKFICTTGKLPVPWPTL
VTTLTWGVQCFSRYPDHMKQHDFFKSAMPEGYVQERTIFFKDDGNYKTRA
EVKFEGDTLVNRIELKGIDFKEDGNILGHKLEYNYISHNVYITADKQKNG
IKAHFKIRHNIEDGSVQLADHYQQNTPIGDGPVLLPDNHYLSTQSALSKD
PNEKRDHMVLLEFVTAAGITLGMDELYK**

SEQ ID No 41: A2A-FIAsHPG-CFP-C33 cDNA sequence
ATGCCGATCATGGGCTCCTCGGTGTACATCACGGTGGAGCTGGCCATTGC
TGTGCTGGCCATCCTGGGCAATGTGCTGGTGTGCTGGGCCGTGTGGCTCA
ACAGCAACCTGCAGAACGTCACCAACTACTTTGTGGTGTCACTGGCGGCG
GCCGACATCGCAGTGGGTGTGCTCGCCATCCCCTTTGCCATCACCATCAG
CACCGGGTTCTGCGCTGCCTGCCACGGCTGCCTCTTCATTGCCTGCTTCG
TCCTGGTCCTCACGCAGAGCTCCATCTTCAGTCTCCTGGGCATCGCCATT GACCGCTACATTGCCATCCGCATCCCGCTCCGGTACAATGGCTTGGTGAC
CGGGACGAGGGCTAAGGGCATCATTGCCATCTGCTGGGTGCTGTCGTTTG
CCATCGGCCTGACTCCCATGCTAGGTTGGAACAACTGCGGTCAGCCAAAG
GAGGGCAAGAACCACTCCCAGGGCTGCGGGGAGGGCCAAGTGGCCTGTCT
CTTTGAGGATGTGGTCCCCATGAACTACATGGTGTACTTCAACTTCTTTG
CCTGTGTGCTGGTGCCCCTGCTGCTCATGCTGGGTGTCTATTTGCGGATC
TTCCTGGCGGCGCGACGACAGCTGAAGCAGATGGAGAGCCAGTGTTGTCC
GGGGTGTTGTGCACGGTCCACACTGCAGAAGGAGGTCCATGCTGCCAAGT
CACTGGCCATCATTGTGGGGCTCTTTGCCCTCTGCTGGCTGCCCCTACAC
ATCATCAACTGCTTCACTTTCTTCTGCCCCGACTGCAGCCACGCCCCTCT
CTGGCTCATGTACCTGGCCATCGTCCTCTCCCACACCAATTCGGTTGTGA
ATCCCTTCATCTACGCCTACCGTATCCGCGAGTTCCGCCAGACCTTCCGC
AAGATCATTCGCAGCCACGTCCTGAGGCAGCAAGAACCTTTCAAGGCAGC
TGGCACCAGTGCCCGGGTCGTGAGCAAGGGCGAGGAGCTGTTCACCGGGG
TGGTGCCCATCCTGGTCGAGCTGGACGGCGACGTAAACGGCCACAGGTTC
AGCGTGTCCGGCGAGGGCGAGGGCGATGCCACCTACGGCAAGCTGACCCT
GAAGTTCATCTGCACCACCGGCAAGCTGCCCGTGCCCTGGCCCACCCTCG
TGACCACCCTGACCTGGGGCGTGCAGTGCTTCAGCCGCTACCCCGACCAC
ATGAAGCAGCACGACTTCTTCAAGTCCGCCATGCCCGAAGGCTACGTCCA
GGAGCGTACCATCTTCTTCAAGGACGACGGCAACTACAAGACCCGCGCCG
AGGTGAAGTTCGAGGGCGACACCCTGGTGAACCGCATCGAGCTGAAGGGC
ATCGACTTCAAGGAGGACGGCAACATCCTGGGGCACAAGCTGGAGTACAA
CTACATCAGCCACAACGTCTATATCACCGCCGACAAGCAGAAGAACGGCA
TCAAGGCCCACTTCAAGATCCGCCACAACATCGAGGACGGCAGCGTGCAG
CTCGCCGACCACTACCAGCAGAACACCCCCATCGGCGACGGCCCCGTGCT
GCTGCCCGACAACCACTACCTGAGCACCCAGTCCGCCCTGAGCAAAGACC
CCAACGAGAAGCGCGATCACATGGTCCTGCTGGAGTTCGTGACCGCCGCC
GGGATCACTCTCGGCATGGACGAGCTGTACAAGTAA

SEQ ID No 42: A2A-FlAsHPG-CFP-C33 amino acid
sequence
MPIMGSSVYITVELAIAVLAILGNVLVCWAVWLNSNLQNVTNYFVVSLAA
ADIAVGVLAIPFAITISTGFCAACHGCLFIACFVLVLTQSSIFSLLAIAI
DRYIAIRIPLRYNGLVTGTRAKGIIAICWVLSFAIGLTPMLGWNNCGQPK
EGKNHSQGCGEGQVACLFEDVVPMNYMVYFNFFACVLVPLLLMLGVYLRI
FLAARRQLKQMESQCCPGCCARSTLQKEVHAAKSLAIIVGLFALCWLPLH
IINCFTFFCPDCSHAPLWLMYLAIVLSHTNSVVNPFIYAYRIREFRQTFR
KIIRSHVLRQQEPFKAAGTSARVVSKGEELFTGVVPILVELDGDVNGHRF
SVSGEGEGDATYGKLTLKFICTTGKLPVPWPTLVTTLTWGVQCFSRYPDH
MKQHDFFKSAMPEGYVQERTIFFKDDGNYKTRAEVKFEGDTLVNRIELKG
DFKEDGNILGHKLEYNYISHNVYITADKQKNGIKAHFKIRHNIEDGSVQL
ADHYQQNTPIGDGPVLLPDNHYLSTQSALSKDPNEKRDHMVLLEFVTAAG
ITLGMDELYK

SEQ ID No 43: A2A-CFP-ModelPG-C49 cDNA sequence
ATGCCCATCATGGGCTCCTCCGGTGTACATCACGGTGGAGCTGGCCATTGC
TGTGCTGGCCATCCTGGGCAATGTGCTGGTGTGCTGGGCCGTGTGGCTCA
ACAGCAACCTGCAGAACGTCACCAACTACTTTGTGGTGTCACTGGCGGCG
GCCGACATCGCAGTGGGTGTGCTCGCCATCCCCTTTGCCATCACCATCAG
CACCGGGTTCTGCGCTGCCTGCCACGGCTGCCTCTTCATTGCCTGCTTCG
TCCTGGTCCTCACGCAGAGCTCCATCTTCAGTCTCCTGGCCATCGCCATT
GACCGCTACATTGCCATCCGCATCCCGCTCCGGTACAATGGCTTGGTGAC
CGGCACGAGGGCTAAGGGCATCATTGCCATCTGCTGGGTGCTGTCGTTTG
CCATCGGCCTGACTCCCATGCTAGGTTGGAACAACTGCGGTCAGCCAAAG
GAGGGCAAGAACCACTCCCAGGGCTGCGGGGAGGGCCAAGTGGCCTGTCT
CTTTGAGGATGTGGTCCCCATGAACTACATGGTGTACTTCAACTTCTTTG
CCTGTGTGCTGGTGCCCCTGCTGCTCATGCTGGGTGTCTATTTGCGGATC
TTCCTGGCGGCGCGACGACAGCTGAAGCAGATGGAGAGCCAGCCTCTGCC
GGGGGAGCGGGCACGGTCCACACTGCAGAAGGAGGTCCATGCTGCCAAGT
CACTGGCCATCATTGTGGGGCTCTTTGCCCTCTGCTGGCTGCCCCTACAC
ATCATCAACTGCTTCACTTTCTTCTGCCCCGACTGCAGCCACGCCCCTCT
CTGGCTCATGTACCTGGCCATCGTCCTCTCCCACACCAATTCGGTTGTGA
ATCCCTTCATCTACGCCTACCGTATCCGCGAGTTCCGCCAGACCTTCCGC
AAGATCATTCGCAGCCACGTCCTGAGGCAGCAAGAACCTTTCAAGGCAGC
TGGCACCAGTGCCCGGGTCTTGGCAGCTCATGGCAGTGACGGAGAGCAGG
TCAGCCTCCGTCTCAACGGCGTGAGCAAGGGCGAGGAGCTGTTCACCGGG
GTGGTGCCCATCCTGGTCGAGCTGGACGGCGACGTAAACGGCCACAGGTT
CAGCGTGTCCGGCGAGGGCGAGGGCGATGCCACCTACGGCAAGCTGACCC
TGAAGTTCATCTGCACCACCGGCAAGCTGCCCGTGCCCTGGCCCACCCTC
GTGACCACCCTGACCTGGGGCGTGCAGTGCTTCAGCCGCTACCCCGACCA
CATGAAGCAGCACGACTTCTTCAAGTCCGCCATGCCCGAAGGCTACGTCC
AGGAGCGTACCATCTTCTTCAAGGACGACGGCAACTACAAGACCCGCGCC
GAGGTGAAGTTTCGAGGGCGACACCCTGGTGAACCGCATCGAGCTGAAGG
GCATCGACTTCAAGGAGGACGGCAACATCCTGGGGCACAAGCTGGAGTAC
AACTACATCAGCCACAACGTCTATATCACCGCCGACAAGCAGAAGAACGG
CATCAAGGCCCACTTCAAGATCCGCCACAACATCGAGGACGGCAGCGTGC
AGCTCGCCGACCACTACCAGCAGAACACCCCCATCGGCGACGGCCCCGTG
CTGCTGCCCGACAACCACTACCTGAGCACCCAGTCCGCCCTGAGCAAAGA
CCCAACGAGAAGCGCGATCACATGGTCCTGCTGGAGTTCGTGACCGCCG
CCGGGATCACTCTCGGCATGGACGAGCTGTACAAG+EEGCTGAGGCTGC
AGCG
CGCGAAGCATGCTGCCCAGGTTGTTGCGCTCGCGCATGA SEQ ID No 44: A2A-CFP-ModelPG-C49 amino acid sequence
MPIMGSSVYITVELAIAVLAILGNVLVCWAVWLNSNLQNVTNYFWSLAAA
DIAVGVLAIPFAITISTGFCAACHGCLFIACFVLVLTQSSIFSLLAIAID
RYIAIRIPLRYNGLVTGTRAKGIIAICWVLSFAIGLTPMLGWNNCGQPKE
GKNHSQGCGEGQVACLFEDVVPMNYMVYFNFFACVLVPLLLMLGVYLRIF
LAARRQLKQMESQPLPGERARSTLQKEVHAAKSLAIIVGLFALCWLPLHI
INCFTFFCPDCSHAPLWLMYLAIVLSHTNSVVNPFIYAYRIREFRQTFRK
IIRSHVLRQQEPFKAAGTSARVLAAHGSDGEQVSLRLNGVSKGEELFTGV
VPILVELDGDVNGHRFSVSGEGEGDATYGKLTLKFICTTGKLPVPWPTLV
TTLTWGVQCFSRYPDHMKQHDFFKSAMPEGYVQERTIFFKDDGNYKTRAE
VKFEGDTLVNRIELKGIDFKEDGNILGHKLEYNYISHNVYITADKQKNGI
KAHFKIRHNIEDGSVQLADHYQQNTPIGDPVLLPDNHYLSTQSALSKDP
NEKRDHMVLLEFVTAAGITLGMDELYKAEAAAREACCPGCCARA SEQ ID No 45: A2A-CFP-C49 cDNA sequence
ATGCCCATCATGGGCTCCTCGGTGTACATCACGGTGGAGCTGGCCATTGC
TGTGCTGGCCATCCTGGGCAATGTGCTGGTGTGCTGGGCCGTGTGGCTCA
ACAGCAAGCTGCAGAACGTCACCAACTACTTTGTGGTGTCACTGGCGGCG
GCCGACATCGCAGTGGGTGTGCTCGCCATCCCCTTTGCCATCACCATCAG
CACCGGGTTCTGCGCTGCCTGCCACGGCTGCCTCTTCATTGCCTGCTTCG
TCCTGGTCCTCACGCAGAGCTCCATCTTCAGTCTCCTGGCCATCGCCATT
GACCGCTACATTGCGATCCGCATCCCGCTCGGGTACAATGGCTTGGTGAC
CGGCACGAGGGCTAAGGGCATCATTGCCATCTGCTGGGTGCTGTCGTTTG
CCATCGGCCTGACTCCCATGCTAGGTTGGAACAACTGCGGTCAGCCAAAG
GAGGGCAAGAACCACTCCCAGGGCTGCGGGGAGGGCCAAGTGGCCTGTCT
CTTTGAGGATGTGGTCCCCATGAACTACATGGTGTACTTCAACTTCTTTG
CCTGTGTGCTGGTGCCCCTGCTGCTCATGCTGGGTGTCTATTTGCGGATC
TTCCTGGCGGCGCGACGACAGCTGAAGCAGATGGAGAGCCAGCCTCTGCC
GGGGGAGCGGGCACGGTCCACACTGCAGAAGGAGGTCCATGCTGCCAAGT
CACTGGCCATCATTGTGGGGCTCTTTGCCCTCTGCTGGCTGCCCCTACAC
ATCATCAACTGCTTCACTTTCTTCTGCCCCGACTGCAGCCACGCCCCTCT
CTGGCTCATGTACCTGGCCATCGTCCTCTCCCACACCAATTCGGTTGTGA
ATCCCTTCATCTACGCCTACCGTATCCGCGAGTTCCGCCAGACCTTCCGC
AAGATCATTCGCAGCCACGTCCTGAGGCAGCAAGAACCTTTCAAGGCAGC
TGGCACCAGTGCCCGGGTCTTGGCAGCTCATGGCAGTGACGGAGAGCAGG
TCAGCCTCCGTCTCAACGGTGTGAGCAAGGGCGAGGAGCTGTTCACCGGG
GTGGTGCCCATCCTGGTCGAGCTGGACGGCGACGTAAACGGCCACAGGTT
CAGCGTGTCCGGCGAGGGCGAGGGCGATGCCACCTACGGCAAGCTGACCC
TGAAGTTCATCTGCACCACCGGCAAGCTGCCCGTGCCCTGGCCCACCCTC
GTGACCACCCTGACCTGGGGCGTGCAGTGCTTCAGCCGCTACCCCGACCA
CATGAAGCAGCACGACTTCTTCAAGTCCGCCATGCCCGAAGGCTACGTCC
AGGAGCGTACCATCTTCTTCAAGGACGACGGCAACTACAAGACCCGCGCC
GAGGTGAAGTTCGAGGGCGACACCCTGGTGAACCGCATCGAGCTGAAGGG
CATCGACTTCAAGGAGGACGGCAACATCCTGGGGCACAAGCTGGAGTACA
ACTACATCAGCCACAACGTCTATATCACCGCCGACAAGCAGAAGAACGGC
ATCAAGGCCCACTTCAAGATCCGCCACAAGATCGAGGACGGCAGCGTGCA
GCTCGCCGACCACTACCAGCAGAACACCCCCATCGGCGACGGCCCCGTGC
TGCTGCCCGACAACCACTACCTGAGCACCCAGTCCGCCCTGAGCAAAGAC
CCCAACGAGAAGCGCGATCACATGGTCCTGCTGGAGTTCGTGACCGCCGC
CGGGATCACTCTCGGCATGGACGAGCTGTACAAGTAA SEQ ID No 46: A2A-CFP-C49 amino acid sequence
MPIMGSSVYITVELAIAVLAILGNVLVCWAVWLNSNLQNVTNYFVVSLAA
ADIAVGVLAIPFAITISTGFCAACHGCLFIACFVLVLTQSSIFSLLAIAI
DRYIAIRIPLRYNGLVTGTRAKGIIAICWVLSFAIGLTPMLGWNNCGQPK
EGKNHSQGCGEGQVACLFEDVVPMNYMVYFNFFACVLVPLLLMLGWLRIF
LAARRQLKQMESQPLPGERARSTLQKEVHAAKSLAIIVGLFALCWLPLHI
INCFTFFCPDCSHAPLWLMYLAIVLSHTNSVVNPFIYAYRIREFRQTFRK
IIRSHVLRQQEPFKAAGTSARVLAAHGSDGEQVSLRLNGVSKGEELFTGV
VPILVELDGDVNGHRFSVSGEGEGDATYGKLTLKFICTTGKLPVPWPTLV
TTLTWGVQCFSRYPDHMKQHDFFKSAMPEGWQERTIFFKDDGNYKTRAEV
KFEGDTLVNRIELKGIDFKEDGNILGHKLEYNYISHNWITADKQKNGIKA
HFKIRHNIEDGSVQLADHYQQNTPIGDPVLLPDNHYLSTQSALSKDPNE
KRDHMVLLEFVTAAGITLGMDELYK

EXAMPLE II

Generation of Receptor Constructs with Agonist-Sensitive FRET

A series of receptor constructs were generated that carried CFP and/or YFP in various positions of the third intracellular loop and/or of the carboxy-terminus of the PTHR and the $\alpha_{2A}AR$, respectively. The two constructs showing the best cell surface expression, pharmacological properties and agonist sensitivity were further used in this study and are referred to as receptor chameleons PTHR-cam and $\alpha_{2A}AR$-cam (FIG. 1A).

Emission fluorescence spectra were recorded from HEK293 cells stably expressing "PTHR-cam8" and various control constructs. The sequences representing "PTHR-cam8" are represented in appended SEQ ID NOS: 13 and 14. Excitation of a PTHR carrying only a CFP-moiety in its $3^{rd}$ intracellular loop (PTHR-CFP$_{3\text{-}loop}$) with light at 436 nm resulted in an emission at 480 nm (corresponding to the CFP emission, FIG. 1B). The additional presence of YFP in the carboxy terminus (PTHR-cam) lead to a reduced emission at 480 nm plus a strong emission at the characteristic wavelength of YFP (535 nm, FIG. 1B). Photobleaching of the acceptor confirmed that the latter emission was primarily due to FRET (see FIG. 1C). The presence of YFP in the C-terminus alone (PTHR-YFP$_{C\text{-}term}$) did not result in significant emission at 535 nm when excited at 436 nm (FIG. 1B). Receptor constructs containing only YFP showed no specific emission peak at 535 nm when excited at 436 nm (FIG. 1B).

It is of note that further PTHR-cam constructs have been prepared which are shown in related SEQ ID NOS: 29 to 37. A control construct is shown in SEQ ID NO: 38.

Signals recorded from single HEK293 cells expressing PTHR-cam8 were then analysed at emissions of 480 nm (CFP) and 535 nm (YFP) upon excitation at 436 nm (CFP excitation). The microscopic illumination allowed photobleaching experiments in order to verify that the emission at 535 nm was indeed due to FRET. After bleaching of the acceptor in the PTHR-cam8 construct with intense light at 480. nm, the emission at 480 nm increased by 50±3% together with a more than 5-fold reduction of the 535 nm emission (FIG. 1C). Similar spectral and photobleaching data were obtained with the "$\alpha_{2A}$AR-cam" stably expressed in HEK293 cells. The corresponding constructs for "$\alpha_{2A}$AR-cam" are depicted in SEQ ID NOS: 11 and 12.

The effects of the agonist PTH on the FRET signal of PTHR-cam were investigated, measured as the background-corrected emission intensity ratio $F^*_{535}/F^*_{480}$. After addition of 1 μM PTH, the ratio $F^*_{535}/F^*_{480}$ rapidly decreased (FIG. 1D). After a short delay (≈600 ms) the decrease followed a mono-exponential time-course with a time-constant τ=3.00±0.25 s (n=9). The symmetrical increase in CFP emission and decrease in YFP emission indicate that the change was due to a decrease in FRET. Control experiments with co-expression of PTHR-CFP$_{3\text{-}loop}$ and PTHR-YFP$_{C\text{-}term}$ showed no FRET in the absence or in the presence of PTH (1 μM) and thus made it unlikely that the signals resulted from intermolecular FRET in receptor dimers. It should be noted, however, that the intramolecular nature of this signal does not exclude the presence of receptor dimers.

Similarly, $\alpha_{2A}$AR-cam showed intramolecular FRET, and again the specific agonist, i.e. noradrenaline, caused a decline of the FRET signal (see FIGS. 3, 4, 6). Virtually identical results were obtained with the two receptors expressed in other cell lines (CHO, PC12; data not shown). The agonist-induced decreases in FRET in the two types of receptors suggest that the agonist-induced conformational switch is similar in class 1 and class 2 GPCRs. Because of the location of the CFP and YFP in the receptors (FIG. 1A) they are compatible with a movement of the $3^{rd}$ intracellular loop away from the C-terminus as predicted by computer simulations of the $\alpha_{1B}$-adrenergic receptor (Greasley, J. Biol. Chem. 276 (2001), 46485-46494).

EXAMPLE III

Pharmacological Characterization of the Receptor-Chameleon

The receptor-chameleon constructs stably expressed in HEK293 cells retained the typical ligand binding which was of somewhat lower affinity than for the corresponding wild-type receptors (FIG. 2): the PTH affinity was $K_i$=15.5±0.9 nM for PTHR-cam and $K_i$=2.4±0.4 nM for PTHR; the nordrenaline affinity was $K_i$=5.0±0.8 for $\alpha_{2A}$AR and $K_i$=16.7±1.4 μM for $\alpha_{2A}$AR-cam. Note that the insertion of the GFP variants into the third loop and carboxy terminus of the receptor might cause a conformational destabilization of the receptor resulting in a deviation in the binding properties of the GPCRs-cam. Such destabilization might result in a faster activation switch of the receptor. However, the $\alpha_{2A}$AR-cam induced GIRK current activation was not faster than the wild type $\alpha_{2A}$AR (Bünemann, (2001), loc. cit.).

PTHR-cam and $\alpha_{2A}$AR-cam signalled efficiently to adenylyl cyclase (EC$_{50}$=12.8±1.4 nM) and to the GIRK channel (EC$_{50}$=1.08±0.01 μM), respectively (FIG. 2A-B). A difference in the signal amplification between PTHR wild type- and PTHR-cam receptors (1 μM PTH mediated 28 vs. 11.5-fold increase in cAMP in HEK-293 cells expressing PTHR or PTHR-cam, respectively) is in part due to the higher expression level of the wild type receptors ($1.01\times10^6$ vs $0.34\times10^6$ receptors/cells for PTHR and PTHR-cam, respectively). Finally, confocal microscopy showed that the majority of PTHR-cam and $\alpha_{2A}$AR-cam receptors in stably transfected cells were correctly present at the cell surface (FIG. 2C). These data indicate that both receptor constructs were properly targeted to the cell surface upon expression in HEK293 cells and retained essential binding properties as well as significant G-protein-mediated signalling of the corresponding wild-type receptors. Similar data were obtained upon expression in various cell lines (e.g. CHO or PC12).

EXAMPLE IV

The Agonist-Mediated FRET Signal is Coupled to Receptor Activation

It was verified that the agonist-induced changes in FRET does indeed reflect the conformational change of the receptor. The following verification experiments were carried out.

First, it was shown that the FRET signal was indeed caused by the receptors themselves and not by interactions with other proteins such as G-proteins or β-arrestins. Therefore, we studied PTHR-cam under conditions that exclude interactions with these proteins. In isolated cell membranes prepared from HEK293 cells stably expressing PTHR-cam—i.e. in the absence of cytosolic proteins—the PTH-induced signal had the same magnitude as in intact cells (FIG. 3A). Further stripping the cell membranes with 6 M urea—a treatment known to leave GPCRs intact but to denature virtually all other proteins (Sheikh, J. Biol. Chem. 274 (1999), 17033-17041; Lim, Biochem. J. 354 (2001), 337-344)—did also not affect the magnitude of the PTH-induced signal at saturating concentrations (FIG. 3A). And finally, inactivating $G_i$ and $G_o$ with pertussis toxin in cells expressing the $\alpha_{2A}$AR-cam did not affect the noradrenaline-induced FRET signal, indicating that the signal was not due to a receptor/G-protein interaction. Taken together, these data document that the FRET signals were not caused by interactions of the receptors with other proteins.

Second, it was shown that the FRET signals correspond to the activation state of the receptor. Accordingly, the effects of agonists and antagonists were tested. A truncated variant of PTH, PTH7-34, which is a low affinity antagonist, failed to induce a change in FRET (FIG. 3A). Similarly, noradrenaline (10 μM) induced a rapid decrease of the FRET signal in the $\alpha_{2A}$AR-cam (FIG. 3B), while saturating concentrations of the high affinity $\alpha_2$-adrenergic receptor antagonist phentolamine (10 μM) did not alter the FRET signal when given alone. However, phentolamine rapidly reverted the noradrenaline-induced signal (FIG. 3B). This is compatible with its nature as a competitive antagonist. Thus, the rigorous agonist dependence on the change of the FRET signal mirrors the active state of the receptor.

Third, binding of G-proteins to receptors is known to enhance formation of the active, agonist-bound state. Because of the reduced ability of the receptor chameleons to couple to G-proteins, such assays required the addition of exogenous G-proteins. After addition of purified $G_o$ to membranes containing $\alpha_{2A}$AR-cam, the agonist [$^3$H]UK14304 bound with high affinity to the receptors ($K_d$=3.4±0.8 nM; Supplementary FIG. 1). Addition of the stable GTP-analog GTPγS reduced this affinity ($K_d$=9.6±1.1 nM) indicative of a disruption of the high-affinity receptor/G-protein complex.

GTPγS reduced the binding of 5 nM [$^3$H]UK14304 by more then 50% (FIG. 3C right panel). Similarly, GTPγS reduced the FRET signals caused by a 5 nM UK14304 in the same membrane preparation (i.e. in the presence of $G_o$) by more than 50% (FIG. 3C left panel). GTPγS did not affect the signal of saturating concentrations of UK14304, which is in agreement with the lack of effect of urea-treatment on the maximal PTH-induced signal obtained in membranes (FIG. 3A). Taken together, these data suggest that the FRET-signal originates in the active conformation of the receptor itself, and that this active conformation binds to and is stabilized by G-proteins.

EXAMPLE V

FRET Changes Mediated by a Partial Agonist

The FRET assay also properly reflected partial agonism (FIG. 4): Compared to the full agonist noradrenaline, the high affinity partial agonist clonidine at saturating concentrations (10 μM) gave a three-fold smaller FRET signal (FIG. 4). Subsequent application of noradrenaline (10 μM) still produced the full response. The simultaneous addition of clonidine (10 μM) restored this response back to the partial response seen with clonidine alone; and again, after washout, noradrenaline still produced the full initial response. These data correspond exactly to the predicted properties of a high affinity partial agonist. However, compared to other assays used so far to detect partial agonism, the FRET assay is not dependent on transducer and effector proteins. Instead it reflects directly the partial agonist effects on the receptors themselves. Mechanistically, the ability of clonidine to partially reverse the agonist-mediated signal suggests that the partial agonist restrains the complete movement between the $3^{rd}$ intracellular loop and the C-terminus. This is compatible with the notion that the partial agonism process occurs at the receptor level by inducing a restrained conformational change within the agonist binding site (Ghanouni, J. Biol. Chem. 276 (2001), 24433-24436).

EXAMPLE VI

Comparing Receptor Activation with Desensitization

Receptor activation should precede receptor deactivation. Therefore, we measured the rate-limiting step in PTHR-deactivation (Vilardaga, (2002), loc. cit.; Castro, Endocrinology 143 (2002), 3854-3865), the association of β-arrestin with the receptor, again with a FRET-based approach. To this end, we co-expressed functional PTHR carrying CFP at its C-terminus (PTHR-CFP$_{C\text{-}term}$) and β-arrestin2 fused at its C-terminus to YFP (β-arrestin2-YFP). Measuring the appearance of FRET between the CFP and the YFP then monitored PTH-induced binding of β-arrestin2 to the receptor. The dynamics of this signal were compared with the receptor activation of PTHR-cam (FIG. 5). The initial ratio $F^*_{535}/F^*_{480}$ was 1.10±0.05 for cells co-expressing PTHR-CFP$_{C\text{-}term}$ and β-arrestin2-YFP. After addition of PTH (100 nM), the ratio increased by up to 32±11% with a $t_{1/2}$ of 150±12.1 s (n=8), reflecting the PTH-mediated receptor/β-arrestin2 association. The same concentration of PTH (100 nM) had a 5-fold faster effect on PTHR-cam, with a $t_{1/2}$ of 32±1.9 s (n=4 experiments). Furthermore, the lag time between addition of PTH and the beginning of the response was about three times shorter for the activation signal (PTHR-cam) than for β-arrestin translocation (FIG. 5, inset). Thus, the signal for receptor activation does indeed begin earlier and proceeds much faster than that for receptor deactivation.

EXAMPLE VII

Differential Speed of Activation Between Hormone and Neurotransmitter Receptors Time-resolved determination of the FRET signals recorded from single cells after activation with various concentrations of PTH and noradrenaline, respectively, allowed the analysis of the switch kinetics (FIG. 6). Under all conditions, the decrease of the ratio $F^*_{535}/F^*_{480}$ followed a monoexponential time-course. Increasing concentrations of agonist resulted in shorter delay times as well as faster time-courses of the signals. At low agonist concentrations, the rate constants ($k_{obs}$) increased in proportion to agonist concentration (FIG. 6B), indicating that agonist binding to the receptors was the rate-limiting step. At higher concentrations of agonist, the rate constants reached a maximum, suggesting that a step other than the collisional probability of agonist/receptor became rate-limiting. This limit is not due to technical limitations of the system, which allows complete solution exchange in less than 10 ms. Thus, it is most likely the agonist-mediated conformational switch of the receptors. The time constant required for the receptor activation was less than 40 ms in the case of the $\alpha_{2A}$AR-cam. This is more than 5000 times faster than the activation time measured for chemically labelled, purified $\beta_2$-adrenergic receptors (Gether, J. Biol. Chem. 270 (1995), 28268-28275; Jensen, J. Biol. Chem. 276 (2001), 9279-9290; Ghanouni, (2001), loc. cit.; Ghanouni, Proc. Natl. Acad. Sci. USA 98 (2001), 5997-6002) and corresponds well to the physiological requirements of neurotransmitter receptors. In contrast, the kinetics of the FRET-signal were 25-fold slower (τ=1s) for the PTH-receptor. This may be explained by the fact that PTH is a large agonist and that its binding appears to involve several contact points both in the extended N-terminus and in the core of the PTHR (Gardella, Trends Endocrinol. Metabolism 12 (2001), 210-217).

The saturation of the $k_{obs}$-values together with the concentration-dependent delay times (FIG. 6) are compatible with a simple two-step process of first-order agonist binding and subsequent receptor activation. The delay times indicate that the FRET signal reflects the conformational switch underlying receptor activation and not just receptor-agonist contact. Mechanistically, this switch appeared to be similar in a class 1 and a class 2 GPCR, but the activation was much faster in the class 1 $\alpha_{2A}$AR-cam. The slower activation of the class 2 PTH receptor is compatible with the slow hormonal effects of PTH, compared with the fast synaptic action of noradrenaline. Millisecond switch times have so far been thought to be limited to ion channel receptors (Chang, Nature Neurosci. 5 (2002), 1163-1168) or to rhodopsin (Okada, Trends Biochem. Sci. 26 (2001), 318-324). However, data presented herein document that also a "neurotransmitter GPCR" can be switched in the millisecond time scale, and it is shown that the extent said switching is dependent on the intrinsic efficacy of the ligand.

Figure 14:
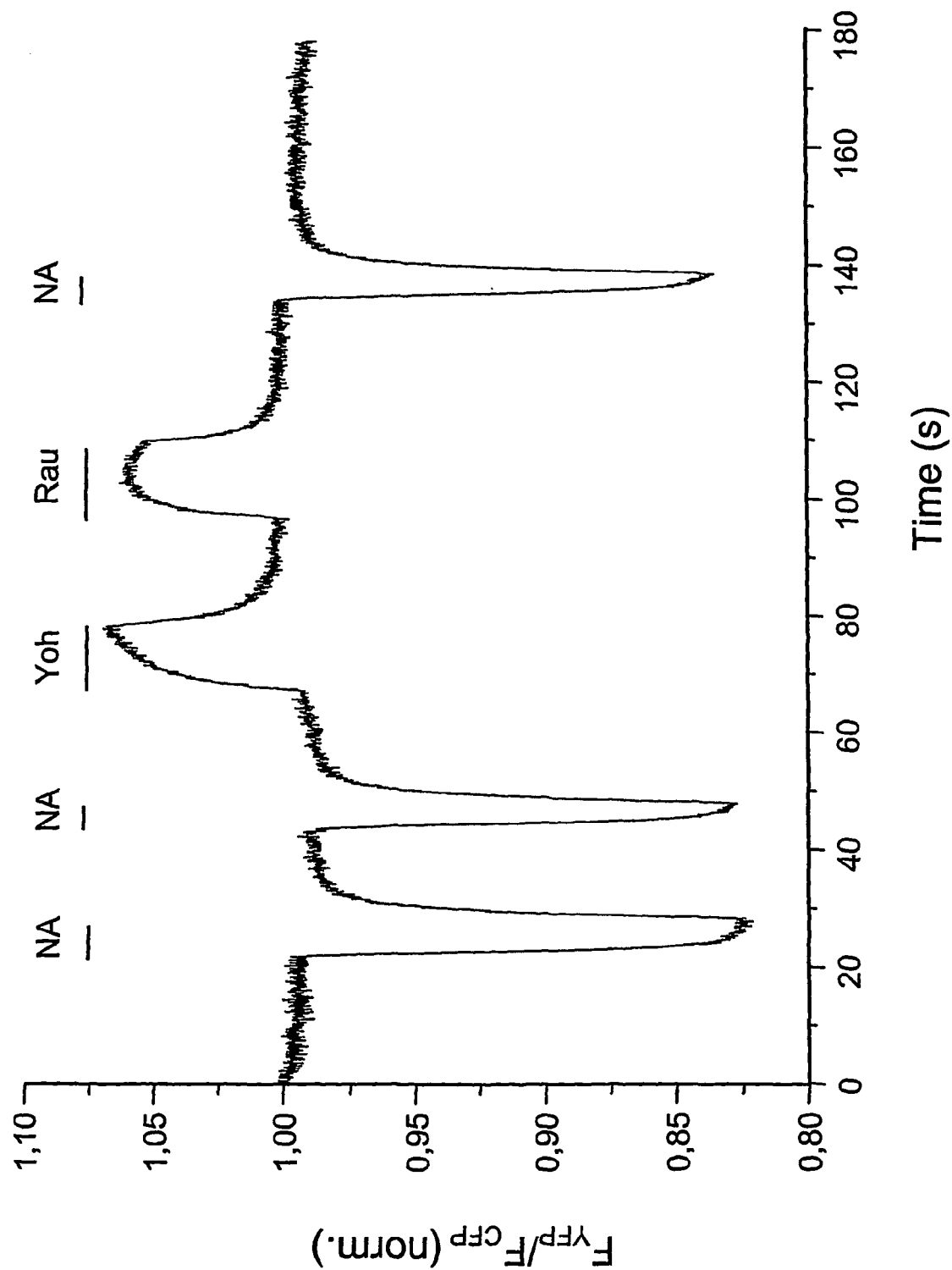

As documented in appended FIG. 14, the present invention also provides for tools which allow for the differentiation between agonists and inverse agonists.

EXAMPLE VIII

A2A Adenosine Receptor Activation Determined by Intramolecular FRET

Recombinant YFP and eCFP were fused to recombinant human A2A adenosin receptors, similarly as described for alpha2A adrenergic receptors and PTH/PTHrP receptors using conventional cloning strategies. Specifically amino acids between amino acid 14 after the 5$^{th}$ transmembrane helix and amino acid 10 proximal to the 6$^{th}$ transmembrane helix were replaced by eCFP (corresponding to the third intracellular loop). The C-terminus of the receptor was truncated after amino acid 33 and was fused to YFP.

HEK293 cells were transiently transfected with A2A-CFP14/10-YFPC33 (exemplified constructs shown in SEQ ID NOS: 15 and 16) using effectene (Qiagen) according to the manufacturers protocol. 12 h post transfection cells were replated on glass coverslips coated with poly-L-lysine and cultured for another 12-36 h. Glass coverslips were subsequently washed with HEPES buffered solution and placed under an inverted fluorescence microscope (Zeiss axiovert 135). Using excitation light of 436 nm (bandwidth 10 nm) cells expressing fluorescent receptors were excited and emission of single cells was detected at 480 nm (480±20 nm) for CFP-emission and 535 nm (535±15 nm) using a dual wavelength detection system equipped with amplified photodiodes (Till photonics). CFP and YFP emission in response to 10 ms illumination periods every 100 ms was recorded and after correcting for bleed through of the CFP emission into the 535 nm channel a ratio of YFP/CFP emission was calculated (nFRET).

Cells were continuously superfused with control solution (in mM: 140 NaCl; 5.4 KCl; 2 CaCl$_2$; 1 mM MgCl$_2$; 10 mM Glucose and 10 HEPES/NaOH pH 7.3) using a fast solenoid valve operated superfusion system ALA-VM8 (ALA Scientific Instruments). Upon superfusion with agonist containing solution (100 µM adenosine) a rapid 1.5-2% decrease in nFRET was detected, less in amplitude, but otherwise similarly as described for alpha2A-cam and PTHR-cam8. After withdrawal of agonist, nFRET increased to the initial value within 5-10 s.

These results indicate that agonist induced conformational changes of A2A adenosine receptors can be detected by changes in intramolecular FRET of A2A-CFP14/10-YFPC33 receptors, similar as described for alpha2A-cam and PTHR-cam8.

EXAMPLE IX

Inactivation of Human G Proteinα (Gα) by Introduction of a Fluorophore

Human Gαs was mutated by introducing of the YFP into the loop alphaA-alphaB at the position 116 and was coexpressed with Gβγ subunits of heterotrimeric G proteins. Using fluorescence microscopy no membrane-targeting of Gαs was observed. Instead the fluorescent protein was found in perinuclear spots, most likely resembling lysosomes. The introduction of the YFP tag into Gαs led to a severe defect of either protein folding or targeting of this fusion protein in intact cells. In addition no FRET between fluorescent Gβγ-CFP subunits and Gα-YFP was detected, indicating no proper interaction of these natural binding partners.

EXAMPLE X

Pharmacological Parameters as Recorded with a Recombinant Seven-Transmembrane Receptor Comprising as Labels FlAsH and CFP FlAsH-Labelling of the Cells:
Cells (HEK or HeLa) were transiently transfected with one of the listed adenosine receptor constructs. 24-48 hours after transfection, cells were labelled according to the following procedure (Gaietta et al., Science 296 (2002), 503-507).

FlAsH-EDT was used in a final concentration of 1 µM in the presence of 12.5 µM EDT. The labelling was performed for 1 hour at 37° C. in 1× Hank's Balanced Salt Solution (HBSS, Gibco-BRL, Invitrogen) supplemented with D-Glucose (1 g/l). Free and non-specifically bound FlAsH was removed by washing with EDT (200 µM in HBSS+ glucose). FlaSH has been described by Griffin (2000), Meth. Enzym. 327, 565-578.

Detailed Description:
1. Prepare a 25 mM EDT (Ethanedithiol) solution in DMSO by mixing 2.1 µl of EDT with 1 ml of DMSO (prepare fresh each time).
2. Add 1 µl of 25 mM EDT to 1 µl of FlAsH (original stock from Invitrogen is 2 mM FlAsH in DMSO/H2O; working concentration of FlAsH is 1 µM final in tissue culture dish).
3. Incubate at room temperature for 5'-10'. This step ensures that all FlAsH is in the FlAsH-EDT2 form. Some EDT molecules may "fall off" FlAsH during storage. It seems a slightly basic pH may further help the binding of EDT to FlAsH (see step 6).

While incubating EDT/FlAsH mix, prepare the cells as follows:
4. Wash the tissue culture dish 3 times with 1×HBSS/glucose (use commercial "complete" HBSS, no phenol red, supplemented with 1 g/l D+ glucose).
5. Add 2 ml of HBSS/glucose solution to the dish.
6. Take 200 µl of HBSS/glucose from the dish and add it to the tube containing 2 µl EDT/FlAsH as prepared in Step 2. Mix well and transfer the solution back to the dish. One may incubate the EDT/FlAsH/HBSS solution for 10'-15' to ensure complete binding of EDT, and then add it back to the dish. Gently swirl the labelling solution and incubate the tissue culture dish for 1 hour.
7. Prepare washing solution by mixing 42 µl of EDT with 1 ml DMSO (500 mM EDT in DMSO). Add 20 µl of this mix to 50 ml HBSS/glucose solution, resulting in a HBSS/Glucose solution containing 200 µM EDT (washing solution).
8. Aspirate the cells and add 3 ml of washing solution. Incubate the cells for 10 min. Repeat this washing step three times. At the end wash the cells with HBSS/glucose solution without EDT. Cells are now ready to be imaged.

Employing the above mentioned labelling protocol and the receptor constructs (SEQ ID NOS 39 through 46), were developed an alternative method to measure receptor activation in living cells. The previously used YFP was substituted by a fluophor called FlAsH, which specifically binds to an amino acid sequence consisting of a minimum of six amino acids (CCXXCC, were XX is most preferably PG), and exhibits comparable spectroscopic properties to YFP when bound to peptides. The principle of the method and the labelling specificity is proven by the use a set of three slightly different receptor constructs. The receptor constructs, namely A2A-CFP-C49 (SEQ ID NOS: 45 and 46), A2A-ModelPG-CFP-C49 (SEQ ID NOS 43 and 44), and A2A-FlAsHPG-CFP-C49 (SEQ ID NOS 39 and 40) all contain a CFP at the same position of the C-terminus. However, they differ in their binding capability for FlAsH and the position in which the minimal CCPGCC motif was attached. The construct A2A-CFP-C49 (SEQ ID NOS 45 and 46) does not contain the CCPGCC motif and therefore is incapable of binding FlAsH. The construct A2A-ModelPG-CFP-C49 (SEQ ID NOS 43 and 44) does contain the CCPGCC motif and therefore is capable of binding FlAsH, however, the CCPGCC is directly attached to the CFP sequence and therefore both Fluophores are invariant with respect to their relative conformation.

Figure 9B:
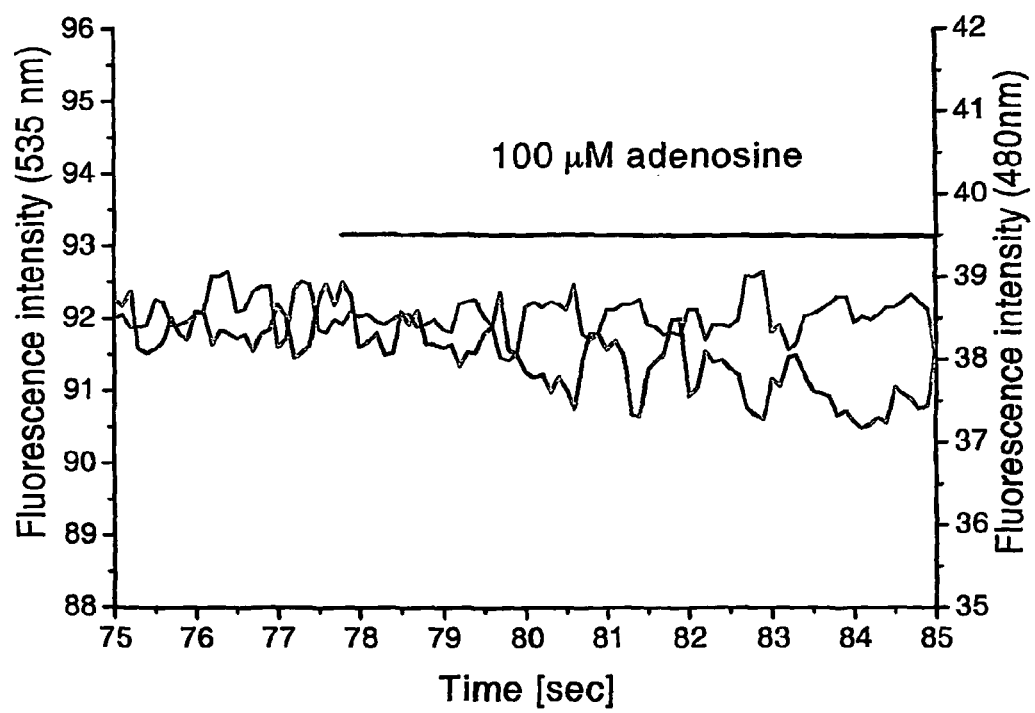
Figure 10B:
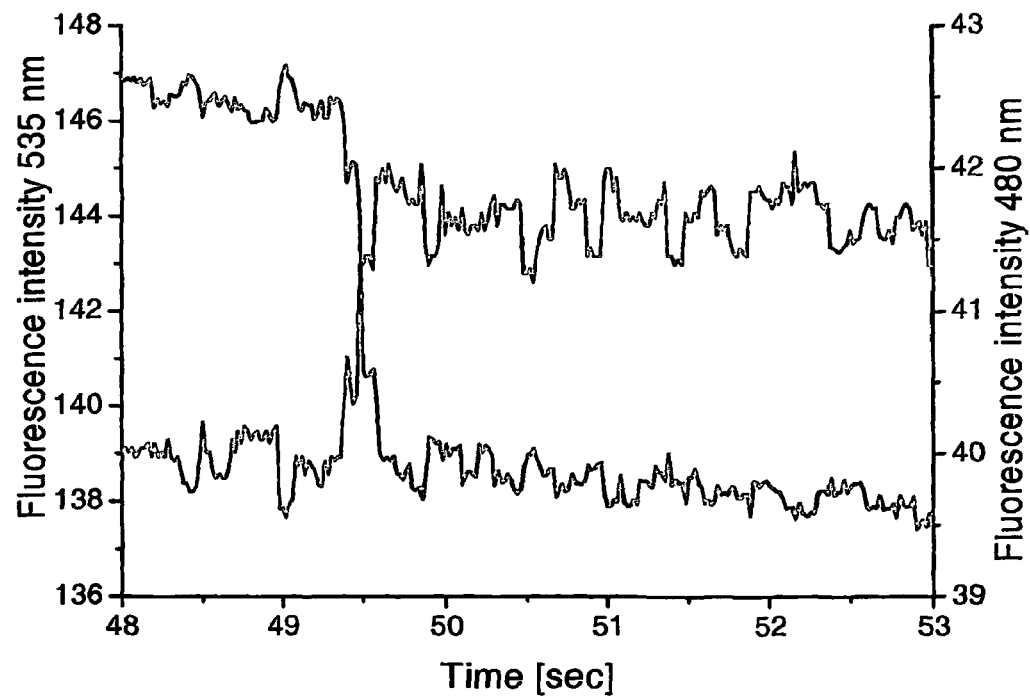

Hence this construct can not monitor and agonist dependent change of the receptor conformation. The construct A2A-FlAsHPG-CFP-C49 (SEQ ID NOS 39 and 40) does contain the CCPGCC motif and therefore is capable of binding FlAsH. In this construct the CCPGCC motif was placed into the third intracellular loop while the CFP was still attached to the C-terminus of the receptor. According to the above protocol transiently transfected HeLa cells were labelled with FlAsH, and the cells were analysed by confocal microscopy. FIG. 7 shows a representative example of the observed results. The top row shows cells that were excited at 430 nm and therefore monitor the CFP molecule attached to the receptor. As can be seen in FIG. 7 each of the three different receptor constructs is located in the plasma membrane of the cell. The FlAsH fluophor is specifically excited at 514 nm. Therefore we excited the same cells also at 514 nm. The results are shown in the second row in FIG. 7. It can be seen that all cells are slightly non-specifically stained and exhibit a dim yellow fluorescence. However, the construct A2A-CFP-C49 (SEQ ID NOS 45 and 46) does not exhibit a significant yellow fluorescent labelling at the plasma membrane when excited at 514 nm as can be seen for A2A-ModelPG-CFP-C49 (SEQ ID NOS 43 and 44) and A2A-FlAsHPG-CFP-C49 (SEQ ID NOS 39 and 40). This figure proofs two points at the same time. First, the specific fluorescence observed for constructs A2A-ModelPG-CFP-C49 (SEQ ID NOS 43 and 44) and A2A-FlAsHPG-CFP-C49 (SEQ ID NOS 39 and 40) is not due to an excitation of CFP at 514 nm, otherwise the construct A2A-CFP-C49 would also exhibit a similar fluorescent staining of the plasma membrane as the other two constructs do, and second the labelling with FlAsH is specific for the CCPGCC motif since this is the only variation between the constructs A2A-FlAsHPG-CFP-C49 (SEQ ID NOS 39 and 40) and A2A-CFP-C49 (SEQ ID NOS 45 and 46). We than went on to investigate if this novel system could also be used to measure the agonist dependent conformational change of GPCRs. Therefore we transfected HEK or HeLa cells with the appropriate receptor constructs and measured the fluorescence signal of single cells. Representative results for each of the constructs are shown in FIGS. 8 through 10. In FIGS. 8A and B results for the construct A2A-CFP-C49 (SEQ ID NOS 45 and 46) are shown. It can be seen that the fluorescence ratio does not change upon superfusion with 100 μM adenosine. As shown in FIG. 9, similar results were observed for constructs A2A-ModelPG-CFP-C49 (SEQ ID NOS 43 and 44). As predicted, this construct does not show an agonist dependent change of the fluorescence when superfused with 100 μM adenosine. However, when comparing the difference in the relative fluorescence ratios, one can see that construct A2A-ModelPG-CFP-C49 does show a significant fluorescence at 535 nm while A2A-CFP-C49 does not exhibit this fluorescence. This is a further indication that the CCPGCC motif does specifically bind FlAsH. In FIG. 10 the response of the construct A2A-FlAsHPG-CFP-C49 (SEQ ID NOS 39 and 40) to superfusion with 100 μM adenosine is shown. It can be seen that a rapid change of 10% of the fluorescent ratio was observed that is comprised of a gain in fluorescence intensity for CFP while the intensity for FlAsH decreases (FIG. 10B). This is the same type of change that was previously observed for the system employing CFP and YFP (compare FIG. 1). Therefore we can conclude that both systems can monitor an agonist dependent conformational change of the receptor construct.

To see whether the two systems were different with respect to the magnitude of the response, we created another construct for the pair FlAsH and CFP that was comparable to the previously used A2A-"chameleon" (SEQ ID NOS 15 and 16). This new construct A2A-FlAsHPG-CFP-C33 (SEQ ID NOS 41 and 42) is identical with A2A-"chameleon" with respect to the C-terminal position at which the fluophore was attached. However, in the third intracellular loop it contains the CCPGCC sequence that can bind FlAsH, rather that a GFP variant, but the positions of the fluophores were similar. As shown in FIG. 11 construct A2A-FlAsHPG-CFP-C33 underwent a rapid change of the fluorescence ratio upon agonist stimulation and the change was reversible after the agonist stimulation was stopped. The ration change was about 10% of the total signal and therefore was 4 times greater than the 2.5% ratio change observed for the A2A-"chameleon" (SEQ ID NOS 15 and 16).

To investigate the pharmacological parameters of the receptor constructs, we determined radioligand binding properties and adenylylcyclase activity as a measure of receptor signalling properties. The results are shown in FIG. 12. It can be seen that, with respect to radioligand binding, all tested adenosine receptor constructs were similar. However, as shown in FIG. 12 the adenylyl cyclase activity for the A2A-"chameleon" (SEQ ID NOS 15 and 16) was greatly shifted to the right (impaired G-protein coupling) and away from the response when compared to the normal A2A wild-type receptor (SEQ ID NOS 5 and 6). This is different for the novel constructs using FlAsH instead of GFP-variant. The adenylyl cyclase response for these constructs is very similar to (A2A-FlAsHPG-CFP-C33; SEQ ID NOS 41 and 42) or indistinguishable (A2A-FlAsHPG-CFP-C49; SEQ ID NOS 39 and 40) from the A2A wild-type receptor (SEQ ID NOS 5 and 6). If intact downstream signalling is important the use of the novel FlAsH/CFP system is preferable over the YFP/CFP system.

Furthermore using the construct (A2A-FlAsHPG-CFP-C49; SEQ ID NOS 39 and 40) we could show that this system can be employed for the screening of novel ligands at correspondingly modified receptors. Therefore we measured the relative change of the fluorescence signal in relation to ligand concentration. The relative change was plotted against the ligand concentration (FIG. 13) and a clear concentration dependency of the signal change could be visualized.

The invention claimed is:

1. Recombinant seven-transmembrane receptor, further defined as a recombinant G protein-coupled receptor, whereby the amino terminus of said recombinant receptor is located on an extracellular side and the carboxy-terminus is located on an intracellular side of a membrane, comprising at least two detectable labels, whereby a first of said at least two detectable labels is, or is located on, the carboxy-terminus and whereby a second of said at least two labels is, or is located on, the first or third intracellular loop; or whereby a first of said at least two labels is, or is located on, the first intracellular loop and a second of at said at least two labels is, or is located on, the third intracellular loop, and further wherein the first and second labels are detectable by resonance energy transfer.

2. Recombinant membrane receptor of claim 1, whereby said first label is, or is located on, the third intracellular loop of said membrane receptor and wherein said second label is, or is located on, the carboxy terminus.

3. Recombinant membrane receptor of claim 1, whereby said G-protein-coupled receptor (GPCR) is selected from the group consisting of a rhodopsin/β2 adrenergic receptor-like GPCR, a glucagon/VIP/calcitonin receptor-like GPCR and a metabotropic neurotransmitter/calcium receptor.

4. Recombinant membrane receptor of claim 3, whereby said rhodopsin/β2-adrenergic receptor-like GPCR is the α2A adrenergic receptor or the adenosine receptor A2A or wherein said glucagon/VIP/calcitonin receptor-like GPCR is the parathyroid hormone (PTH) receptor.

5. Recombinant membrane receptor of claim 1, whereby said detectable labels are fluorescent labels or bioluminescent labels.

6. Recombinant membrane receptor of claim 5, whereby said fluorescence labels are selected from the group consisting of green fluorescent protein, yellow fluorescent protein, cyan fluorescent protein, blue fluorescent protein, citrine, sapphire and dsRed, whereby said bioluminescent labels is luciferase, or whereby said fluorescence label is produced by binding a fluorescein arsenical helix binder compound to specific epitopes of said $1^{st}$ and $3^{rd}$ loop or said C-terminus of the recombinant seven-transmembrane receptor.

7. Recombinant membrane receptor of claim 1, whereby said G-protein-coupled receptor comprising at least two labels is selected from the group consisting of:
(a) a polypeptide as shown in SEQ ID NOS: 12, 14, 16, 40 or 42; and
(b) a polypeptide encoded by a nucleic acid sequence as depicted in any one of SEQ ID NOS:11, 13, 15, 39 or 41.

8. Recombinant membrane receptor of claim 1, wherein the third intracellular loop being or comprising said first label is selected from the group consisting of
(a) a polypeptide depicted in SEQ ID NOS: 18, 22 or 26; and
(b) a polypeptide encoded by a nucleic acid sequence as depicted in SEQ ID NOS: 17, 21 or 25.

9. A diagnostic composition comprising the recombinant membrane protein of claim 1.

10. A kit comprising the recombinant membrane protein of claim 1.

11. Recombinant membrane receptor of claim 1, whereby the labels are detectable by fluorescence or bioluminescence.

* * * * *

UNITED STATES PATENT AND TRADEMARK OFFICE
CERTIFICATE OF CORRECTION

| | | |
|---|---|---|
| PATENT NO. | : 8,084,575 B2 | |
| APPLICATION NO. | : 10/538985 | |
| DATED | : December 27, 2011 | |
| INVENTOR(S) | : Moritz Bünemann et al. | |

It is certified that error appears in the above-identified patent and that said Letters Patent is hereby corrected as shown below:

In title page, item (73) Assignee, delete "Julius-Maximilians-Universitat" and insert --Julius-Maximilians-Universität Würzburg-- therefor Signed and Sealed this
Sixth Day of March, 2012

David J. Kappos
*Director of the United States Patent and Trademark Office*